US011505590B2

(12) United States Patent
Hayes et al.

(10) Patent No.: US 11,505,590 B2
(45) Date of Patent: Nov. 22, 2022

(54) T CELL RECEPTORS

(71) Applicant: IMMUNOCORE LIMITED, Abingdon (GB)

(72) Inventors: Conor Hayes, Abingdon (GB); Linda Hibbert, Abingdon (GB); Nathaniel Ross Liddy, Abingdon (GB); Tara Mahon, Abingdon (GB); Marine Raman, Abingdon (GB)

(73) Assignee: IMMUNOCORE LIMITED, Abingdon (GB)

( * ) Notice: Subject to any disclaimer, the term of this patent is extended or adjusted under 35 U.S.C. 154(b) by 339 days.

(21) Appl. No.: 16/092,174

(22) PCT Filed: Apr. 7, 2017

(86) PCT No.: PCT/GB2017/050985
§ 371 (c)(1),
(2) Date: Oct. 8, 2018

(87) PCT Pub. No.: WO2017/175006
PCT Pub. Date: Oct. 12, 2017

(65) Prior Publication Data
US 2019/0092834 A1 Mar. 28, 2019

(30) Foreign Application Priority Data
Apr. 8, 2016 (GB) .................................... 1606009

(51) Int. Cl.
*C07K 14/725* (2006.01)
*A61P 35/00* (2006.01)
*C07K 16/28* (2006.01)
*C07K 16/30* (2006.01)
*C12N 15/62* (2006.01)

(52) U.S. Cl.
CPC .......... *C07K 14/7051* (2013.01); *A61P 35/00* (2018.01); *C07K 16/2833* (2013.01); *C07K 16/30* (2013.01); *C12N 15/62* (2013.01); *C07K 2317/56* (2013.01); *C07K 2317/64* (2013.01); *C07K 2317/92* (2013.01); *C07K 2317/94* (2013.01); *C07K 2319/035* (2013.01)

(58) Field of Classification Search
None
See application file for complete search history.

(56) References Cited

U.S. PATENT DOCUMENTS

| 2007/0082362 | A1 | 4/2007 | Jakobsen |
| 2009/0214551 | A1 | 8/2009 | Jakobsen |
| 2009/0324566 | A1 | 12/2009 | Shiku |
| 2013/0109053 | A1 | 5/2013 | Macdonald |
| 2014/0371085 | A1 | 12/2014 | Jakobsen |
| 2014/0378389 | A1 | 12/2014 | Robbins |

FOREIGN PATENT DOCUMENTS

| CO | 20170010502 A2 | 1/2018 |
| CO | 20180010453 A2 | 10/2018 |
| CO | 20180010811 A2 | 10/2018 |
| WO | 199918129 A1 | 4/1999 |
| WO | 2000020445 A2 | 4/2000 |
| WO | 2000020445 A3 | 4/2000 |
| WO | 200148145 A2 | 7/2001 |
| WO | 200148145 A3 | 1/2002 |
| WO | 2003020763 A2 | 3/2003 |
| WO | 2003020763 A3 | 5/2003 |
| WO | 2004023973 A2 | 3/2004 |
| WO | 2004033685 A1 | 4/2004 |
| WO | 2004023973 A3 | 9/2004 |
| WO | 2004074322 A1 | 9/2004 |
| WO | 2010133828 A1 | 11/2010 |
| WO | 2013053021 A1 | 4/2013 |
| WO | 2014096803 A1 | 6/2014 |
| WO | 2014118236 A2 | 8/2014 |
| WO | 2014118236 A3 | 10/2014 |
| WO | 2014160030 A2 | 10/2014 |
| WO | 2014160030 A3 | 11/2014 |
| WO | 2016007570 A2 | 1/2016 |
| WO | 2016022400 A1 | 2/2016 |
| WO | 2016007570 A3 | 3/2016 |

OTHER PUBLICATIONS

Rudikoff et al. (Proc. Natl. Acad. Sci. USA, 79: 1979-1983, Mar. 1982). (Year: 1982).*
Colman (Research in Immunology, 145:33-36, 1994). (Year: 1994).*
Brown et al. (J Immunol. May 1, 1996;156(9):3285-91). (Year: 1996).*
Bedouelle et al. (FEBS J. Jan. 2006;273(1):34-46). (Year: 2006).*
Vajdos et al. (J Mol Biol. Jul. 5, 2002;320(2):415-28). (Year: 2002).*
Aleksic, M. et al. (2012). "Different Affinity Windows for Virus and Cancer-Specific T-Cell Receptors: Implications for Therapeutic Strategies," Eu J Immunol. 42(12):13174-3179.
Altschul, S.F. et al. (Oct. 5, 1990). "Basic Local Alignment Search Tool," J. Mol. Biol. 215(3):1403-410.
Altschul, S.F.et al. (Sep. 1, 1997). "Gapped BLAST and PSI-BLAST: A New Generation of Protein Database Search Programs," Nucleic Acids Res. 25(17):3389-3402.
Arstila, T.P. et al. (Oct. 29, 1999) "A Direct Estimate of the Human αβ T Cell Receptor Diversity," Science 286 (5441):958-961.
Bergeron, A. et al. (2009, e-pub. Apr. 14, 2009). "High Frequency of MAGE-A4 and MAGE-A9 Expression in High-Risk Bladder Cancer," Int J Cancer 125(6):1365-1371.

(Continued)

*Primary Examiner* — Zachary S Skelding
(74) *Attorney, Agent, or Firm* — Morrison & Foerster LLP

(57) ABSTRACT

The present invention relates to T cell receptors (TCRs) that bind the HLA-A*02 restricted peptide GVYDGREHTV (SEQ ID NO: 1) derived from the germline cancer antigen MAGE A4. Said TCRs may comprise non-natural mutations within the alpha and/or beta variable domains relative to a native MAGE A4 TCR. The TCRs of the invention are particularly suitable for use as novel immunotherapeutic reagents for the treatment of malignant disease.

45 Claims, 18 Drawing Sheets

Specification includes a Sequence Listing.

(56) References Cited

OTHER PUBLICATIONS

Bossi, G. et al. (Nov. 2013). "Examining the Presentation of Tumor-Associated Antigens on Peptide-Pulsed T2 Cells," Oncolumnunology 12(11):e26840, 7 pages.

Boulter, J.M. et al. (2003). "Stable, Soluble T-Cell Receptor Molecules for Crystallization and Therapeutics," Protein Eng 16(9):707-711.

Cabezón, T et al. (2013). "Proteomic Profiling of Triple-Negative Breast Carcinomas in Combination With a Three-tier Orthogonal Technology Approach Identifies Mage-A4 as Potential Therapeutic Target in Estrogen Receptor Negative Breast Cancer," Mol Cell Proteomics 12(2):381-394.

Cameron, B.J. et al. (Aug. 7, 2013). "Identification of a Titin-Derived HLA-A1-Presented Peptide as a Cross-Reactive Target for Engineered MAGE A3-Directed T Cells," Sci Trans Med. 5(197):197ra103, 24 pages.

Cat. No. MHC-LC1146 "APC-A*02:01/Human MAGEA4 (GVYDGREHTV) MHC Tetramer," retrieved from https://www.creativebiolabs.net/pdf/MHC-LC1146.pdf, 2 pages.

Chen, X. et al. (Oct. 15, 2013). "Fusion Protein Linkers: Property, Design and Functionality," Advanced Drug Delivery Reviews 65(10):1357-1369, 32 pages.

Chervin, A.S. et al. (Dec. 31, 2008). "Engineering Higher Affinity T Cell Receptors Using a T Cell Display System," J. Immuno. Methods 339(2):175-184, 21 pages.

Cuffel, C. et al. (2011). "Pattern and Clinical Significance of Cancer-Testis Gene Expression in Head and Neck Squamous Cell Carcinoma," Int J Cancer 128(11):2625-2634.

Cunha-Neto, E. (Feb. 1999). "MHC-Restricted Antigen Presentation and Recognition: Constraints on Gene, Recombinant and Peptide Vaccines in Humans," Brazilian Journal of Medical and Biological Research 32:199-205.

Davis, M.M. et al. (Apr. 1998). "Ligand Recognition by $\alpha\beta$ T Cell Receptors," Annu Rev Immunol 16:(15):523-544.

De La Hera, A. et al. (1991). "Structure of the T Cell Antigen Receptor (TCR): Two CD3 Epsilon Subunits in a Functional TCR/CD3 Complex," The Journal of Experimental Medicine 173(1):7-17.

De Plaen, E. et al. (1994). "Structure, Chromosomal Localization, and Expression of 12 Genes of the MAGE Family," Immunogenetics 40(5):360-369.

Dennis, M.S. et al. (Sep. 20, 2002). "Albumin Binding as a General Strategy for Improving the Pharmacokinetics of Proteins," J Biol Chem 277(38):35035-35043.

Devereux, J. et al. (1984). "A Comprehensive Set of Sequence Analysis Programs for the VAX," Nucleic Acids Research 12(1):387-395.

Dozier, J.K. et al. (Oct. 28, 2015). "Site-Specific PEGylation of Therapeutic Proteins," Int J Mol Sci. 16(10):25831-25864.

Duffour, M.-T. et al. (1999). "A MAGE-A4 Peptide Presented by HLA-A2 is Recognized by Cytolytic T Lymphocytes," Eur J Immunol 29(10):3329-3337.

Epel, M. et al. (Nov. 2002, e-pub. Sep. 13, 2002). "A Functional Recombinant Single-Chain T Cell Receptor Fragment Capable of Selectively Targeting Antigen-Presenting Cells," Cancer Immunol Immunother. 51(10):565-573.

Folch, G. et al. (2000). "The Human T Cell Receptor Beta Diversity (TRBD) and Beta Joining (TRBJ) Genes," Exp Clin Immunogenet 17(2):107-114.

Folch, G. et al. (2000). "The Human T cell Receptor Beta Variable (TRBV) Genes," Exp Clin Immunogenet 17(1):42-54.

Forghanifard, M.M. et al. (Aug. 1, 2011). "Cancer-Testis Gene Expression Profiling in Esophageal Squamous Cell Carcinoma: Identification of Specific Tumor Marker and Potential Targets for Immunotherapy," Cancer Biol Ther 12(3):191-197.

Garboczi, D.N. et al. (Apr. 1992). "HLA-A2-Peptide Complexes: Refolding and Crystallization of Molecules Expressed in *Eschericlhia coli* and Complexed With Single Antigenic Peptides," Proc Natl Acad Sci USA 89(8):3429-3433.

Gasser, B. et al. (Feb. 2007). "Antibody Production With Yeasts and Filamentous Fungi: On the Road to Large Scale?," Biotechnology Letters 29(2):201-212.

Holler, P.D. et al. (May 9, 2000). "In vitro Evolution of a T Cell Receptor With High Affinity for Peptide/MHC," Proc Natl Acad Sci USA 97(10):5387-5392.

Inaguma, Y. et al. (Jun. 2014, e-pub. Apr. 3, 2014). "Construction and Molecular Characterization of a T-Cell Receptor-Like Antibody and CAR-T Cells Specific for Minor Histocompatibility Antigen HA-1H," Gene Therapy 21(6):575-584.

International Preliminary Report on Patentability, dated Oct. 9, 2018, for PCT Application No. PCT/GB2017/050985, filed Apr. 7, 2017, 7 pages.

International Search Report and Written Opinion of the International Search Authority, dated Jun. 19, 2017, for PCT Application No. PCT/GB2017/050985, filed Apr. 7, 2017, 14 pages.

Jefferis, R. (Mar. 2009). "Glycosylation as a Strategy to Improve Antibody-Based Therapeutics," Nat Rev Drug Discov 8(3):226-234.

Jevsevar, S. et al. (Jan. 2010). "PEGylation of Therapeutic Proteins," Biotechnol J. 5(1):113-128, 52 pages.

June, C.H. et al. (Sep. 2014). "Engineered T Cells for Cancer Therapy," Cancer Immunol Immunother 63(9):969-975, 11 pages.

Karimi, S. et al. (May 2012). "Characterization of Melanoma-Associated Antigen—A Genes Family Differential Expression in Non-Small-Cell Lung Cancers," Clin Lung Cancer 13(3):214-219.

Karlin, S. et al. (Jun. 1993). "Applications and Statistics for Multiple High-Scoring Segments in Molecular Sequences," Proc. Natl. Acad. Sci. USA 90:5873-5877.

Karlin, S. et al. (Mar. 1990). "Methods for Assessing the Statistical Significance of Molecular Sequence Features by Using General Scoring Schemes," Proc. Natl. Acad. Sci. USA 87(6):2264-2268.

Lefranc, M.P. (2003). "IMGT® Databases, Web Resources and Tools for Immunoglobulin and T Cell Receptor Sequence Analysis, http://imgt.cines.fr," Leukemia 17(1):260-266.

Li, Y. et al. (Mar. 2005, e-pub. Feb. 20, 2005). "Directed Evolution of Human T-Cell Receptors With Picomolar Affinities by Phage Display," Nat Biotechnol. 23(3):349-354.

Liddy, N. et al. (Jun. 2012). "Monoclonal TCR-Redirected Tumor Cell Killing," Nat Med 18(6):980-987.

Jssin, N.M. et al. (2013). "Chapter 32—High-Affinity Moncloncal T-Cell Receptor (mTCR) Fusions," Fusion Protein Technologies for Biophamaceuticals: Applications and Challenges, 11 pages.

Maeda, Y. et al. (Jul. 1, 1997). "Engineering of Functional Chimeric Protein G-Vargula Luciferase," Analytical Biochemistry 249(2):147-152.

Maus, M.V. et al. (Jul. 2013). "T Cells Expressing Chimeric Antigen Receptors Can Cause Anaphylaxis in Humans," Cancer Immunology Research 1(1):26-31.

Muller, S. et al. (Dec. 2008). "Spliceosomal Peptide P140 for Immunotherapy of Systemic Lupus Erthematosus: Results of an Early Phase II Clinical Trial." Arthritis & Rheumatism: Offical Journal of the American College of Rheumatology 58(12):3783-3883.

Nazarov, V.I. (2015). "Review of Analysis Methods, Generation Models and Repertoire Selection Models Immune Receptor," New Information Technology in Automated Systems 18:270-280. English Abstract.

O'Callaghan, C.A. et al. (1999). "BirA Enzyme: Production and Application in the Study of Membrane Receptor±Ligand Interactions by Site-Specific Biotinylation," Anal Biochem 266(1):9-15.

Oates, M.E. et al. (2013, e-pub. Nov. 29, 2012). "$D^2P^2$: Database of Disordered Protein Predictions," Nucleic Acids Res. 41(D1):D508-D516.

Pearson, W.R. et al. (Apr. 1988). "Improved Tools for Biological Sequence Comparison," Proc. Natl. Acad. Sci. USA 85(8):2444-2448.

Purbhoo. M.A. et al. (2006). "Quantifying and Imaging NY-ESO-1/LAGE-1-Derived Epitopes on Tumor Cells Using High Affinity T Cell Receptors," J Immunol 176(12):7308-7316.

Rashtchian, A. (Feb. 1995). "Novel Methods for Cloning and Engineering Genes Using the Polymerase Chain Reaction," Curr Opin Biotechnol 6(1):30-36.

(56) References Cited

OTHER PUBLICATIONS

Robbins, P.F. et al. (2008). "Single and Dual Amino Acid Substitutions in TCR CDRs Can Enhance Antigen-Specific T Cell Functions," J Immunol. 180:6116-6131.

Robins, H.S. et al. (Nov. 5, 2009, e-pub. Aug. 25, 2009). "Comprehensive Assessment of T-Cell Receptor β-Chain Diversity in α62 T Cells," Blood 114(19):4099-4107, 20 pages.

Rosenberg, S.A. et al. (Apr. 2008). "Adoptive Cell Transfer: A Clinical Path to Effective Cancer Immunotherapy," Nat Rev Cancer 8(4):299-308, 22 pages.

Sambrook, J. et al. (1989). Molecular Cloning—A Laboratory Manual, 2nd Edition, Maniatis, T.(ed.) et al., Cold Spring Harbor Laboratory Press, New York, NY pp. v-xxxii, 28 pages, (Table of Contents only).

Sambrook, J. et al. (2001). Molecular Cloning: A Laboratory Manual Cold Spring Harbor Laboratory Press, Cold Spring Harbor, N Y., 3rd ed., 1 page, Table of Contents.

Scaviner, D. et al. (2000). "The Human T Cell Receptor Alpha Joining (TRAJ) Genes," Exp Clin Immunogenet 17(2):97-106.

Scaviner, D. et al. (2000). "The Human T Cell Receptor Alpha Variable (TRAV) Genes," Exp Clin Immunogenet 17(2):83-96.

Schellenberger, V. et al. (Dec. 2009, e-pub. Nov. 15, 2009). "A Recombinant Polypeptide Extends the in vivo Half-Life of Peptides and Proteins in a Tunable Manner," Nat Biotechnol. 27(12):1186-1190.

Schlapschy, M. et al. (Aug. 2013, e-pub. Jun. 10, 2013). "PASylation: A Biological Alternative to PEGylation for Extending the Plasma Half-Life of Pharmaceutically Active Proteins," Protein Eng Des Sel. 26(8):489-501.

Sinclair, A.M. et al. (Aug. 2005). "Glycoengineering: The Effect of Glycosylation on the Properties of Therapeutic Proteins," Pharm Sci. 94(8):1626-1635.

Singapore Written Opinion; dated Jan. 9, 2020, for Singapore Patent Application No. 11201808797X, filed Apr. 7, 2017, 6 pages.

Svobodová, S. et al. (Feb. 2011. E-pub. Nov. 4, 2010). "Cancer-Testis Antigen Expression in Primary Cutaneous Melanoma Has Independent Prognostic Value Comparable to That of Breslow Thickness, Ulceration and Mitotic Rate," Eur J Cancer 47(3):460-469.

Teplyakov, A. et al. (2014, e-pub. Mar. 31, 2014). "Antibody Modeling Assessment II. Structures and Models," Proteins: Structure, Function, and Bioinformatics 82(8):1563-1582.

Torelli, A. et al. (Feb. 1994). "ADVANCE and ADAM: Two Algorithms for the Analysis of Global Similarity Between Homologous Informational Sequences," Comput. Appl. Biosci. 10(1):3-5.

Weidanz, J.A. et al. (Dec. 1, 1998). "Display of Functional αβ Single-Chain T-Cell Receptor Molecules on the Surface of Bacteriophage," J Immunol Methods. 221(1-2):59-76.

Willuda, J. et al. (Apr. 2001). "Tumor Targeting of Mono-, Di-, and Tetravalent Anti-p185HER-2 Miniantibodies Multimerized by Self-associating Peptides," J. Biol. Chem. 276(17):14385-14392.

Wilson, D.B. et al. (Feb. 2004). "Specificity and Degeneracy of T Cells," Mol Immunol 40(14-15):1047-1055.

Wooldridge, L. et al. (Jan. 6, 2012). "A Single Autoimmune T Cell Receptor Recognizes More Than a Million Different Peptides," J Biol Chem 287(2):1168-1177.

Yakirevich, E. et al. (Dec. 15, 2003). "Expression MAGE-A4 and NY-ESO1 Cancer-Testis Antigens in Serous Ovarian Neoplasms," Clinical Cancer Research 9(17):6453-6460.

Zhao, Y. et al. (2007). "High-Affinity TCRs Generated by Phage Display Provide CD4+ T Cells with the Ability to Recognize and Kill Tumor Cell Lines," J. Immunol, 179(9):5845-5854.

Bossi, G. (May 2014, e-pub. Feb. 15, 2014). "ImmTAC-Redirected Tumour Cell Killing Induces and Potentiates Antigen Cross-Presentation by Dendritic Cells," Cancer Immunology Immunotherapy 63(5):437-448.

\* cited by examiner

Figure 1

SEQ ID NO: 2 Amino acid sequence of a native alpha chain extracellular region. The variable region comprises residues 1 – 113. CDRs are underlined and CDR1, 2, 3 are designated SEQ ID NO: 6, 7 and 8, respectively. The FR2 and FR3 regions are in bold and are designated SEQ ID NO: 9 and 10, respectively. The constant region is shown in italics.

KNQVEQSPQSLIILEGKNCTLQCNYTVSPFSNLRWYKQDTGRGPVSLTIMTFSENTKSNGRYT
ATLDADTKQSSLHITASQLSDSASYICVVNHSGGSYIPTFGRGTSLIVHP*YIQKPDPAVYQLR*
*DSKSSDKSVCLFTDFDSQTNVSQSKDSDVYITDKTVLDMRSMDFKSNSAVAWSNKSDFACA*
*NAFNNSIIPEDTFFPSPESS*

SEQ ID NO: 3 Amino acid sequence of a native beta chain extracellular region. The variable region comprises residues 1-116. CDRs are underlined and are designated SEQ ID NO: 11, 12 and 13, respectively. The FR2 and FR3 regions are in bold and are designated SEQ ID NO: 14 and 15, respectively. The constant region is shown in italics.

DVKVTQSSRYLVKRTGEKVFLECVQDMDHENMFWYRQDPGLGLRLIYFSYDVKMKEKGDIP
EGYSVSREKKERFSLILESASTNQTSMYLCASSFLMTSGDPYEQYFGPGTRLTVT*EDLKNV*
*FPPEVAVFEPSEAEISHTQKATLVCLATGFYPDHVELSWWVNGKEVHSGVSTDPQPLKEQP*
*ALNDSRYCLSSRLRVSATFWQNPRNHFRCVQFYGLSENDEWTQDRAKPVTQIVSAEAWGR*
*AD*

Figure 2

SEQ ID NO: 4 Amino acid sequence of the soluble extracellular region of a native TCR alpha chain. CDRs are underlined. The constant region is shown in italics and the non-native cysteine residue is shown in bold (at position 48 of constant region).

KNQVEQSPQSLIILEGKNCTLQCNYTVSPFSNLRWYKQDTGRGPVSLTIMTFSENTKSNGRYT
ATLDADTKQSSLHITASQLSDSASYICVVNHSGGSYIPTFGRGTSLIVHP*YIQKPDPAVYQLR*
*DSKSSDKSVCLFTDFDSQTNVSQSKDSDVYITDKCVLDMRSMDFKSNSAVAWSNKSDFACA*
*NAFNNSIIPEDTFFPSPESS*

SEQ ID NO: 5 Amino acid sequence of the soluble extracellular region of a native TCR beta chain. CDRs are underlined. The constant region is shown in italics and the non-native cysteine residue is shown in bold (at position 57 of constant region). Additional non-native amino acids at position 75 and position 89 of the constant region are also shown in bold.

DVKVTQSSRYLVKRTGEKVFLECVQDMDHENMFWYRQDPGLGLRLIYFSYDVKMKEKGDIP
EGYSVSREKKERFSLILESASTNQTSMYLCASSFLMTSGDPYEQYFGPGTRLTVT*EDLKNV*
*FPPEVAVFEPSEAEISHTQKATLVCLATGFYPDHVELSWWVNGKEVHSGVCTDPQPLKEQP*
*ALNDSRYALSSRLRVSATFWQDPRNHFRCQVQFYGLSENDEWTQDRAKPVTQIVSAEAWGR*
*AD*

Figure 3

Amino acid sequences of mutated TCR alpha chain variable regions. CDRs are underlined and mutations are in bold

SEQ ID NO: 16 mutant alpha chain (c19v).
KNQVEQSPQSLIILEGKNVTLQCNYT<u>VSPFSN</u>LRWYKQDTGRGPVSLTI<u>MTFSEN</u>TKSNGRYT
ATLDADTKQSSLHITASQLSDSASYICVVN<u>HSGGLY</u>IPTFGRGTSLIVHP

SEQ ID NO: 17 mutant alpha chain (a7)
KNQVEQSPQSLIILEGKNVTLQCNYT<u>VSPFSN</u>LRWYKQDTGRGPVSLTI<u>LDYAIN</u>TKSNGRYT
ATLDADTKQSSLHITASQLSDSASYICVVN<u>HSGGSY</u>IPTFGRGTSLIVHP

SEQ ID NO: 18 mutant alpha chain (a12)
KNQVEQSPQSLIILEGKNVTLQCNYT<u>VSPFSN</u>LRWYKQDTGRGPVSLTI<u>MTFSEN</u>TKSNGRYT
ATLDADTKQSSLHITASQLSDSASYICVVN<u>RADGLY</u>IPTFGRGTSLIVHP

SEQ ID NO: 19 mutant alpha chain (a13)
KNQVEQSPQSLIILEGKNVTLQCNYT<u>VSPFSN</u>LRWYKQDTGRGPVSLTI<u>MTFSEN</u>TKSNGRYT
ATLDADTKQSSLHITASQLSDSASYICVVN<u>SANGLY</u>IPTFGRGTSLIVHP

SEQ ID NO: 20 mutant alpha chain (a13ka)
ANQVEQSPQSLIILEGKNVTLQCNYT<u>VSPFSN</u>LRWYKQDTGRGPVSLTI<u>MTFSEN</u>TKSNGRYT
ATLDADTKQSSLHITASQLSDSASYICVVN<u>SANGLY</u>IPTFGRGTSLIVHP

SEQ ID NO: 21 mutant alpha chain (a19)
KNQVEQSPQSLIILEGKNVTLQCNYT<u>VSPFSN</u>LRWYKQDTGRGPVSLTI<u>LDYAIN</u>TKSNGRYT
ATLDADTKQSSLHITASQLSDSASYICVVN<u>RADGLY</u>IPTFGRGTSLIVHP

SEQ ID NO: 22 mutant alpha chain (a19ka)
ANQVEQSPQSLIILEGKNVTLQCNYT<u>VSPFSN</u>LRWYKQDTGRGPVSLTI<u>LDYAIN</u>TKSNGRYT
ATLDADTKQSSLHITASQLSDSASYICVVN<u>RADGLY</u>IPTFGRGTSLIVHP

Figure 3 continued

SEQ ID NO: 23 mutant alpha chain (a13kaLS)
ANQVEQSPQSLIILEGKNVTLQCNYTVSPFSNLRWYKQDTGRGPVSLTILTFSENTKSNGRYT
ATLDADTKQSSLHITASQLSDSASYICVVNSASGLYIPTFGRGTSLIVHP

SEQ ID NO: 24 mutant alpha chain (a13kaLQ)
ANQVEQSPQSLIILEGKNVTLQCNYTVSPFSNLRWYKQDTGRGPVSLTILTFSENTKSNGRYT
ATLDADTKQSSLHITASQLSDSASYICVVNSAQGLYIPTFGRGTSLIVHP

SEQ ID NO: 46 mutant alpha chain (a36)
ANQVEQSPQSLIILEGKNVTLQCNYTVSPFSNLRWYKQDTGRGPVSLTIMTFSENTKSNGRYT
ATLDADTKQSSLHITASQLSDSASYICVVNSAQGLYIPTFGRGTSLIVHP

SEQ ID NO: 47 mutant alpha chain (a37)
ANQVEQSPQSLIILEGKNVTLQCNYTVSPFSNLRWYKQDTGRGPVSLTILTYSENTKSNGRYT
ATLDADTKQSSLHITASQLSDSASYICVVNSAQGLYIPTFGRGTSLIVHP

SEQ ID NO: 48 mutant alpha chain (a38)
ANQVEQSPQSLIILEGKNVTLQCNYTVSPFSNLRWYKQDTGRGPVSLTILTFSENTKSNGRYT
ATLDADTKQSSLHITASQLSDSASYICVVNHAQGLYIPTFGRGTSLIVHP

SEQ ID NO: 49 mutant alpha chain (a39)
ANQVEQSPQSLIILEGKNVTLQCNYTVSPFSNLRWYKQDTGRGPVSLTILTFSENTKSNGRYT
ATLDADTKQSSLHITASQLSDSASYICVVNSSQGLYIPTFGRGTSLIVHP

SEQ ID NO: 50 mutant alpha chain (a40)
ANQVEQSPQSLIILEGKNVTLQCNYTVSPFSNLRWYKQDTGRGPVSLTILTFSENTKSNGRYT
ATLDADTKQSSLHITASQLSDSASYICVVNSAGGLYIPTFGRGTSLIVHP

SEQ ID NO: 51 mutant alpha chain
(a41)ANQVEQSPQSLIILEGKNVTLQCNYTVSPFSNLRWYKQDTGRGPVSLTILTFSENTKSNG
RYTATLDADTKQSSLHITASQLSDSASYICVVNSAQGSYIPTFGRGTSLIVHP

Figure 3 continued

SEQ ID NO: 52 mutant alpha chain (a30)
ANQVEQSPQSLIILEGKNVTLQCNYTVSPFSNLRWYKQDTGRGPVSLTIMDYAINTKSNGRYT
ATLDADTKQSSLHITASQLSDSASYICVVNRADGLYIPTFGRGTSLIVHP

SEQ ID NO: 53 mutant alpha chain (a42)
ANQVEQSPQSLIILEGKNVTLQCNYTVSPFSNLRWYKQDTGRGPVSLTILTYAINTKSNGRYT
ATLDADTKQSSLHITASQLSDSASYICVVNRADGLYIPTFGRGTSLIVHP

SEQ ID NO: 54 mutant alpha chain (a31)
ANQVEQSPQSLIILEGKNVTLQCNYTVSPFSNLRWYKQDTGRGPVSLTILDFAINTKSNGRYT
ATLDADTKQSSLHITASQLSDSASYICVVNRADGLYIPTFGRGTSLIVHP

SEQ ID NO: 55 mutant alpha chain (a43)
ANQVEQSPQSLIILEGKNVTLQCNYTVSPFSNLRWYKQDTGRGPVSLTILDYSINTKSNGRYT
ATLDADTKQSSLHITASQLSDSASYICVVNRADGLYIPTFGRGTSLIVHP

SEQ ID NO: 56 mutant alpha chain (a32)
ANQVEQSPQSLIILEGKNVTLQCNYTVSPFSNLRWYKQDTGRGPVSLTILDYAENTKSNGRYT
ATLDADTKQSSLHITASQLSDSASYICVVNRADGLYIPTFGRGTSLIVHP

SEQ ID NO: 57 mutant alpha chain (a44)
ANQVEQSPQSLIILEGKNVTLQCNYTVSPFSNLRWYKQDTGRGPVSLTILDYAINTKSNGRYT
ATLDADTKQSSLHITASQLSDSASYICVVNHADGLYIPTFGRGTSLIVHP

SEQ ID NO: 58 mutant alpha chain (a33)
ANQVEQSPQSLIILEGKNVTLQCNYTVSPFSNLRWYKQDTGRGPVSLTILDYAINTKSNGRYT
ATLDADTKQSSLHITASQLSDSASYICVVNRSDGLYIPTFGRGTSLIVHP

SEQ ID NO: 59 mutant alpha chain (a45)
ANQVEQSPQSLIILEGKNVTLQCNYTVSPFSNLRWYKQDTGRGPVSLTILDYAINTKSNGRYT
ATLDADTKQSSLHITASQLSDSASYICVVNRAGGLYIPTFGRGTSLIVHP

Figure 3 continued

SEQ ID NO: 60 mutant alpha chain (a34)

ANQVEQSPQSLIILEGKNVTLQCNYTVSPFSNLRWYKQDTGRGPVSLTILDYAINTKSNGRYT
ATLDADTKQSSLHITASQLSDSASYICVVNRADGSYIPTFGRGTSLIVHP

SEQ ID NO: 61 mutant alpha chain (aWTka)

ANQVEQSPQSLIILEGKNVTLQCNYTVSPFSNLRWYKQDTGRGPVSLTIMTFSENTKSNGRYT
ATLDADTKQSSLHITASQLSDSASYICVVNHSGGSYIPTFGRGTSLIVHP

SEQ ID NO: 62 mutant alpha chain (aM50L)

ANQVEQSPQSLIILEGKNVTLQCNYTVSPFSNLRWYKQDTGRGPVSLTILTFSENTKSNGRYT
ATLDADTKQSSLHITASQLSDSASYICVVNHSGGSYIPTFGRGTSLIVHP

SEQ ID NO: 63 mutant alpha chain (aS95A)

ANQVEQSPQSLIILEGKNVTLQCNYTVSPFSNLRWYKQDTGRGPVSLTIMTFSENTKSNGRYT
ATLDADTKQSSLHITASQLSDSASYICVVNHAGGSYIPTFGRGTSLIVHP

SEQ ID NO: 64 mutant alpha chain (aS98L)

ANQVEQSPQSLIILEGKNVTLQCNYTVSPFSNLRWYKQDTGRGPVSLTIMTFSENTKSNGRYT
ATLDADTKQSSLHITASQLSDSASYICVVNHSGGLYIPTFGRGTSLIVHP

Figure 4

Amino acid sequences of mutated TCR beta chain variable regions. CDRs are underlined and mutations are in bold

SEQ ID NO: 25 mutant beta chain (b1)
DVKVTQSSRYLVKRTGEKVFLECVQD<u>MDHEN</u>MFWYRQDPGLGLRLIYFS<u>YDVKM</u>KEKGDIP
EGYSVSREKKERFSLILESASTNQTSMYLC<u>ASSSDQNSGDPYEQYF</u>GPGTRLTVT

SEQ ID NO: 26 mutant beta chain (b14)
DVKVTQSSRYLVKRTGEKVFLECVQD<u>APLSK</u>MFWYRQDPGLGLRLIYFS<u>YDVKM</u>KEKGDIP
EGYSVSREKKERFSLILESASTNQTSMYLC<u>ASSSDQNSGDPYEQYF</u>GPGTRLTVT

SEQ ID NO: 27 mutant beta chain (b14L)
DVKVTQSSRYLVKRTGEKVFLECVQD<u>APLSK</u>MFWYRQDPGLGLRLIYFS<u>YDVKL</u>KEKGDIP
EGYSVSREKKERFSLILESASTNQTSMYLC<u>ASSSDQNSGDPYEQYF</u>GPGTRLTVT

SEQ ID NO: 28 mutant beta chain (b21)
DVKVTQSSRYLVKRTGEKVFLECVQD<u>MDHEN</u>MFWYRQDPGLGLRLIYFS<u>RFATG</u>KEKGDIP
EGYSVSREKKERFSLILESASTNQTSMYLC<u>ASSSDQNSGDPYEQYF</u>GPGTRLTVT

SEQ ID NO: 29 mutant beta chain (b21L)
DVKVTQSSRYLVKRTGEKVFLECVQD<u>LDHEN</u>MFWYRQDPGLGLRLIYFS<u>RFATG</u>KEKGDIP
EGYSVSREKKERFSLILESASTNQTSMYLC<u>ASSSDQNSGDPYEQYF</u>GPGTRLTVT

SEQ ID NO: 65 mutant beta chain (b41)
DVKVTQSSRYLVKRTGEKVFLECVQD<u>MDHEN</u>MFWYRQDPGLGLRLIYFS<u>RFATG</u>KEKGDIP
EGYSVSREKKERFSLILESASTNQTSMYLC<u>ASSSDQNSGDPYEQYF</u>GPGTRLTVT

SEQ ID NO: 66 mutant beta chain (b42)
DVKVTQSSRYLVKRTGEKVFLECVQD<u>LDHEN</u>MFWYRQDPGLGLRLIYFS<u>YFATG</u>KEKGDIP
EGYSVSREKKERFSLILESASTNQTSMYLC<u>ASSSDQNSGDPYEQYF</u>GPGTRLTVT

Figure 4 continued

SEQ ID NO: 67 mutant beta chain (b43)

DVKVTQSSRYLVKRTGEKVFLECVQD<u>LDHEN</u>MFWYRQDPGLGLRLIYFS<u>RDATG</u>KEKGDIP
EGYSVSREKKERFSLILESASTNQTSMYLCASS<u>SDQN</u>SGDPYEQYFGPGTRLTVT

SEQ ID NO: 68 mutant beta chain (b44)

DVKVTQSSRYLVKRTGEKVFLECVQD<u>LDHEN</u>MFWYRQDPGLGLRLIYFS<u>RFVTG</u>KEKGDIP
EGYSVSREKKERFSLILESASTNQTSMYLCASS<u>SDQN</u>SGDPYEQYFGPGTRLTVT

SEQ ID NO: 69 mutant beta chain (b45)

DVKVTQSSRYLVKRTGEKVFLECVQD<u>LDHEN</u>MFWYRQDPGLGLRLIYFS<u>RFAKG</u>KEKGDIP
EGYSVSREKKERFSLILESASTNQTSMYLCASS<u>SDQN</u>SGDPYEQYFGPGTRLTVT

SEQ ID NO: 70 mutant beta chain (b46)

DVKVTQSSRYLVKRTGEKVFLECVQD<u>LDHEN</u>MFWYRQDPGLGLRLIYFS<u>RFATM</u>KEKGDIP
EGYSVSREKKERFSLILESASTNQTSMYLCASS<u>SDQN</u>SGDPYEQYFGPGTRLTVT

SEQ ID NO: 71 mutant beta chain (b32)

DVKVTQSSRYLVKRTGEKVFLECVQDM<u>PLSK</u>MFWYRQDPGLGLRLIYFS<u>YDVKM</u>KEKGDIP
EGYSVSREKKERFSLILESASTNQTSMYLCASS<u>SDQN</u>SGDPYEQYFGPGTRLTVT

SEQ ID NO: 72 mutant beta chain (b33)

DVKVTQSSRYLVKRTGEKVFLECVQD<u>ADLSK</u>MFWYRQDPGLGLRLIYFS<u>YDVKM</u>KEKGDIP
EGYSVSREKKERFSLILESASTNQTSMYLCASS<u>SDQN</u>SGDPYEQYFGPGTRLTVT

SEQ ID NO: 73 mutant beta chain (b34)

DVKVTQSSRYLVKRTGEKVFLECVQD<u>APHSK</u>MFWYRQDPGLGLRLIYFS<u>YDVKM</u>KEKGDIP
EGYSVSREKKERFSLILESASTNQTSMYLCASS<u>SDQN</u>SGDPYEQYFGPGTRLTVT

SEQ ID NO: 74 mutant beta chain (b35)

DVKVTQSSRYLVKRTGEKVFLECVQD<u>APLEK</u>MFWYRQDPGLGLRLIYFS<u>YDVKM</u>KEKGDIP
EGYSVSREKKERFSLILESASTNQTSMYLCASS<u>SDQN</u>SGDPYEQYFGPGTRLTVT

Figure 4 continued

SEQ ID NO: 75 mutant beta chain (b36)

DVKVTQSSRYLVKRTGEKVFLECVQD<u>APLS</u>NMFWYRQDPGLGLRLIYF<u>SYDVKMKEKGDIP</u>
EGYSVSREKKERFSLILESASTNQTSMYLCASS<u>SDQN</u>SGDPYEQYFGPGTRLTVT

SEQ ID NO: 76 mutant beta chain (b37)

DVKVTQSSRYLVKRTGEKVFLECVQD<u>APLSK</u>MFWYRQDPGLGLRLIYF<u>SYDVKMKEKGDIP</u>
EGYSVSREKKERFSLILESASTNQTSMYLCASS<u>FDQN</u>SGDPYEQYFGPGTRLTVT

SEQ ID NO: 77 mutant beta chain (b38)

DVKVTQSSRYLVKRTGEKVFLECVQD<u>APLSK</u>MFWYRQDPGLGLRLIYF<u>SYDVKMKEKGDIP</u>
EGYSVSREKKERFSLILESASTNQTSMYLCASS<u>SLQN</u>SGDPYEQYFGPGTRLTVT

SEQ ID NO: 78 mutant beta chain (b39)

DVKVTQSSRYLVKRTGEKVFLECVQD<u>APLSK</u>MFWYRQDPGLGLRLIYF<u>SYDVKMKEKGDIP</u>
EGYSVSREKKERFSLILESASTNQTSMYLCASS<u>SDMN</u>SGDPYEQYFGPGTRLTVT

SEQ ID NO: 79 mutant beta chain (b40)

DVKVTQSSRYLVKRTGEKVFLECVQD<u>APLSK</u>MFWYRQDPGLGLRLIYF<u>SYDVKMKEKGDIP</u>
EGYSVSREKKERFSLILESASTNQTSMYLCASS<u>SDQ</u>TSGDPYEQYFGPGTRLTVT

SEQ ID NO: 80 mutant beta chain (bL96D)

DVKVTQSSRYLVKRTGEKVFLECVQD<u>MDHEN</u>MFWYRQDPGLGLRLIYF<u>SYDVKMKEKGDIP</u>
EGYSVSREKKERFSLILESASTNQTSMYLCASS<u>FDMT</u>SGDPYEQYFGPGTRLTVT

SEQ ID NO: 81 mutant beta chain (bM97Q)

DVKVTQSSRYLVKRTGEKVFLECVQD<u>MDHEN</u>MFWYRQDPGLGLRLIYF<u>SYDVKMKEKGDIP</u>
EGYSVSREKKERFSLILESASTNQTSMYLCASS<u>FLQT</u>SGDPYEQYFGPGTRLTVT

Figure 5

Amino acid sequences of alpha chains of TCR anti-CD3 fusion molecules

SEQ ID NO: 38 alpha chain (a19ka)
ANQVEQSPQSLIILEGKNVTLQCNYTVSPFSNLRWYKQDTGRGPVSLTILDYAINTKSNGRYT
ATLDADTKQSSLHITASQLSDSASYICVVNRADGLYIPTFGRGTSLIVHPYIQKPDPAVYQLR
DSKSSDKSVCLFTDFDSQTNVSQSKDSDVYITDKCVLDMRSMDFKSNSAVAWSNKSDFACA
NAFNNSIIPEDT

SEQ ID NO: 39 alpha chain (a13ka)
ANQVEQSPQSLIILEGKNVTLQCNYTVSPFSNLRWYKQDTGRGPVSLTIMTFSENTKSNGRYT
ATLDADTKQSSLHITASQLSDSASYICVVNSANGLYIPTFGRGTSLIVHPYIQKPDPAVYQLR
DSKSSDKSVCLFTDFDSQTNVSQSKDSDVYITDKCVLDMRSMDFKSNSAVAWSNKSDFACA
NAFNNSIIPEDT

SEQ ID NO: 40 alpha chain (a13kaLQ)
ANQVEQSPQSLIILEGKNVTLQCNYTVSPFSNLRWYKQDTGRGPVSLTILTFSENTKSNGRYT
ATLDADTKQSSLHITASQLSDSASYICVVNSAQGLYIPTFGRGTSLIVHPYIQKPDPAVYQLR
DSKSSDKSVCLFTDFDSQTNVSQSKDSDVYITDKCVLDMRSMDFKSNSAVAWSNKSDFACA
NAFNNSIIPEDT

SEQ ID NO: 41 alpha chain (a13kaLS)
ANQVEQSPQSLIILEGKNVTLQCNYTVSPFSNLRWYKQDTGRGPVSLTILTFSENTKSNGRYT
ATLDADTKQSSLHITASQLSDSASYICVVNSASGLYIPTFGRGTSLIVHPYIQKPDPAVYQLR
DSKSSDKSVCLFTDFDSQTNVSQSKDSDVYITDKCVLDMRSMDFKSNSAVAWSNKSDFACA
NAFNNSIIPEDT

Figure 6

Amino acid sequences of beta chains of TCR-anti-CD3 fusion molecules

SEQ ID NO: 42 beta chain (b14). Anti-CD3 scFv shown in bold and linker shown in italics
AIQMTQSPSSLSASVGDRVTITCRASQDIRNYLNWYQQKPGKAPKLLIYYTSRLESGVPSR
FSGSGSGTDYTLTISSLQPEDFATYYCQQGNTLPWTFGQGTKVEIK*GGGGSGGGGSGGGGS*
*GGGGSGGGS*EVQLVESGGGLVQPGGSLRLSCAASGYSFTGYTMNWVRQAPGKGLEWVALIN
PYKGVSTYNQKFKDRFTISVDKSKNTAYLQMNSLRAEDTAVYYCARSGYYGDSDWYFDVWG
QGTLVTVSS*GGGGS*DVKVTQSSRYLVKRTGEKVFLECVQDAPLSKMFWYRQDPGLGLRLIY
FSYDVKMKEKGDIPEGYSVSREKKERFSLILESASTNQTSMYLCASSSDQNSGDPYEQYFG
PGTRLTVTEDLKNVFPPEVAVFEPSEAEISHTQKATLVCLATGFYPDHVELSWWVNGKEVH
SGVCTDPQPLKEQPALNDSRYALSSRLRVSATFWQDPRNHFRCQVQFYGLSENDEWTQDRA
KPVTQIVSAEAWGRAD

SEQ ID NO: 43 beta chain (b14L). Anti-CD3 scFv shown in bold and linker shown in italics
AIQMTQSPSSLSASVGDRVTITCRASQDIRNYLNWYQQKPGKAPKLLIYYTSRLESGVPSR
FSGSGSGTDYTLTISSLQPEDFATYYCQQGNTLPWTFGQGTKVEIK*GGGGSGGGGSGGGGS*
*GGGGSGGGS*EVQLVESGGGLVQPGGSLRLSCAASGYSFTGYTMNWVRQAPGKGLEWVALIN
PYKGVSTYNQKFKDRFTISVDKSKNTAYLQMNSLRAEDTAVYYCARSGYYGDSDWYFDVWG
QGTLVTVSS*GGGGS*DVKVTQSSRYLVKRTGEKVFLECVQDAPLSKMFWYRQDPGLGLRLIY
FSYDVKLKEKGDIPEGYSVSREKKERFSLILESASTNQTSMYLCASSSDQNSGDPYEQYFG
PGTRLTVTEDLKNVFPPEVAVFEPSEAEISHTQKATLVCLATGFYPDHVELSWWVNGKEVH
SGVCTDPQPLKEQPALNDSRYALSSRLRVSATFWQDPRNHFRCQVQFYGLSENDEWTQDRA
KPVTQIVSAEAWGRAD

Figure 6 continued

SEQ ID NO: 44 beta chain (b21). Anti-CD3 scFv shown in bold and linker shown in italics

**AIQMTQSPSSLSASVGDRVTITCRASQDIRNYLNWYQQKPGKAPKLLIYYTSRLESGVPSR
FSGSGSGTDYTLTISSLQPEDFATYYCQQGNTLPWTFGQGTKVEIKGGGGSGGGGSGGGGS
GGGGSGGGSEVQLVESGGGLVQPGGSLRLSCAASGYSFTGYTMNWVRQAPGKGLEWVALIN
PYKGVSTYNQKFKDRFTISVDKSKNTAYLQMNSLRAEDTAVYYCARSGYYGDSDWYFDVWG
QGTLVTVSS*GGGGS*DVKVTQSSRYLVKRTGEKVFLECVQDMDHENMFWYRQDPGLGLRLIY
FSRFATGKEKGDIPEGYSVSREKKERFSLILESASTNQTSMYLCASSSDQNSGDPYEQYFG
PGTRLTVT****EDLKNVFPPEVAVFEPSEAEISHTQKATLVCLATGFYPDHVELSWWVNGKEVH
SGVCTDPQPLKEQPALNDSRYALSSRLRVSATFWQDPRNHFRCQVQFYGLSENDEWTQDRA
KPVTQIVSAEAWGRAD***

SEQ ID NO: 45 beta chain (b21L). Anti-CD3 scFv shown in bold and linker shown in italics

**AIQMTQSPSSLSASVGDRVTITCRASQDIRNYLNWYQQKPGKAPKLLIYYTSRLESGVPSR
FSGSGSGTDYTLTISSLQPEDFATYYCQQGNTLPWTFGQGTKVEIKGGGGSGGGGSGGGGS
GGGGSGGGSEVQLVESGGGLVQPGGSLRLSCAASGYSFTGYTMNWVRQAPGKGLEWVALIN
PYKGVSTYNQKFKDRFTISVDKSKNTAYLQMNSLRAEDTAVYYCARSGYYGDSDWYFDVWG
QGTLVTVSS*GGGGS*DVKVTQSSRYLVKRTGEKVFLECVQDLDHENMFWYRQDPGLGLRLIY
FSRFATGKEKGDIPEGYSVSREKKERFSLILESASTNQTSMYLCASSSDQNSGDPYEQYFG
PGTRLTVT****EDLKNVFPPEVAVFEPSEAEISHTQKATLVCLATGFYPDHVELSWWVNGKEVH
SGVCTDPQPLKEQPALNDSRYALSSRLRVSATFWQDPRNHFRCQVQFYGLSENDEWTQDRA
KPVTQIVSAEAWGRAD***

Figure 7
Potent and specific recognition of antigen positive cancer cells by MAGE A4 TCR-anti-CD3 fusion molecules I
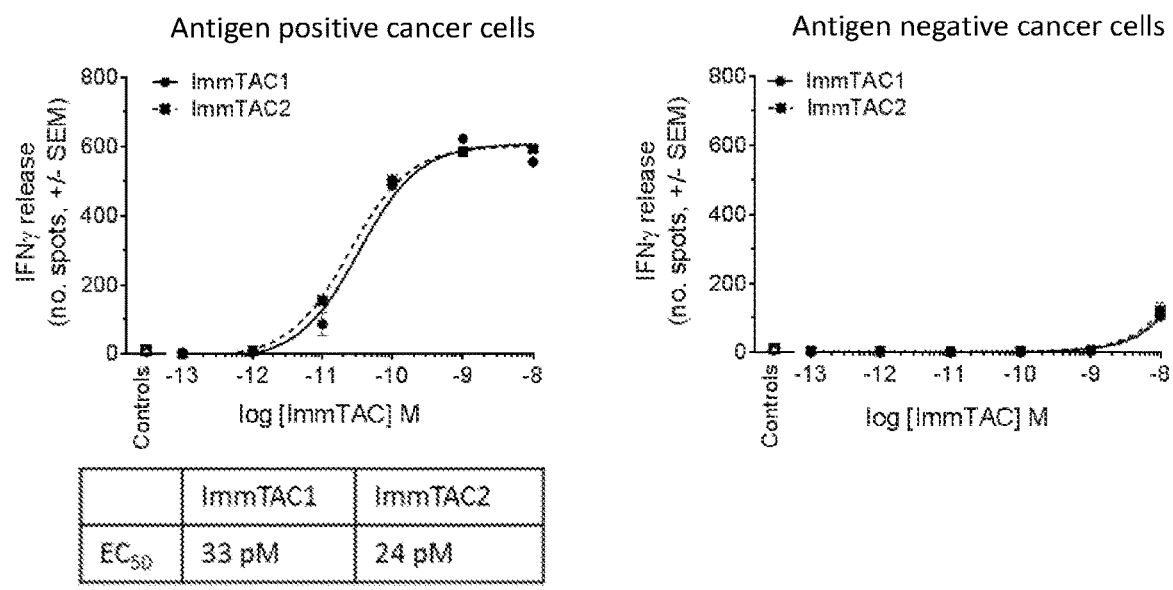
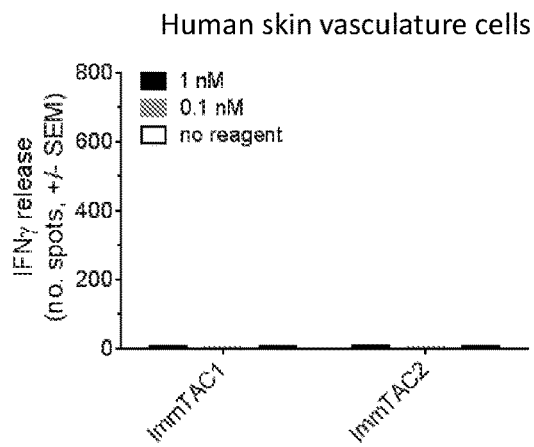

Potent and specific recognition of antigen positive cancer cells by MAGE A4 TCR-anti-CD3 fusion molecules II Further specificity tests for MAGE A4 TCR-anti-CD3 fusion molecules I Further specificity tests for MAGE A4 TCR-anti-CD3 fusion molecules II Figure 11a
Real-time killing response against antigen positive cells (top panel) and antigen negative cells (bottom panel) for MAGE A4 TCR-anti-CD3 fusion molecules
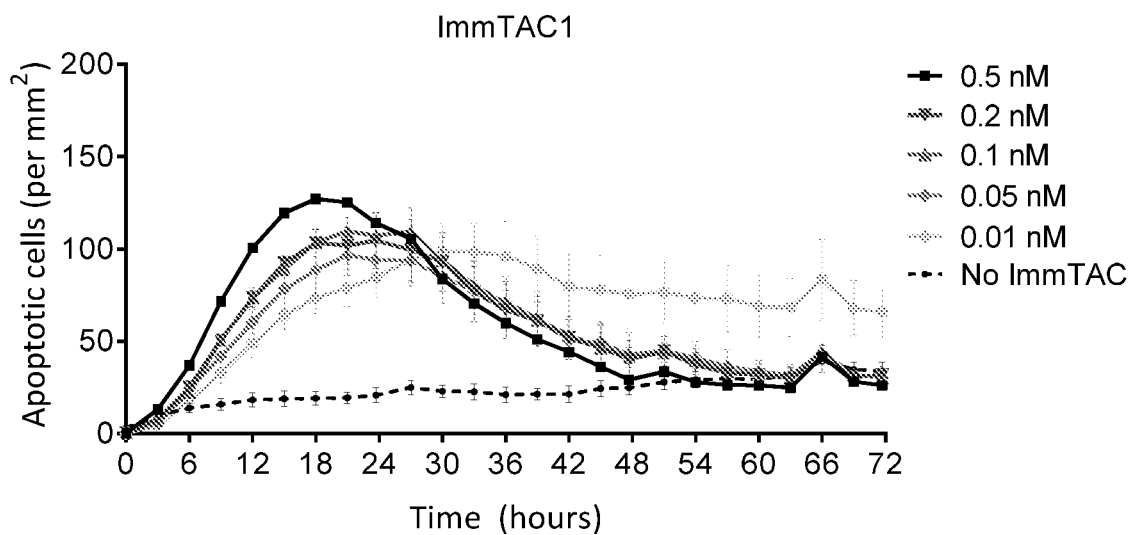
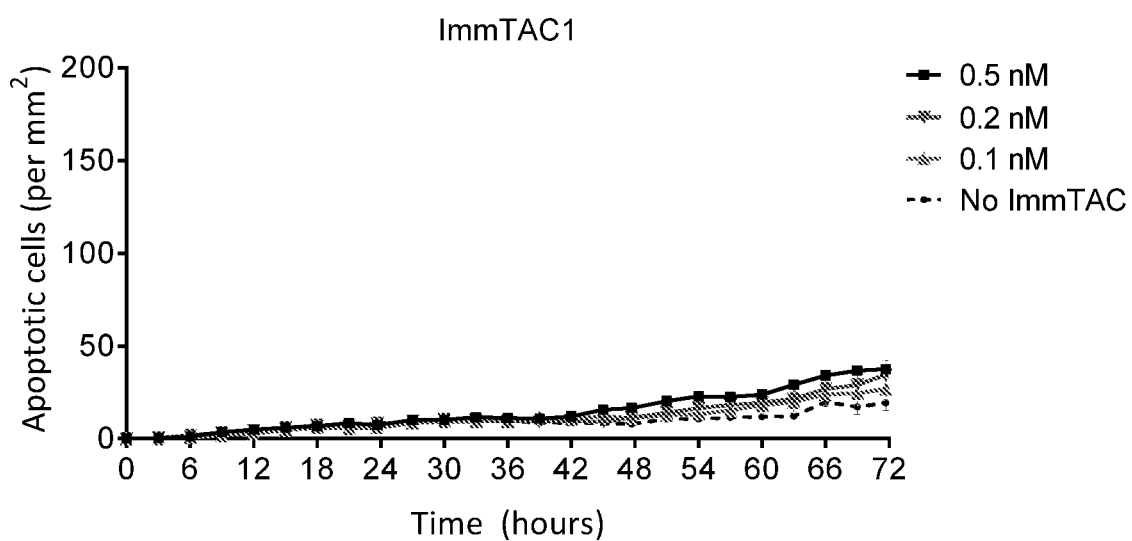

Figure 11b
Real-time killing response against antigen positive cells (top panel) and antigen negative cells (bottom panel) for MAGE A4 TCR-anti-CD3 fusion molecules
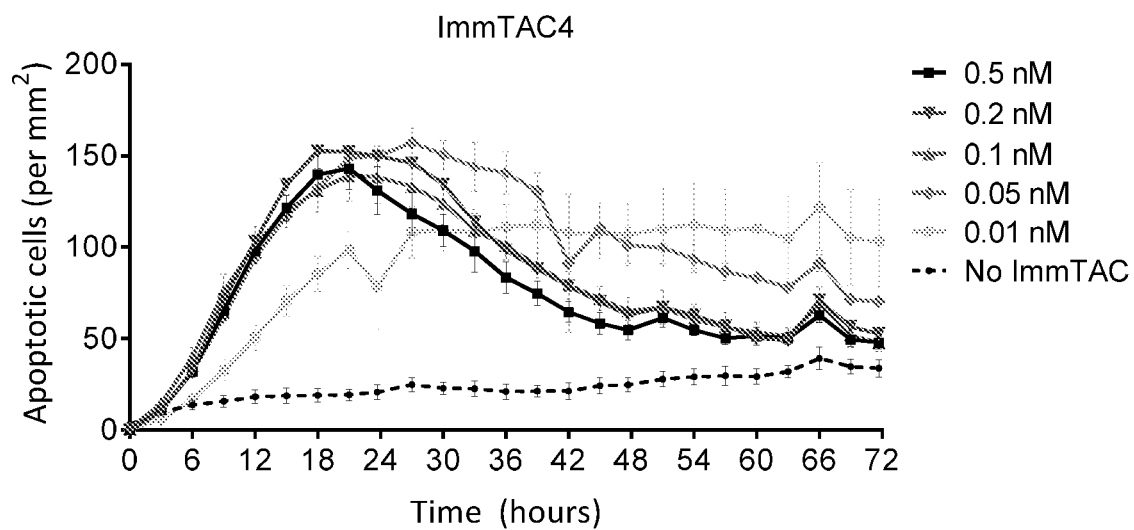
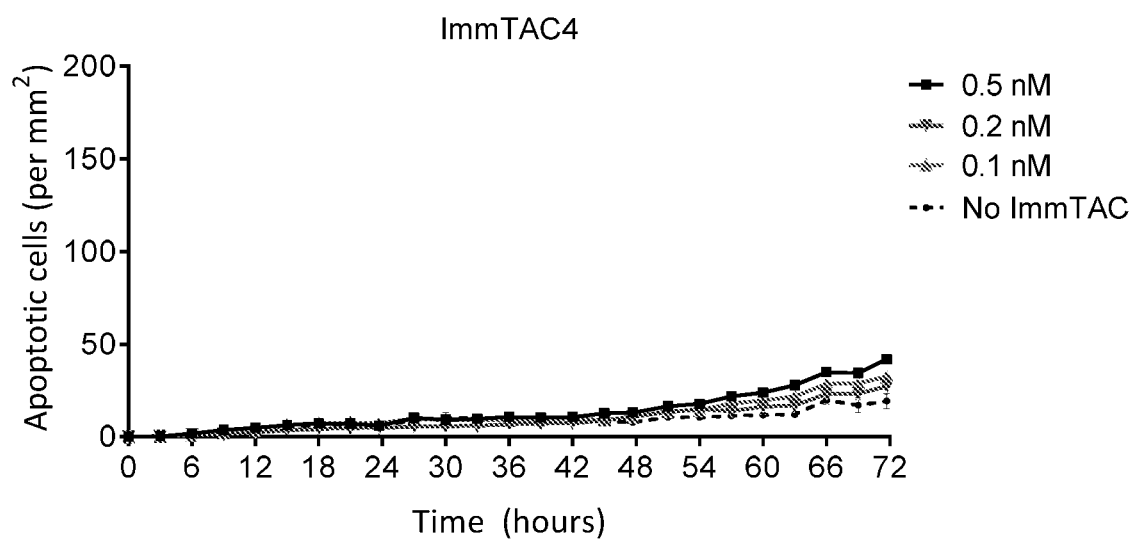

T CELL RECEPTORS

CROSS-REFERENCE TO RELATED APPLICATIONS

This application is the National Stage of International Application No. PCT/GB2017/050985, filed Apr. 7, 2017, which claims the benefit of and priority to Great Britain Patent Application Serial No. 1606009.7, filed on Apr. 8, 2016 the contents of which are incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392047400SUBSEQLIST.TXT, date recorded: May 10, 2021, size: 92 KB).

FIELD OF THE INVENTION

The present invention relates to T cell receptors (TCRs) that bind the HLA-A*02 restricted peptide GVYDGREHTV (SEQ ID NO: 1) derived from the germline cancer antigen MAGE A4. Said TCRs may comprise non-natural mutations within the alpha and/or beta variable domains relative to a native MAGE A4 TCR. The TCRs of the invention are particularly suitable for use as novel immunotherapeutic reagents for the treatment of malignant disease.

BACKGROUND TO THE INVENTION

T cell receptors (TCRs) are naturally expressed by CD4$^+$ and CD8$^+$ T cells. TCRs are designed to recognize short peptide antigens that are displayed on the surface of antigen presenting cells in complex with Major Histocompatibility Complex (MHC) molecules (in humans, MHC molecules are also known as Human Leukocyte Antigens, or HLA) (Davis, et al., (1998), Annu Rev Immunol 16: 523-544.). CD8$^+$ T cells, which are also termed cytotoxic T cells, specifically recognize peptides bound to MHC class I and are generally responsible for finding and mediating the destruction of diseased cells. CD8$^+$ T cells are able to destroy cancerous as well as virally infected cells; however, the affinity of TCRs expressed by cancer specific T cells in the natural repertoire are typically low as a result of thymic selection, meaning that cancerous cells frequently escape detection and destruction. Novel immunotherapeutic approaches aimed at promoting cancer recognition by T cells offer a highly promising strategy for the development of effective anticancer treatments.

MAGE A4 belongs to the MAGE family of germline encoded cancer antigens (De Plaen, et al., (1994), Immunogenetics 40(5): 360-369) and has the Uniprot accession number P43358. Such antigens have been found to be frequently expressed in a variety of cancers, while their expression in normal tissues is limited to adult testes and other immune-privileged sites including placenta. The cancer specific nature of these genes makes them ideal targets for anti-cancer therapeutics. The precise function of MAGE A4 remains unknown but it is believed to play a role in embryonic development. High level expression of MAGE A4 has been reported in tumours of several types including melanoma, carcinomas of the esophagus, the head and neck, the lung, the breast and the bladder (Bergeron, (2009), Int J Cancer 125(6): 1365-1371; Cabezon, et al., (2013), Mol Cell Proteomics 12(2): 381-394; Cuffel, et al., (2011), Int J Cancer 128(11): 2625-2634; Forghanifard, et al., (2011), Cancer Biol Ther 12(3): 191-197; Karimi, et al., (2012), Clin Lung Cancer 13(3): 214-219; Svobodova, et al., (2011), Eur J Cancer 47(3): 460-469). The 10-mer peptide GVYDGREHTV (SEQ ID NO 1) corresponds to amino acids 230-239 of the full length MAGE A4 protein. This peptide binds to HLA-A*02 and the peptide-HLA complex has been shown to stimulate cytotoxic T cells leading to lysis of MAGE A4 positive, HLA-A*02 positive, tumour cells (Duffour, et al., (1999), Eur J Immunol 29(10): 3329-3337 and WO2000020445). The GVYDGREHTV (SEQ ID NO: 1) HLA-A*02 complex therefore provides a useful target antigen for immunotherapeutic intervention.

The identification of particular TCR sequences that bind to the GVYDGREHTV (SEQ ID NO: 1) HLA-A*02 complex with high specificity is advantageous for the development of novel immunotherapies. Therapeutic TCRs may be used, for example, as soluble targeting agents for the purpose of delivering cytotoxic or immune effector agents to the tumour (Lissin, et al., (2013). "High-Affinity Monoclonal T-cell receptor (mTCR) Fusions. Fusion Protein Technologies for Biopharmaceuticals: Applications and Challenges". S. R. Schmidt, Wiley; Boulter, et al., (2003), Protein Eng 16(9): 707-711; Liddy, et al., (2012), Nat Med 8: 980-987), or alternatively they may be used to engineer T cells for adoptive therapy (June, et al., (2014), Cancer Immunol Immunother 63(9): 969-975). However, no such TCR sequences are known in the art, and methods for the identification of TCRs with specificity characteristics amenable to therapeutic use have a high attrition rate and thus do not provide the skilled person with a reasonable expectation of success.

In the first instance, the skilled person needs to identify a suitable starting, or scaffold, sequence. Typically such sequences are obtained from natural sources e.g. from antigen responding T cells extracted from donor blood. Given the rarity of cancer specific T cells in the natural repertoire, it is often necessary to screen many donors, for example 20 or more, before a responding T cell may be found. The screening process may take several weeks or months, and even where a responding T cell is found, it may be unsuitable for immunotherapeutic use. For example, the response may too weak and/or may not be specific for the target antigen, alternatively it may not be possible to generate a clonal T cell population, nor expand or maintain a given T cell line to produce sufficient material to identify the correct TCR chain sequences. Additionally, as TCRs are degenerate and have been predicted to be able to bind approximately one million different HLA-peptides (Wooldridge, et al., (2012), J Biol Chem 287(2): 1168-1177)) it exceptionally hard even for skilled practitioners to be able to determine whether a particular TCR has a specificity profile that would make it eligible for engineering for therapeutic use.

TCR sequences that are suitable as starting, or scaffold, sequences should have a good affinity for the target peptide-HLA complex, for example 200 μM or stronger, demonstrate a high level of target specificity, e.g. relatively weak or no binding to alternative peptide-HLA complexes, be amendable to use in display libraries, such as phage display, and be able to be refolded and purified at a high yield.

TCRs as they exist in nature have weak affinity for target antigen (low micromolar range) compared with antibodies, and TCRs against cancer antigens typically have weaker antigen recognition than viral specific TCRs (Aleksic, et al.

(2012). Eu J Immunol., 42(12), 3174-3179). This weak affinity coupled with HLA down-regulation on cancer cells means that therapeutic TCRs for cancer immunotherapy require engineering to increase their affinity for target antigen and thus generate a more potent response. TCR antigen binding affinities in the nanomolar to picomolar range, with binding half-lives of several hours, are desirable for soluble TCR-based targeting agents. The improved potency generated by high affinity antigen recognition at low epitope numbers is exemplified in FIGS. 1e and 1f of Liddy et al. (Liddy, et al. (2012), Nat Med, 18(6), 980-987). Affinity maturation, typically involves the skilled person having to identify specific mutations and/or combinations of mutations, including but not limited to substitutions, insertions and/or deletions, that can be made to the starting TCR sequence in order to increase the strength of antigen recognition. Methods to identify mutations of a given TCR that confer an affinity enhancement are known in the art for example the use of display libraries (Li et al., (2005) Nat Biotechnol. 23(3):349-354; Holler et al., (2000). Proc Natl Acad Sci USA; 97(10):5387-5392). However, to produce significant increases in the affinity of a given TCR against a given target requires the skilled person to select specific mutations and/or combinations of mutations from a large pool of possible alternatives. The specific mutations and/or combinations of mutations that produce significant increases in affinity are not predictable and there is a high attrition rate. In many cases it may not be possible to achieve significant increases in affinity with a given TCR starting sequence.

The affinity maturation process must also take account of the necessity of maintaining TCR antigen specificity. Increasing the affinity of a TCR for its target antigen brings a substantial risk of revealing cross reactivity with other unintended targets as a result of the inherent degeneracy of TCR antigen recognition (Wooldridge, et al., (2012), J Biol Chem 287(2): 1168-1177; Wilson, et al., (2004), Mol Immunol 40(14-15): 1047-1055; Zhao et al., (2007) J. Immunol, 179; 9, 5845-5854). At a natural level of affinity the recognition of the cross reactive antigen may be too low to produce a response. If a cross reactive antigen is displayed on normal healthy cells, there is a strong possibility of off-target binding in vivo which may manifest in clinical toxicity. Thus, in addition to increasing antigen binding strength, the skilled person must also select mutations and or combinations of mutations that allow the TCR to retain a high specificity for target antigen and demonstrate a good safety profile in preclinical testing. Again such mutations and/or combinations of mutations are not predictable. The attrition rate at this stage is even higher and in many cases may not be achievable at all from a given TCR starting sequence.

The mutations required for high affinity and high specificity should also produce a TCR that is able to be expressed, refolded and purified at a reasonable yield and that is highly stable in a purified form.

Despite the difficulties described above of identifying TCR sequences with suitable characteristics for therapeutic use, the inventors have surprisingly found a TCR sequence that provides an ideal starting point, or scaffold, to produce therapeutic TCRs. Furthermore, the inventors have unexpectedly identified suitable mutations that can be introduced into the alpha and beta variable domains of the scaffold to produce TCR sequences with ideal characteristics for TCR-based targeted immunotherapy of cancers that express MAGE A4.

SUMMARY OF THE INVENTION

In a first aspect, the present invention provides a T cell receptor (TCR) having the property of binding to GVYDGREHTV (SEQ ID NO: 1) in complex with HLA-A*02 and comprising a TCR alpha chain variable domain and/or a TCR beta chain variable domain, the alpha chain variable domain comprising an amino acid sequence that has at least 90% identity to the sequence of amino acid residues 1-113 of SEQ ID NO: 2, and/or the beta chain variable domain comprising an amino acid sequence that has at least 90% identity to the sequence of amino acid residues 1-116 of SEQ ID NO: 3, The alpha chain variable domain may comprise an amino acid sequence that has at least 91%, 92%, 93%, 94%, 95%, 96%, 97%, 98%, 99% or 100% identity to amino acids 1-113 of SEQ ID NO: 2, and/or the beta chain variable domain may comprise an amino acid sequence that has at least 91%, 92%, 93%, 94%, 95%, 96%, 97%, 98%, 99% or 100% identity to amino acids 1-116 of SEQ ID NO: 3.

In a second aspect, the invention provides a TCR that binds to a GVYDGREHTV (SEQ ID NO: 1) HLA-A*02 complex with an affinity greater than 200 µM, wherein: the alpha chain CDRs 1, 2 and 3 comprise SEQ ID NOs 6, 7 and 8 respectively, and/or the beta chain CDRs 1, 2 and 3 comprise SEQ ID NOs 11, 12 and 13 respectively; and/or at least one of the CDRs contains one or more conservative substitutions with respect to SEQ ID NO: 6 to 8 and 11 to 13; and/or at least one of the CDRs contains up to three tolerated substitutions with respect to SEQ ID NO: 6 to 8 and 11 to 13.

The affinity of the TCRs of the invention for the GVYDGREHTV (SEQ ID NO: 1) HLA-A*02 complex may be in the range 200 µM to 1 µM. Preferably said substitutions do not change the binding affinity by more than +/−50%, or more preferably by no more than +/−20%, relative to the non-substituted TCR. Preferably said substitutions do not increase the binding affinity for alternative peptide-HLA complexes.

The scaffold TCR has the following alpha and beta variable chain usage:
Alpha chain: TRAV10*01/TRAJ6*01
Beta chain: TRBV28*01/TRBD1*01/TRBJ2-7*01/
(Note, the term '01' indicates the allelic variant for this sequence, as designated by IMGT nomenclature)
and the following alpha and beta chain CDR3 sequences:

```
Alpha chain:
                                         (SEQ ID NO: 8)
VVNHSGGSYIPTF Beta chain:
                                         (SEQ ID NO: 13)
ASSFLMTSGDPYEQYF
```

The term 'scaffold TCR' or 'starting TCR' is used synonymously in this application with the terms Wild type TCR' or 'WT TCR' or 'non-mutated TCR' or 'native TCR', or 'parental TCR' to mean a TCR having an alpha chain variable comprising residues 1-113 of SEQ ID NO: 2 and a beta chain variable domain comprising residues 1-116 of SEQ ID NO: 3. The constant domain of the WT TCR may be full length, or may be truncated and/or mutated to produce a soluble TCR. In either case cysteine substitutions may be introduced into the TRAC and TRBC regions such that a non-native interchain disulphide bond can be formed. Suitable positions for the location of said cysteine substitutions are described in WO03020763. FIG. 2 of the accompanying drawings shows the extracellular sequences of the wild type TCR alpha and beta chains respectively, in soluble format. SEQ ID NO: 4 is identical to the native alpha chain extracellular sequence SEQ ID NO: 2 except that the cysteine at position 48 of the constant domain has been replaced with threonine. Likewise SEQ ID NO: 5 is identical to the native beta chain extracellular sequence SEQ ID NO: 3 except that cysteine at position 57 of the constant domain has been replaced with serine, cysteine at position 75 of the constant domain has been replaced with alanine, and asparagine at position 89 of the constant domain has been replaced with aspartic acid. The soluble wild-type TCR may be used to provide a reference against which the binding profile of mutated TCRs of the invention may be compared.

The TCR sequences defined herein are described with reference to IMGT nomenclature which is widely known and accessible to those working in the TCR field. For example, see: LeFranc and LeFranc, (2001). "T cell Receptor Factsbook", Academic Press; Lefranc, (2011), Cold Spring Harb Protoc 2011(6): 595-603; Lefranc, (2001), Curr Protoc Immunol Appendix 1: Appendix 100; and Lefranc, (2003), Leukemia 17(1): 260-266. Briefly, αβ TCRs consist of two disulphide linked chains. Each chain (alpha and beta) is generally regarded as having two domains, namely a variable and a constant domain. A short joining region connects the variable and constant domains and is typically considered part of the alpha variable region. Additionally, the beta chain usually contains a short diversity region next to the joining region, which is also typically considered part of the beta variable region.

The variable domain of each chain is located N-terminally and comprises three Complementarity Determining Regions (CDRs) embedded in a framework sequence. The CDRs comprise the recognition site for peptide-MHC binding. There are several genes coding for alpha chain variable (Vα) regions and several genes coding for beta chain variable (Vβ) regions, which are distinguished by their framework, CDR1 and CDR2 sequences, and by a partly defined CDR3 sequence. The Vα and Vβ genes are referred to in IMGT nomenclature by the prefix TRAV and TRBV respectively (Folch and Lefranc, (2000), Exp Clin Immunogenet 17(1): 42-54; Scaviner and Lefranc, (2000), Exp Clin Immunogenet 17(2): 83-96; LeFranc and LeFranc, (2001), "T cell Receptor Factsbook", Academic Press). Likewise there are several joining or J genes, termed TRAJ or TRBJ, for the alpha and beta chain respectively, and for the beta chain, a diversity or D gene termed TRBD (Folch and Lefranc, (2000), Exp Clin Immunogenet 17(2): 107-114; Scaviner and Lefranc, (2000), Exp Clin Immunogenet 17(2): 97-106; LeFranc and LeFranc, (2001), "T cell Receptor Factsbook", Academic Press). The huge diversity of T cell receptor chains results from combinatorial rearrangements between the various V, J and D genes, which include allelic variants, and junctional diversity (Arstila, et al., (1999), Science 286(5441): 958-961; Robins et al., (2009), Blood 114(19): 4099-4107.) The constant, or C, regions of TCR alpha and beta chains are referred to as TRAC and TRBC respectively (Lefranc, (2001), Curr Protoc Immunol Appendix 1: Appendix 1O).

The alpha chain variable domain of the first or second aspect may have a mutation in at least one of the following positions with reference to the numbering of residues 1-113 of SEQ ID NO: 2: M50, T51, F52, S53, E54, H94, S95, G96, S98. The mutations may be selected from the following amino acids with reference to the numbering of residues 1-113 of SEQ ID NO: 2:

TABLE 1

| Residue no. | |
|---|---|
| M50 | L |
| T51 | D |
| F52 | Y |
| S53 | A |
| E54 | I |
| H94 | S, R |
| S95 | A |
| G96 | N, D, S, Q |
| S98 | L |

Additionally or alternatively, the beta chain variable domain of the first or second aspect may have a mutation in at least one of the following positions with reference to the numbering of residues 1-116 of SEQ ID NO: 3: M27; D28; H29, E30, N31, Y50, D51, V52, K53, M54, F95, L96, M97, T98. The mutations may be selected from the following amino acids with reference to the numbering of residues 1-116 of SEQ ID NO: 3:

TABLE 2

| Residue no. | |
|---|---|
| M27 | A, L |
| D28 | P |
| H29 | L |
| E30 | S |
| N31 | K |
| Y50 | R |
| D51 | F |
| V52 | A |
| K53 | T |
| M54 | G, L |
| F95 | S |
| L96 | D |
| M97 | Q |
| T98 | N |

The alpha chain variable domain may have 1, 2, 3, 4, 5, 6, 7, 8 or 9 of the mutations shown in Table 1 and/or the beta chain variable domain may have 1, 2, 3, 4, 5, 6, 7, 8, 9 or 10 of the mutations shown in Table 2

The alpha chain variable domain may have at least one of the following groups of mutations:
  Group 1: M50L, T51 D, F52Y, S53A, E54I
  Group 2: H94S, S95A, G96N, S98L
  Group 3: H94R S95A, G96D, S98L
  Group 4: M50L, T51 D, F52Y, S53A, E54I, H94R S95A, G96D, S98L
  Group 5: M50L, H94S, S95A, G96S, S98L
  Group 6: M50L, H94S, S95A, G96Q, S98L
  and/or the beta chain variable domain may have at least one of the following groups of mutations:
  Group 1: M27A, D28P, H29L, E30S, N31 K F95S, L96D, M97Q, T98N
  Group 2: Y50R, D51F, V52A, K53T, M54G, F95S, L96D, M97Q, T98N
  Group 3: F95S, L96D, M97Q, T98N
  Group 4: M27L, Y50R, D51F, V52A, K53T, M54G, F95S, L96D, M97Q, T98N
  Group 5: M27A, D28P, H29L, E30S, N31 K, M54L, F95S, L96D, M97Q, T98N For example, the alpha chain variable domain may have Group 4 mutations and the beta chain variable domain may have Group 1 mutations; the alpha chain variable domain may have Group 4 mutations and the beta chain variable domain may have Group 5 mutations; the alpha chain variable domain may have Group 2 mutations and the beta chain variable domain may have Group 2 mutations; the alpha chain variable domain may have Group 6 mutations and the beta chain variable domain may have Group 4 mutations; the alpha chain variable domain may have Group 5 mutations and the beta chain variable domain may have Group 4 mutations.

Mutations may additionally or alternatively be made outside of the CDRs; such mutations may improve binding, and/or specificity, and/or stability, and/or the yield of a purified soluble form of the TCR. For example, the TCR of the invention may additionally or alternatively comprise an alpha chain variable domain that has the following mutations with reference to the numbering of residues 1-113 of SEQ ID NO: 2:

TABLE 3

| Residue no. | |
|---|---|
| K1 | A |
| C19 | V |

In the alpha chain variable domain the sequence of amino acid residues 27-32, 50-56 and 91-103 may be selected from the following:

TABLE 4

| Residues 27-32 (CDR1) | Residues 50-56 (CRD2) | Residues 91-103 (CDR3) |
|---|---|---|
| VSPFSN | MTFSENT | VVNHSGGSYIPTF |
| VSPFSN | MTFSENT | VVNSANGLYIPTF |
| VSPFSN | MTFSENT | VVNRADGLYIPTF |
| VSPFSN | LDYAINT | VVNHSGGSYIPTF |
| VSPFSN | LDYAINT | VVNRADGLYIPTF |
| VSPFSN | LTFSENT | VVNSASGLYIPTF |
| VSPFSN | LTFSENT | VVNSAQGLYIPTF |

The TCR alpha chain variable domain may comprise an amino acid sequence that has at least 90% 91%, 92%, 93%, 94%, 95%, 96%, 97%, 98%, 99% or 100% identity to any one of SEQ ID NOs: 16-24 or 46-64.

In the beta chain variable domain the sequence of amino acid residues 27-31, 49-54 and 92-107 may be selected from the following:

TABLE 5

| Residues 27-31 (CDR1) | Residues 49-54 (CDR2) | Residues 92-107 (CDR3) |
|---|---|---|
| MDHEN | SYDVKM | ASSFLMTSGDPYEQYF |
| MDHEN | SRFATG | ASSSDQNSGDPYEQYF |
| MDHEN | SYDVKM | ASSSDQNSGDPYEQYF |
| LDHEN | SRFATG | ASSSDQNSGDPYEQYF |
| APLSK | SYDVKM | ASSSDQNSGDPYEQYF |
| APLSK | SYDVKL | ASSSDQNSGDPYEQYF |

The TCR beta chain variable domain may comprise an amino acid sequence that has at least 90% 91%, 92%, 93%, 94%, 95%, 96%, 97%, 98%, 99% or 100% identity to any one of SEQ ID NOs: 25-29 or 65-81.

The alpha chain variable domain sequence of amino acid residues 27-32, 50-56 and 91-103 and the beta chain variable domain sequence of amino acid residues 27-31, 49-54 and 92-107 may be selected from the following

TABLE 6

| Alpha chain | | | Beta chain | | |
|---|---|---|---|---|---|
| 27-32 | 50-56 | 91.103 | 27-31 | 49-54 | 92-107 |
| VSPFSN | LDYAINT | VVNRADGLYIPTF | APLSK | SYDVKM | ASSSDQNSGDPYEQYF |
| VSPFSN | LDYAINT | VVNRADGLYIPTF | APLSK | SYDVKL | ASSSDQNSGDPYEQYF |
| VSPFSN | MTFSENT | VVNSANGLYIPTF | MDHEN | SRFATG | ASSSDQNSGDPYEQYF |
| VSPFSN | LTFSENT | VVNSAQGLYIPTF | LDHEN | SRFATG | ASSSDQNSGDPYEQYF |
| VSPFSN | LTFSENT | VVNSASGLYIPTF | LDHEN | SRFATG | ASSSDQNSGDPYEQYF |

The alpha chain variable domain may comprise the amino acid sequence of any one of SEQ ID NOS: 16 to 24 or 46-64 and/or the beta chain variable domain may comprise the amino acid sequence of any one of SEQ ID NOS: 25 to 29 or 65-81.

For example, the alpha chain variable domain may comprise the amino acid sequence of SEQ ID NO: 22 and the beta chain variable domain may comprise the amino acid sequence of SEQ ID NO: 26; the alpha chain variable domain may comprise the amino acid sequence of SEQ ID NO: 22 and the beta chain variable domain may comprise the amino acid sequence of SEQ ID NO: 27; the alpha chain variable domain may comprise the amino acid sequence of SEQ ID NO: 20 and the beta chain variable domain may comprise the amino acid sequence of SEQ ID NO: 28; the alpha chain variable domain may comprise the amino acid sequence of SEQ ID NO: 24 and the beta chain variable domain may comprise the amino acid sequence of SEQ ID NO: 29; the alpha chain variable domain may comprise the amino acid sequence of SEQ ID NO: 23 and the beta chain variable domain may comprise the amino acid sequence of SEQ ID NO: 29.

The TCR of the invention may be an alpha-beta heterodimer, having an alpha chain TRAC constant domain sequence and a beta chain TRBC1 or TRBC2 constant domain sequence.

The TCR of the invention may be in single chain format including but not limited to Vα-L-Vβ, Vβ-L-Vα, Vα-Cα-L-Vβ, Vα-L-Vβ-Cα, Vα-Cα-L-Vβ-Cα, wherein Vα and Vβ are TCR α and β variable regions respectively, Cα and Cβ are TCR α and β constant regions respectively, and L is a linker sequence.

The TCR of the invention may be associated with a detectable label, a therapeutic agent or a PK modifying moiety.

The TCR of the invention may comprise an anti-CD3 antibody covalently linked to the C- or N-terminus of the alpha or beta chain of the TCR. Such a TCR may comprise an alpha chain variable domain selected from any one of SEQ ID NOS: 16-24 or 46-64 and a beta chain variable domain selected from any one of SEQ ID NOS: 25-29 or 65-81 fused to an anti-CD3 antibody. The beta chain may be linked to the anti-CD3 antibody sequence via a linker sequence; the linker sequence may be selected from the group consisting of GGGGS (SEQ ID NO: 30), GGGSG (SEQ ID NO: 31), GGSGG (SEQ ID NO: 32), GSGGG (SEQ ID NO: 33), GSGGGP (SEQ ID NO: 34), GGEPS (SEQ ID NO: 35), GGEGGGP (SEQ ID NO: 36), and GGEGGGSEGGGS (SEQ ID NO: 37).

Preferred embodiments of TCR anti-CD3 fusions comprise an alpha chain amino acid sequence selected from SEQ ID NO: 38-41, or a sequence that has at least 90%, 91%, 92%, 93%, 94%, 95%, 96%, 97%, 98%, 99% or 100% identity to the amino acid sequence set forth in SEQ ID NO: 38-41, and a beta chain amino acid sequence selected from SEQ ID NO: 42-45, or a sequence that has at least 90%, 91%, 92%, 93%, 94%, 95%, 96%, 97%, 98%, 99% or 100% identity, to the amino acid sequence set forth in SEQ ID NO: 42-45.

The TCR of the invention may be included in a library of particles. For such purposes the TCR may be displayed on the surface of a bacteriophage, yeast cell, mammalian cell or ribosome, for example. The TCR may be isolated, cell free and/or soluble, i.e. it may not be a TCR that occurs in its natural state within a T-cell within a human body.

TCRs of the invention may be non-naturally occurring and/or purified and/or engineered. TCRs of the invention may have more than one mutation present in the alpha chain variable domain and/or the beta chain variable domain relative to the native MAGE A4 TCR.

The TCR of the invention may comprise an alpha chain framework 2 (FR2) region and an alpha chain framework 3 (FR3) region, wherein the FR2 and FR3 regions comprise SEQ ID NO: 9 and 10 respectively, and/or contain one or more, for example one, two or three, conservative substitutions and/or up to three tolerated substitutions.

The TCR of the invention may comprise a beta chain FR2 region and a beta chain FR3 region, wherein the FR2 and FR3 regions comprise SEQ ID NOs:14 and 15 respectively, and/or contain one or more, for example one, two or three, conservative substitutions and/or up to three tolerated substitutions.

The TCR of the invention may comprise amino acids 1-113 of SEQ ID NO: 2 and/or amino acids 1-116 of SEQ ID NO: 3, which each may contain one or more conservative substitutions and/or up to three tolerated mutations and/or one or more of the mutations set out in tables 1, 2 and 3.

"Engineered TCR" and "mutant TCR" are used synonymously herein to mean a TCR which has one or more mutations introduced relative to the native MAGE A4 TCR, in particular in the alpha chain variable domain and/or the beta chain variable domain thereof. Mutation(s) typically improve the binding affinity of the TCR to the GVYDGREHTV (SEQ ID NO: 1) HLA-A*02 complex, but may additionally or alternatively confer other advantages such as improved stability in an isolated form and improved specificity. Mutations at one or more positions may additionally or alternatively affect the interaction of an adjacent position with the cognate pMHC complex, for example by enabling a more favourable angle for interaction. To improve binding of the TCR to the GVYDGREHTV (SEQ ID NO: 1) HLA-A*02 complex, mutations are preferably made within one or more of the CDR regions.

In certain embodiments, there are 1, 2, 3, 4, 5, 6, 7, 8 or 9 mutations in alpha chain CDRs, for example 4, 5 or 9 mutations, and/or 1, 2, 3, 4, 5, 6, 7, 8, 9 or 10 mutations in the beta chain CDRs, for example 4, 9 or 10 mutations.

In some embodiments, the α chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues 1-113 of SEQ ID NO: 2, provided that the α chain variable domain has at least one of the mutations outlined above, for example in Table 1 or Table 3. In some embodiments, the β chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues 1-116 of SEQ ID NO: 3, provided that the β chain variable domain has at least one of the mutations outlined above, for example in Table 2.

Mutations to a parental (or wild type) TCR may include those that are able to increase the binding affinity ($k_D$ and/or binding half life) of the TCR to GVYDGREHTV (SEQ ID NO: 1). Mutations may include those that are able to reduce the amount of non-specific binding, i.e. reduce binding to antigens in addition to binding to GVYDGREHTV (SEQ ID NO: 1). Mutations may include those that increase efficacy of folding and/or manufacture. Some mutations may contribute to each of these characteristics, others may contribute to affinity but not to specificity, for example, or to specificity but not to affinity etc.

Within the scope of the invention are phenotypically silent variants of any TCR of the invention disclosed herein. As used herein the term "phenotypically silent variants" is understood to refer to a TCR which incorporates one or more further amino acid changes, including substitutions, insertions and deletions, in addition to those set out above, which TCR has a similar phenotype to the corresponding TCR without said change(s). For the purposes of this application, TCR phenotype comprises antigen binding affinity ($K_D$ and/or binding half-life) and antigen specificity. A phenotypically silent variant may have a $K_D$ and/or binding half-life for the GVYDGREHTV (SEQ ID NO: 1) HLA-A*02 complex within 50%, or more preferably within 20%, of the measured $K_D$ and/or binding half-life of the corresponding TCR without said change(s), when measured under identical conditions (for example at 25° C. and/or on the same SPR chip). Suitable conditions are further provided in Example 3. Antigen specificity is further defined below. As is known to those skilled in the art, it may be possible to produce TCRs that incorporate changes in the variable domains thereof compared to those detailed above without altering the affinity of the interaction with the GVYDGREHTV (SEQ ID NO: 1) HLA-A*02 complex. In particular, such silent mutations may be incorporated within parts of the sequence that are known not to be directly involved in antigen binding (e.g. the CDRs, or parts of the CDRs that do not contact the peptide antigen). Such trivial variants are included in the scope of this invention.

Phenotypically silent variants may contain one or more conservative substitutions and/or one or more tolerated substitutions. Tolerated and conservative substitutions may result in a change in the $K_D$ and/or binding half-life for the GVYDGREHTV (SEQ ID NO: 1) HLA-A*02 complex within 50%, or more preferably within 20%, even more preferable within 10%, of the measured $K_D$ and/or binding half-life of the corresponding TCR without said conservative and/or tolerated substitution(s), when measured under identical conditions (for example at 25° C. and/or the same SPR chip), provided that the change in $K_D$ does not result in the affinity being less than (i.e. weaker than) 200 μm. By tolerated substitutions it is meant those substitutions which do not fall under the definition of conservative as provided below but are nonetheless phenotypically silent.

The TCRs of the present invention may include one or more conservative substitutions which have a similar amino acid sequence and/or which retain the same function (i.e. are phenotypically silent as defined above). The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). It should be appreciated that amino acid substitutions within the scope of the present invention can be made using naturally occurring or non-naturally occurring amino acids. For example, it is contemplated herein that the methyl group on an alanine may be replaced with an ethyl group, and/or that minor changes may be made to the peptide backbone. Whether or not natural or synthetic amino acids are used, it is preferred that only L-amino acids are present.

Substitutions of this nature are often referred to as "conservative" or "semi-conservative" amino acid substitutions. The present invention therefore extends to use of a TCR comprising an amino acid sequence described above but with one or more conservative substitutions and or one or more tolerated substitutions in the sequence, such that the amino acid sequence of the TCR has at least 90% identity, such as 90%, 91%, 92%, 93%, 94%, 95%, 96%, 97%, 98%, 99% or 100% identity, to the TCR comprising amino acids 1-113 of SEQ ID NOs: 2, 16-24 or 46-64, and/or amino acids 1-116 of SEQ ID NOs: 3, 25-29 or 65-81.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules. BLAST protein searches can be performed with the XBLAST program, score=50, wordlength=3 to obtain amino acid sequences homologous to protein molecules for use in the invention. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Mutations, including conservation and tolerated substitutions, insertions and deletions, may be introduced into the sequences provided using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning— A Laboratory Manual ($3^{rd}$ Ed.) CSHL Press. Further information on ligation independent cloning (LIC) procedures can be found in Rashtchian, (1995) Curr Opin Biotechnol 6(1): 30-6. The TCR sequences provided by the invention may be obtained from solid state synthesis, or any other appropriate method known in the art.

The TCRs of the invention have the property of binding the GVYDGREHTV (SEQ ID NO: 1) HLA-A*02 complex. TCRs of the invention have been found to strongly recognise this epitope relative to other, irrelevant epitopes, and are thus particularly suitable as targeting vectors for delivery of therapeutic agents or detectable labels to cells and tissues displaying those epitopes. Specificity in the context of TCRs of the invention relates to their ability to recognise HLA-A*02 target cells that are antigen positive, whilst having minimal ability to recognise HLA-A*02 target cells that are antigen negative.

Specificity can be measured in vitro, for example, in cellular assays such as those described in Example 6. To test specificity the TCRs may be in soluble form and/or may fused to an immune effector, and/or may be expressed on the surface of cells, such as T cells. Recognition may be determined by measuring the level of T cell activation in the presence of a TCR of the invention and target cells. Minimal recognition of antigen negative target cells is defined as a level of T cell activation of less than 20%, preferably less than 10%, preferably less than 5%, and more preferably less than 1%, of the level produced in the presence of antigen positive target cells, when measured under the same conditions and at a therapeutically relevant TCR concentration. For soluble TCRs of the invention a therapeutically relevant concentration may be defined as a TCR concentration of $10^{-9}$ M or below, and/or a concentration of up to 100, preferably up to 1000, fold greater than the corresponding EC50 value. Antigen positive cells may be obtained by peptide-pulsing using a suitable peptide concentration to obtain a level of antigen presentation comparable to cancer cells (for example, $10^{-9}$ M peptide, as described in Bossi et al., (2013) Oncoimmunol. 1; 2 (11):e26840) or, they may naturally present said peptide. Preferably, both antigen positive and antigen negative cells are human cells. Preferably antigen positive cells are human cancer cells. Antigen negative cells preferably include those derived from healthy human tissues.

Specificity may additionally, or alternatively, relate to the ability of a TCR to bind to GVYDGREHTV (SEQ ID NO: 1) HLA-A*02 complex and not to a panel of alternative peptide-HLA complexes. This may, for example, be determined by the Biacore method of Example 3. Said panel may contain at least 5, and preferably at least 10, alternative peptide-HLA-A*02 complexes. The alternative peptides may share a low level of sequence identity with SEQ ID NO: 1 and may be naturally presented. Alternative peptides may be derived from proteins expressed in healthy human tissues. Binding to GVYDGREHTV (SEQ ID NO: 1)—HLA-A*02 complex may be at least 2 fold greater than to other naturally-presented peptide HLA complexes, more preferably at least 10 fold, or at least 50 fold or at least 100 fold greater, even more preferably at least 400 fold greater.

An alternative or additional approach to determine TCR specificity may be to identify the peptide recognition motif of the TCR using sequential mutagenesis, e.g. alanine scanning. Residues that form part of the binding motif are those that are not permissible to substitution. None permissible substitutions may be defined as those peptide positions in which the binding affinity of the TCR is reduced by at least 50%, or preferably at least 80% relative to the binding affinity for the non-mutated peptide. Such an approach is further described in Cameron et al., (2013), Sci Transl Med. 2013 Aug. 7; 5 (197): 197ra103 and WO2014096803. TCR specificity in this case may be determined by identifying alternative motif containing peptides, particularly alternative motif containing peptides in the human proteome, and testing these peptides for binding to the TCR. Binding of the TCR to one or more alternative peptides may indicate a lack of specificity. In this case further testing of TCR specificity via cellular assays may be required.

As is known to those skilled in the art peptides derived from MAGE family members may share a high level of sequence identity with peptides derived from other MAGE family members. For example, there are peptides derived from MAGE-A8 and MAGE-B2 that differ by only two residues from SEQ ID NO 1 (GVYDGREHTV). Said peptides and cells expressing said MAGE family members may be excluded from the definition of specificity provided above, particularly if said MAGE family members are known to be cancer antigens, such as MAGE-A8 and MAGE-B2. TCRs of the invention may therefore recognise peptides with high percentage sequence identity that are derived from other MAGE family members, including MAGE-A8 and MAGE-B2 and displayed in the context of HLA A*02. Recognition of said peptides by TCRs of the invention may be at a similar or lower level than recognition of GVYDGREHTV (SEQ ID NO: 1) HLA-A*02.

Certain TCRs of the invention may have an ideal safety profile for use as therapeutic reagents. In this case the TCRs may be in soluble form and may preferably be fused to an immune effector. An ideal safety profile means that in addition to demonstrating good specificity, the TCRs of the invention may have passed further preclinical safety tests. Examples of such tests include whole blood assays to confirm minimal cytokine release in the presence of whole blood and thus low risk of causing a potential cytokine release syndrome in vivo, and alloreactivity tests to confirm low potential for recognition of alternative HLA types.

Certain soluble TCRs of the invention may be amenable to high yield purification. High yield means greater than 1%, or more preferably greater than 10%, or higher yield.

TCRs of the invention may have a $K_D$ for the GVYDGREHTV (SEQ ID NO: 1)—HLA-A*02 complex of greater than (i.e. stronger than) 200 μM, for example between 1 pM and 200 μM. Certain TCRs of the invention may have a $K_D$ for the complex of from about 1 pM to about 400 nM, from about 1 pM to about 200 pM, from about 1 pM to about 100 pM. Certain TCRs of the invention may have a $K_D$ for the complex of about 20-80 pM. TCRs of the invention may have a binding half-life (T½) for the complex in the range of from about 1 sec to about 60 h, from 1 min to about 60 h, from about 20 min to about 50 h, or from about 2 h to about 35 h. Certain TCRs of the invention may have a T½ for the complex from about 8 h to 35 h. TCRs that are for use as soluble therapeutics and/or diagnostics when coupled to a detectable label or therapeutic agent preferably have a $K_D$ for the complex of from about 1 pM to about 100 pM, or from about 20 pM to about 80 pM, and/or a binding half-life for the complex of from about 2 h to 60 h, or from about 8 h to about 35 h. Certain TCRs of the invention may be suitable for adoptive therapy applications; such TCRs may have a $K_D$ for the complex of from about 50 nM to about 200 μM, or from about 100 nM to about 1 μM and/or a binding half-life for the complex of from about 3 sec to about 12 min.

Certain preferred TCRs are able to generate a highly potent T cell response in vitro against antigen positive cells, in particular those cells presenting low levels of antigen typical of cancer cells (i.e. around 50 antigens per cell (Bossi et al., (2013) Oncoimmunol. 1; 2 (11):e26840; Purbhoo et al.,(2006). J Immunol 176(12): 7308-7316.)). Such TCRs may be in soluble form and linked to an immune effector such as an anti-CD3 antibody. The T cell response that is measured may be the release of T cell activation markers such as Interferon γ or Granzyme B, or cell killing, or other measure of T cell activation. Preferably a highly potent response is one with EC50 value in the pM range, for example 100 pM or lower.

Certain preferred TCRs of the invention have a binding affinity for, and/or a binding half-life for, the GVYDGREHTV (SEQ ID NO: 1)—HLA-A*02 complex substantially higher than that of the native TCR. Increasing the binding affinity of a native TCR often reduces the specificity of the TCR for its peptide-MHC ligand, and this is demonstrated in Zhao et al., (2007) J. Immunol, 179:9, 5845-5854. However, such TCRs of the invention remain specific for the GVYDGREHTV (SEQ ID NO: 1)-HLA-A*02 complex, despite having substantially higher binding affinity than the native TCR.

Binding affinity (inversely proportional to the equilibrium constant $K_D$) and binding half-life (expressed as T½) can be determined using the Surface Plasmon Resonance (BIAcore) and/or the Octet method of Example 3 herein. It will be appreciated that doubling the affinity of a TCR results in halving the $K_D$. T½ is calculated as ln2 divided by the off-rate ($k_{off}$). Therefore, doubling of T½ results in a halving in $k_{off}$. $K_D$ and $k_{off}$ values for TCRs are usually measured for soluble forms of the TCR, i.e. those forms which are truncated to remove cytoplasmic and transmembrane domain residues. Preferably the binding affinity or binding half-life of a given TCR is measured several times, for example 3 or more times, using the same assay protocol and an average of the results is taken.

For use as a targeting agent for delivering therapeutic agents to the antigen presenting cell the TCR may be in soluble form (i.e. having no transmembrane or cytoplasmic domains). For stability, TCRs of the invention, and preferably soluble αβ heterodimeric TCRs, may have an introduced disulphide bond between residues of the respective constant domains, as described, for example, in WO 03/020763. One or both of the extracellular constant domains present in an αβ heterodimer of the invention may be truncated at the C terminus or C termini, for example by up to 15, or up to 10 or up to 8 or fewer amino acids. The C terminus of the alpha chain extracellular constant domain may be truncated by 8 amino acids. One or both of the extracellular constant domains may contain one or more mutations. The alpha chain extracellular constant may have an asparagine (N) or a lysine (K) residue at position 4 due to a natural polymorphism. For use in adoptive therapy, an αβ heterodimeric TCR may, for example, be transfected as full length chains having both cytoplasmic and transmembrane domains. TCRs for use in adoptive therapy may contain a disulphide bond corresponding to that found in nature between the respective alpha and beta constant domains, additionally or alternatively a non-native disulphide bond may be present.

The TCRs of the invention may be αβ heterodimers. TCRs of the invention may be in single chain format. Single chain formats include, but are not limited to, αβ TCR polypeptides of the Vα-L-Vβ, Vβ-L-Vα, Vα-Cα-L-Vβ, Vα-L-Vβ-Cβ, or Vα-Cα-L-Vβ-Cβ types, wherein Vα and Vβ are TCR α and β variable regions respectively, Cα and Cβ are TCR α and β constant regions respectively, and L is a linker sequence (Weidanz et al., (1998) J Immunol Methods. Dec 1; 221 (1-2):59-76; Epel et al., (2002), Cancer Immunol Immunother. November; 51(10):565-73; WO 2004/033685; WO9918129). One or both of the constant domains may be full length, or they may be truncated as described above, and/or contain mutations. The alpha chain extracellular constant may have an asparagine (N) or a lysine (K) residue at position 4 due to a natural polymorphism. In certain embodiments single chain TCRs of the invention may have an introduced disulphide bond between residues of the respective constant domains, as described in WO 2004/033685. Single chain TCRs are further described in WO2004/033685; WO98/39482; WO01/62908; Weidanz et al. (1998) J Immunol Methods 221(1-2): 59-76; Hoo et al. (1992) Proc Natl Acad Sci USA 89(10): 4759-4763; Schodin (1996) Mol Immunol 33(9): 819-829).

As will be obvious to those skilled in the art, it may be possible to truncate the sequences provided at the C-terminus and/or N-terminus thereof, by 1, 2, 3, 4, 5 or more residues, without substantially affecting the binding characteristics of the TCR. All such trivial variants are encompassed by the present invention.

Alpha-beta heterodimeric TCRs of the invention usually comprise an alpha chain TRAC constant domain sequence and/or a beta chain TRBC1 or TRBC2 constant domain sequence. The alpha and beta chain constant domain sequences may be modified by truncation or substitution to delete the native disulphide bond between Cys4 of exon 2 of TRAC and Cys2 of exon 2 of TRBC1 or TRBC2. The alpha and/or beta chain constant domain sequence(s) may be modified by substitution of cysteine residues for Thr 48 of TRAC and Ser 57 of TRBC1 or TRBC2, the said cysteines forming a disulphide bond between the alpha and beta constant domains of the TCR. TRBC1 or TRBC2 may additionally include a cysteine to alanine mutation at position 75 of the constant domain and an asparagine to aspartic acid mutation at position 89 of the constant domain.

The constant domain may additionally or alternatively contain further mutations, substitutions or deletions relative to the native TRAC and/or TRBC½ sequences. The term TRAC and TRBC½ encompasses natural polymophic variants, for example N to K at position 4 of TRAC (Bragado et al Int Immunol, 1994 Feb.; 6(2):223-30).

Also included with the scope of the invention are variants, fragments and derivatives of the TCRs provided by the invention.

The invention also includes particles displaying TCRs of the invention and the inclusion of said particles within a library of particles. Such particles include but are not limited to phage, yeast ribosomes, or mammalian cells. Method of producing such particles and libraries are known in the art (for example see WO2004/044004; WO01/48145, Chervin et al. (2008) J. Immuno. Methods 339.2: 175-184).

In a further aspect, the present invention provides nucleic acid encoding a TCR of the invention. In some embodiments, the nucleic acid is cDNA. In some embodiments, the invention provides nucleic acid comprising a sequence encoding an α chain variable domain of a TCR of the invention. In some embodiments, the invention provides nucleic acid comprising a sequence encoding a β chain variable domain of a TCR of the invention. The nucleic acid may be non-naturally occurring and/or purified and/or engineered. The nucleic acid sequence may be codon optimised, in accordance with expression system utilised.

In another aspect, the invention provides a vector which comprises nucleic acid of the invention. Preferably the vector is a TCR expression vector.

The invention also provides a cell harbouring a vector of the invention, preferably a TCR expression vector. The vector may comprise nucleic acid of the invention encoding in a single open reading frame, or two distinct open reading frames, encoding the alpha chain and the beta chain respectively. Another aspect provides a cell harbouring a first expression vector which comprises nucleic acid encoding the alpha chain of a TCR of the invention, and a second expression vector which comprises nucleic acid encoding the beta chain of a TCR of the invention. Such cells are particularly useful in adoptive therapy. The cells of the invention may be isolated and/or recombinant and/or non-naturally occurring and/or engineered.

Since the TCRs of the invention have utility in adoptive therapy, the invention includes a non-naturally occurring and/or purified and/or or engineered cell, especially a T-cell, presenting a TCR of the invention. The invention also provides an expanded population of T cells presenting a TCR of the invention. There are a number of methods suitable for the transfection of T cells with nucleic acid (such as DNA, cDNA or RNA) encoding the TCRs of the invention (see for example Robbins et al., (2008) J Immunol. 180: 6116-6131). T cells expressing the TCRs of the invention will be suitable for use in adoptive therapy-based treatment of cancer. As will be known to those skilled in the art, there are a number of suitable methods by which adoptive therapy can be carried out (see for example Rosenberg et al., (2008) Nat Rev Cancer 8(4): 299-308).

Soluble TCRs of the invention are useful for delivering detectable labels or therapeutic agents to antigen presenting cells and tissues containing antigen presenting cells. They may therefore be associated (covalently or otherwise) with a detectable label (for diagnostic purposes wherein the TCR is used to detect the presence of cells presenting the GVYDGREHTV (SEQ ID NO: 1)-HLA-A*02 complex); a therapeutic agent; or a PK modifying moiety.

Examples of PK modifying moieties include, but are not limited to, PEG (Dozier et al., (2015) Int J Mol Sci. Oct 28; 16(10):25831-64 and Jevsevar et al., (2010) Biotechnol J. January; 5(1):113-28), PASylation (Schlapschy et al., (2013) Protein Eng Des Sel. August; 26(8):489-501), albumin (Dennis et al., (2002) J Biol Chem. September 20; 277(38): 35035-43) and/or unstructured polypeptides (Schellenberger et al., (2009) Nat Biotechnol. Dec; 27(12):1186-90).

Detectable labels for diagnostic purposes include for instance, fluorescent labels, radiolabels, enzymes, nucleic acid probes and contrast reagents.

Therapeutic agents which may be associated with the TCRs of the invention include immune-modulators, radio-active compounds, enzymes (perforin for example) or chemotherapeutic agents (cis-platin for example). To ensure that toxic effects are exercised in the desired location the toxin could be inside a liposome linked to TCR so that the compound is released slowly. This will prevent damaging effects during the transport in the body and ensure that the toxin has maximum effect after binding of the TCR to the relevant antigen presenting cells.

Other suitable therapeutic agents include:
small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate 22arbour22ate, auristatin E vincristine and doxorubicin;

peptide cytotoxins, i.e. proteins or fragments thereof with the ability to kill mammalian cells. For example, ricin, diphtheria toxin, *pseudomonas* bacterial exotoxin A, Dnase and Rnase;

radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

Immuno-stimulants, i.e. immune effector molecules which stimulate immune response. For example, cytokines such as IL-2 and IFN-γ, Superantigens and mutants thereof;

TCR-HLA fusions, e.g. fusion to a peptide-HLA complex, wherein said peptide is derived from a common human pathogen, such as Epstein Barr Virus (EBV);

chemokines such as IL-8, platelet factor 4, melanoma growth stimulatory protein, etc;

antibodies or fragments thereof, including anti-T cell or NK cell determinant antibodies (e.g. anti-CD3, anti-CD28 or anti-CD16);

alternative protein scaffolds with antibody like binding characteristics complement activators;

xenogeneic protein domains, allogeneic protein domains, viral/bacterial protein domains, viral/bacterial peptides.

One preferred embodiment is provided by a TCR of the invention associated (usually by fusion to an N- or C-terminus of the alpha or beta chain) with an anti-CD3 antibody, or a functional fragment or variant of said anti-CD3 antibody (such TCR-anti-CD3 fusions may be termed ImmTAC™ molecules). As used herein, the term "antibody" encompasses such fragments and variants. Examples of anti-CD3 antibodies include but are not limited to OKT3, UCHT-1, BMA-031 and 12F6. Antibody fragments and variants/analogues which are suitable for use in the compositions and methods described herein include minibodies, Fab fragments, F(ab')2 fragments, dsFv and scFv fragments, Nanobodies™ (these constructs, marketed by Ablynx (Belgium), comprise synthetic single immunoglobulin variable heavy domain derived from a camelid (e.g. camel or llama) antibody) and Domain Antibodies (Domantis (Belgium), comprising an affinity matured single immunoglobulin variable heavy domain or immunoglobulin variable light domain) or alternative protein scaffolds that exhibit antibody like binding characteristics such as Affibodies (Affibody (Sweden), comprising engineered protein A scaffold) or Anticalins (*Pieris* (Germany)), comprising engineered anticalins) to name but a few.

Linkage of the TCR and the anti-CD3 antibody may be via covalent or non-covalent attachment. Covalent attachment may be direct, or indirect via a linker sequence. Linker sequences are usually flexible, in that they are made up primarily of amino acids such as glycine, alanine and serine which do not have bulky side chains likely to restrict flexibility. Usable or optimum lengths of linker sequences are easily determined. Often the linker sequence will be less than about 12, such as less than 10, or from 2-10 amino acids in length. Suitable linkers that may be used in TCRs of the invention include, but are not limited to: GGGGS (SEQ ID NO: 30), GGGSG (SEQ ID NO: 31), GGSGG (SEQ ID NO: 32), GSGGG (SEQ ID NO: 33), GSGGGP (SEQ ID NO: 34), GGEPS (SEQ ID NO: 35), GGEGGGP (SEQ ID NO: 36), and GGEGGGSEGGGS (SEQ ID NO: 37) (as described in WO2010/133828).

Specific embodiments of anti-CD3-TCR fusion constructs of the invention include those alpha and beta chain pairings in which the alpha chain is composed of a variable domain comprising the amino acid sequence of SEQ ID NOs: 16-24 or 46-64 and/or the beta chain is composed of a variable domain comprising the amino acid sequence of SEQ ID NOs: 25-29 or 65-81. Said alpha and beta chains may further comprise a constant region comprising a non-native disulphide bond. The N or C terminus of the alpha and or beta chain may be fused to an anti-CD3 scFv antibody fragment via a linker selected from SEQ ID NOs: 30-37. Certain preferred embodiments of such anti-CD3-TCR fusion constructs are provided below:

TABLE 7

| Alpha chain SEQ ID NO | Beta Chain SEQ ID NO |
|---|---|
| 38 | 42 |
| 38 | 43 |
| 39 | 44 |
| 40 | 45 |
| 41 | 45 |

Each linker of SEQ ID NOs: 30-37 may be used with each or any of the preferred embodiments of CD3-TCR fusion constructs. For example, a TCR-CD3 fusion comprising the alpha chain of SEQ ID NO: 24 and the beta chain of SEQ ID NO: 29, wherein the beta chain is fused to an anti-CD3 scFv via a linker of any of SEQ ID NOs: 31-37 is included in the invention.

For some purposes, the TCRs of the invention may be aggregated into a complex comprising several TCRs to form a multivalent TCR complex. There are a number of human proteins that contain a multimerisation domain that may be used in the production of multivalent TCR complexes. For example the tetramerisation domain of p53 which has been utilised to produce tetramers of scFv antibody fragments which exhibited increased serum persistence and significantly reduced off-rate compared to the monomeric scFv fragment (Willuda et al. (2001) J. Biol. Chem. 276 (17) 14385-14392). Haemoglobin also has a tetramerisation domain that could be used for this kind of application. A multivalent TCR complex of the invention may have enhanced binding capability for the GVYDGREHTV (SEQ ID NO: 1)-HLA-A*02 complex compared to a non-multimeric wild-type or T cell receptor heterodimer of the invention. Thus, multivalent complexes of TCRs of the invention are also included within the invention. Such multivalent TCR complexes according to the invention are particularly useful for tracking or targeting cells presenting particular antigens in vitro or in vivo, and are also useful as intermediates for the production of further multivalent TCR complexes having such uses.

As is well-known in the art, TCRs may be subject to post translational modifications. Glycosylation is one such modification, which comprises the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Controlled glycosylation has been used to improve antibody based therapeutics. (Jefferis et al., (2009) Nat Rev Drug Discov March; 8(3):226-34.). For soluble TCRs of the invention glycosylation may be controlled in vivo, by using particular cell lines for example, or in vitro, by chemical modification. Such modifications are desirable, since glycosylation can improve pharmacokinetics, reduce immunogenicity and more closely mimic a native human protein (Sinclair and Elliott, (2005) Pharm Sci. August; 94(8):1626-35).

For administration to patients, the TCRs of the invention (preferably associated with a detectable label or therapeutic agent or expressed on a transfected T cell), TCR-anti CD3 fusion molecules, nucleic acids, expression vectors or cells of the invention may be provided in a pharmaceutical composition together with one or more pharmaceutically acceptable carriers or excipients. Therapeutic or imaging TCRs, or cells, in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, such as parenteral (including subcutaneous, intramuscular, or intravenous), enteral (including oral or rectal), inhalation or intranasal routes. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. a suitable dose range for a soluble TCR of the invention associated with an anti-CD3 antibody may be between 25 ng/kg and 50 µg/kg. A physician will ultimately determine appropriate dosages to be used.

TCRs, pharmaceutical compositions, vectors, nucleic acids and cells of the invention may be provided in substantially pure form, for example at least 80%, at least 85%, at least 90%, at least 91%, at least 92%, at least 93%, at least 94%, at least 95%, at least 96%, at least 97%, at least 98%, at least 99% or 100% pure.

Also provided by the invention are:
A TCR, TCR-anti-CD3 fusion molecule, nucleic acid, pharmaceutical composition or cell of the invention for use in medicine, preferably for use in a method of treating cancer or a tumour;
the use of a TCR, TCR-anti-CD3 fusion molecule, nucleic acid, pharmaceutical composition or cell of the invention in the manufacture of a medicament for treating cancer or a tumour;
a method of treating cancer or a tumour in a patient, comprising administering to the patient a TCR, TCR-anti-CD3 fusion molecule, nucleic acid, pharmaceutical composition or cell of the invention;
an injectable formulation for administering to a human subject comprising a TCR, TCR-anti-CD3 fusion molecule, nucleic acid, pharmaceutical composition or cell of the invention.

The cancer may be of the breast, oesophagus, head & neck, lung, ovary or bladder. The tumour may express MAGE A4, and/or may be a solid tumour. The TCR, TCR-anti-CD3 fusion molecule, nucleic acid, pharmaceutical composition or cell of the invention may be administered by injection, such as intravenous or direct intratumoral injection. The human subject may be at HLA-A*02 subtype.

Preferred features of each aspect of the invention are as for each of the other aspects mutatis mutandis. The prior art documents mentioned herein are incorporated to the fullest extent permitted by law.

DESCRIPTION OF THE DRAWINGS

FIG. 1— provides the amino acids sequence of the extracellular regions of a native MAGE A4 TCR alpha and beta chain.

FIG. 2— provides the amino acid sequence of the extracellular regions of a soluble native MAGE A4 TCR alpha and beta chain.

FIG. 3— provides example amino acid sequences of mutated MAGE A4 TCR alpha chain variable regions.

FIG. 4— provides example amino acid sequences of mutated MAGE A4 TCR beta chain variable regions.

FIG. 5— provides example alpha chain amino acid sequences of MAGE A4 TCR-anti-CD3 fusion molecules.

FIG. 6— provides example beta chain amino acid sequences of MAGE A4 TCR-anti-CD3 fusion molecules.

FIG. 7—provides cellular data demonstrating potency and specificity of MAGE A4 TCR-anti-CD3 fusion molecules.

EXAMPLES

Figure 8:
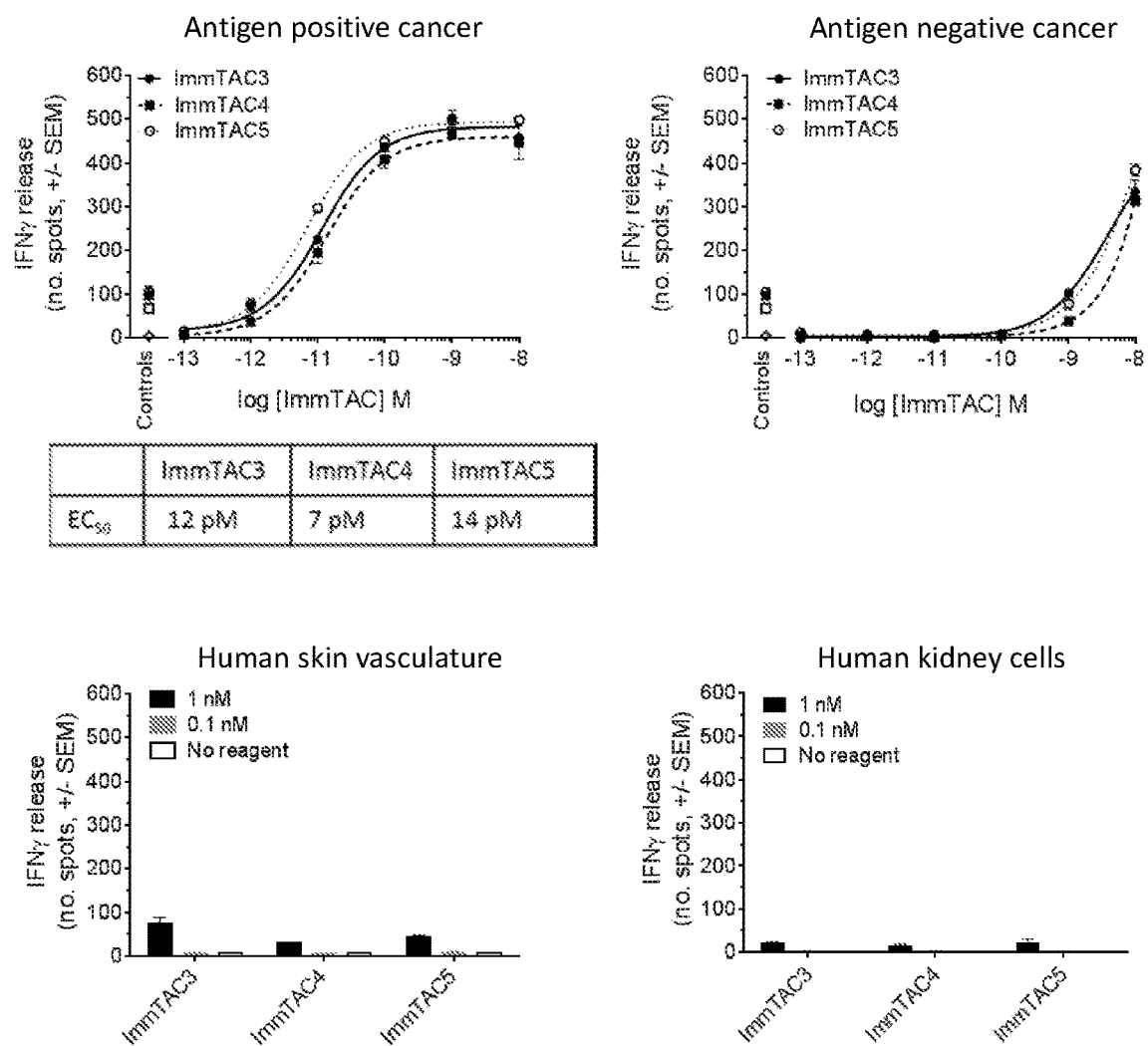
FIG. 8—provides cellular data demonstrating potency and specificity of further MAGE A4 TCR-anti-CD3 fusion molecules.

Example 1—Expression, Refolding and Purification of Soluble TCRs

Method
DNA sequences encoding the alpha and beta extracellular regions of soluble TCRs of the invention were cloned separately into pGMT7-based expression plasmids using standard methods (as described in Sambrook, et al. Molecular cloning. Vol. 2. (1989) New York: Cold spring harbour laboratory press). The expression plasmids were transformed separately into E. coli strain Rosetta (BL21 pLysS), and single ampicillin-resistant colonies were grown at 37° C. in TYP (+ ampicillin 100 µg/ml) medium to an $OD_{600}$ of ~0.6-0.8 before inducing protein expression with 0.5 mM IPTG. Cells were harvested three hours post-induction by centrifugation. Cell pellets were lysed with BugBuster protein extraction reagent (Merck Millipore) according to the manufacturer's instructions. Inclusion body pellets were recovered by centrifugation. Pellets were washed twice in Triton buffer (50 mM Tris-HCl pH 8.1, 0.5% Triton-X100, 100 mM NaCl, 10 mM NaEDTA) and finally resuspended in detergent free buffer (50 mM Tris-HCl pH 8.1, 100 mM NaCl, 10 mM NaEDTA). Inclusion body protein yield was quantified by solubilising with 6 M guanidine-HCl and measuring $OD_{280}$. Protein concentration was then calculated using the extinction coefficient. Inclusion body purity was measured by solubilising with 8M Urea and loading ~2 µg onto 4-20% SDS-PAGE under reducing conditions. Purity was then estimated or calculated using densitometry software (Chemidoc, Biorad). Inclusion bodies were stored at +4° C. for short term storage and at −20° C. or −70° C. for longer term storage.

For soluble TCR refolding, α and β chain-containing inclusion bodies were first mixed and diluted into 10 ml solubilisation/denaturation buffer (6 M Guanidine-hydrochloride, 50 mM Tris HCl pH 8.1, 100 mM NaCl, 10 mM EDTA, 20 mM DTT) followed by incubation for 30 min at 37° C. Refolding was then initiated by further dilution into 1 L of refold buffer (100 mM Tris pH 8.1, 400 mM L-Arginine HCL, 2 mM EDTA, 4 M Urea, 10 mM cysteamine hydrochloride and 2.5 mM cystamine dihydrochloride) and the solution mixed well. The refolded mixture was dialysed against 10 L $H_2O$ for 18-20 hours at 5° C.±3° C. After this time, the dialysis buffer was twice replaced with 10 mM Tris pH 8.1 (10 L) and dialysis continued for another 15 hours. The refold mixture was then filtered through 0.45 µm cellulose filters.

Purification of soluble TCRs was initiated by applying the dialysed refold onto a POROS® 50HQ anion exchange column and eluting bound protein with a gradient of 0-500 mM NaCl in 20 mM Tris pH 8.1 over 50 column volumes using an Akta® purifier (GE Healthcare). Peak TCR fractions were identified by SDS PAGE before being pooled and concentrated. The concentrated sample was then applied to a Superdex® 75HR gel filtration column (GE Healthcare) pre-equilibrated in Dulbecco's PBS buffer. The peak TCR fractions were pooled and concentrated and the final yield of purified material calculated.

Example 2— Expression, Refolding and Purification of ImmTAC Molecules (Soluble TCR-Anti CD3 Fusion Molecules)

Method
ImmTAC preparation was carried out as described in Example 1, except that the TCR beta chain was fused via a linker to an anti-CD3 single chain antibody. In addition a cation exchange step was performed during purification following the anion exchange. In this case the peak fractions from anion exchange were diluted 20 fold in 20 mM MES (pH6.5), and applied to a POROS® 50HS cation exchange column. Bound protein was eluted with a gradient of 0-500 mM NaCl in 20 mM MES. Peak ImmTAC fractions were pooled and adjusted to 50 mM Tris pH 8.1, before being concentrated and applied directly to the gel filtration matrix as described in Example 1.

Example 3— Binding Characterisation

Binding analysis of purified soluble TCRs and ImmTAC molecules to the relevant peptide-HLA complex was carried out by surface plasmon resonance, using a BIAcore 3000 or BIAcore T200 instrument, or by biolayer interferometry, using a ForteBio Octet instrument). Biotinylated class I HLA-A*02 molecules were refolded with the peptide of interest and purified using methods known to those in the art (O'Callaghan et al. (1999). Anal Biochem 266(1): 9-15; Garboczi, et al. (1992). Proc Natl Acad Sci USA 89(8): 3429-3433). All measurements were performed at 25° C. in Dulbecco's PBS buffer, supplemented with 0.005% P20.

BIAcore Method

Biotinylated peptide-HLA monomers were immobilized on to streptavidin-coupled CM-5 sensor chips. Equilibrium binding constants were determined using serial dilutions of soluble TCR/ImmTAC injected at a constant flow rate of 30 µl min$^{-1}$ over a flow cell coated with ~200 response units (RU) of peptide-HLA-A*02 complex. Equilibrium responses were normalised for each TCR concentration by subtracting the bulk buffer response on a control flow cell containing an irrelevant peptide-HLA. The $K_D$ value was obtained by non-linear curve fitting using Prism software and the Langmuir binding isotherm, bound=C*Max/(C+KD), where "bound" is the equilibrium binding in RU at injected TCR concentration C and Max is the maximum binding.

For high affinity interactions, binding parameters were determined by single cycle kinetics analysis. Five different concentrations of soluble TCR/ImmTAC were injected over a flow cell coated with ~100-200 RU of peptide-HLA complex using a flow rate of 50-60 µl min$^{-1}$. Typically, 60-120 µl of soluble TCR/ImmTAC was injected at a top concentration of 100-200 nM, with successive 2 fold dilutions used for the other four injections. The lowest concentration was injected first. To measure the dissociation phase buffer was then injected until 10% dissociation occurred, typically after 1-3 hours. Kinetic parameters were calculated using BIAevaluation® software. The dissociation phase was fitted to a single exponential decay equation enabling calculation of half-life. The equilibrium constant $K_D$ was calculated from $k_{off}/k_{on}$.

Octet Method Biotinylated peptide-HLA monomers were captured to 1 nm on to (SA) streptavidin biosensors (Pall ForteBio) pre-immobilised with streptavidin. The sensors were blocked with free biotin (2 µM) for 2 minutes. Equilibrium binding constants were determined by immersing the loaded biosensors into soluble TCR/ImmTAC serially diluted in a 96-well or 384-well sample plate. Plate shaking was set to 1000 rpm. For low affinity interactions (µM range) a short association (~2 minutes) and a short dissociation time (~2 minutes) was used. Binding curves were processed by double reference subtraction of reference biosensors loaded with irrelevant pHLA using Octet Data Analysis Software (Pall ForteBio). Responses (nm) at equilibrium were used to estimate the $K_D$ value from steady state plots fitted to the equation Response=Rmax*conc/(KD+conc), where "response" is the equilibrium binding in nm at each TCR concentration (conc) and Rmax is the maximum binding response at pHLA saturation.

For high affinity interactions (nM-pM range), kinetic parameters were determined from binding curves at 3 TCR/ImmTAC concentrations typically 10 nM, 5 nM and 2.5 nM. The association time was 30 minutes and the dissociation time 1-2 hours. Binding curves were processed by double reference subtraction of reference biosensors loaded with irrelevant pHLA and blocked with biotin. Kinetic parameters $k_{on}$ and $k_{off}$ were calculated by global fitting directly to the binding curves using Octet Data Analysis Software (Pall ForteBio). $K_D$ was calculated from $k_{off}/k_{on}$ and the dissociation half-life was calculated from $t_{1/2}=0.693/k_{off}$.

Example 4— Binding Characterisation of the Native TCR

A soluble native TCR was prepared according to the methods described in Example 1 and binding to pHLA analysed according to Example 3. The amino acid sequences of the alpha and beta chains corresponded to those shown in FIG. 2. Soluble biotinylated HLA-A*02 was prepared with the MAGE A4 peptide GVYDGREHTV (SEQ ID NO: 1) and immobilised onto a BIAcore sensor chip.

Results

Binding was determined at various concentrations and the $K_D$ value for the interaction was determined to be 142 µM. Cross reactivity (specificity) was assessed against a panel of 15 irrelevant peptide HLA-A*02 complexes using the equilibrium BIAcore method of Example 3. The 15 irrelevant pHLAs were pooled into three groups and loaded onto one of three flow cells, to give approximately 1000 RU of each pHLA per flow cell. 20 µL of soluble wild type TCR was injected at concentrations of 73 µM over all flow cells at a rate of 20 µL/min. No significant binding was detected at either concentration indicting that the native TCR is specific for the GVYDGREHTV (SEQ ID NO: 1)—HLA-A*02 complex.

These data indicate that this TCR binds to the target with a suitable affinity and specificity and therefore provide a useful starting sequence for therapeutic TCRs.

Example 5— Binding Characterisation of Soluble Mutated TCRs and ImmTAC Molecules of the Invention Soluble mutated TCRs and ImmTAC molecules were produced based on the sequences provided in FIG. 2. Samples were prepared as described in Examples 1 and 2, and binding characteristics determined according to Example 3.

Results

A single cysteine to valine point mutation at position 19 of the alpha chain (SEQ ID NO: 6) was found to improve refolding and purification yield without affecting affinity or specificity (the $K_D$ for was recorded as 145 µM and no cross reactivly was observed to the same panel of 15 alternative peptide HLA complexes that were tested with the WT).

TCR alpha and/or beta chains were identified that contained mutations in at least one CDR region relative to the CDR sequences shown in FIG. 2 (SEQ ID NO: 4 and 5). These TCR sequences recognised GVYDGREHTV (SEQ ID NO: 1) HLA-A*02 complex with a particularly suitable affinity and/or half-life. In some cases further mutations were identified that improved the stability and/or yield of the TCR, including the alpha chain mutation K1A (with reference to the numbering of SEQ ID NO: 4). The amino acid sequences of certain mutated TCR alpha and beta chain variable regions of the invention are provided in FIGS. 4 and 5 respectively. The table below provides binding characteristics for soluble TCRs or ImmTAC molecules (soluble TCR anti-CD3 fusion molecules) comprising the indicated alpha and beta variable regions.

TABLE 9

| Alpha chain (SEQ ID NO) | Beta chain (SEQ ID No) | Format (soluble TCR or ImmTAC) | Method (Biacore/ Octet) | Binding parameters | |
|---|---|---|---|---|---|
| | | | | KD | T$_{1/2}$ |
| WTc19v (16) | b1 (25) | Soluble TCR | Biacore | 330 nM | >2 min |
| a7 (17) | b1 (25) | Soluble TCR | Octet | nd | 24 min |
| a12 (18) | b1 (25) | Soluble TCR | Octet | nd | 24 min |
| a13 (19) | b1 (25) | Soluble TCR | Octet | nd | 144 min |
| a19 (21) | b1 (25) | Soluble TCR | Octet | nd | 7.2 h |
| WTc19v (16) | b14 (26) | Soluble TCR | Octet | nd | 10 min |
| WTc19v (16) | b21 (28) | Soluble TCR | Octet | nd | 23 min |
| a13 (19) | b21 (28) | Soluble TCR | Biacore | nd | 13 h |
| a13 (19) | b14 (26) | Soluble TCR | Octet | nd | 4.1 h |
| a19 (21) | b14 (26) | Soluble TCR | Octet | nd | 9.1 h |
| a7 (17) | b21 (28) | ImmTAC | Octet | 155 pM | 5.4 h |
| a19ka (22) | b1 (25) | ImmTAC | Octet | 159 pM | 4.5 h |
| a19ka (22) | b21 (28) | ImmTAC | Octet | 53 pM | 16.9 h |
| a13ka (20) | b21 (28) | ImmTAC$^a$ | Biacore | 58.6 pM | 13.8 h |
| a19ka (22) | b14 (26) | ImmTAC$^b$ | Biacore | 32.3 pM | 27.6 h |
| a19ka (22) | b14L (27) | ImmTAC$^c$ | Octet | 75.1 pM | 13.7 h |
| a13kaLQ (24) | b21L (29) | ImmTAC$^d$ | Biacore | 74 pM | 15.6 h |
| a13kaLS (23) | b21L (29) | ImmTAC$^e$ | Biacore | 62.6 pM | 8.9 h | nd = non determined
$^a$Corresponds to ImmTAC3 from example 6, full alpha and beta chain sequences are provided by SEQ ID NO: 39 and SEQ ID NO: 44 respectively. Values based on average from 7 independent measurements
$^b$Corresponds to ImmTAC1 from example 6, full alpha and beta chain sequences are provided by SEQ ID NO: 38 and SEQ ID NO: 42 respectively. Values based on average from 7 independent measurements
$^c$Corresponds to ImmTAC2 from example 6, full alpha and beta chain sequences are provided by SEQ ID NO: 38 and SEQ ID NO: 43 respectively
$^d$Corresponds to ImmTAC4 from example 6, full alpha and beta chain sequences are provided by SEQ ID NO: 40 and SEQ ID NO: 45 respectively. Values based on average from 4 independent measurements
$^e$Corresponds to ImmTAC5 from example 6, full alpha and beta chain sequences are provided by SEQ ID NO: 41 and SEQ ID NO: 45 respectively Further combinations of alpha and beta variable regions containing mutations of the invention were tested for binding to the GVYDGREHTV (SEQ ID NO: 1) HLA-A*02 complex. The data presented in the table below were obtained using Biacore, as described above. The indicated alpha and beta variable domain sequences were prepared as ImmTAC molecules.

TABLE 10

| Alpha chain (SEQ ID NO) | Beta Chain (SEQ ID NO) | KD | T1/2 |
|---|---|---|---|
| a36 (SEQ ID NO: 46) | b21L (SEQ ID NO: 29) | 210 pM | 9.2 h |
| a37 (SEQ ID NO: 47) | b21L (SEQ ID NO: 29) | 24 pM | 47.0 h |
| a38 (SEQ ID NO 48) | b21 (SEQ ID NO: 29) | 233 pM | 10.0 h |
| a39 (SEQ ID NO: 49) | b21 (SEQ ID NO: 29) | 3013 pM | 0.6 h |
| a40 (SEQ ID NO: 50) | b21 (SEQ ID NO: 29) | 176 pM | 4.5 h |
| a41 (SEQ ID NO: 51) | b21 (SEQ ID NO: 29) | 429 pM | 2.7 h |
| a13ka (SEQ ID NO:) | b41 (SEQ ID NO: 65) | 45 pM | 25.1 h |
| a13kaLQ (SEQ ID NO: 24) | b42 (SEQ ID NO: 66) | 424 pM | 2.1 h |
| a13kaLQ (SEQ ID NO: 24) | b43 (SEQ ID NO: 67) | 150 pM | 8.0 h |
| a13kaLQ (SEQ ID NO: 24) | b44 (SEQ ID NO: 68) | 132 pM | 9.0 h |
| a13kaLQ (SEQ ID NO: 24) | b45 (SEQ ID NO: 69) | 704 pM | 1.9 h |
| a13kaLQ (SEQ ID NO: 24) | b46 (SEQ ID NO: 70) | 1913 pM | 0.9 h |
| a30 (SEQ ID NO: 52) | b14 (SEQ ID NO: 26) | 103 pM | 17 h |
| a42 (SEQ ID NO: 53) | b14 (SEQ ID NO: 26) | 21 pM | 46.4 h |
| a31 (SEQ ID NO: 54) | b14 (SEQ ID NO: 26) | 182 pM | 9 h |
| a43 (SEQ ID NO: 55) | b14 (SEQ ID NO: 26) | 258 pM | 6.0 h |
| a32 (SEQ ID NO: 56) | b14 (SEQ ID NO: 26) | 179 pM | 12 h |
| a44 (SEQ ID NO: 57) | b14 (SEQ ID NO: 26) | 88 pM | 19.0 h |
| a33 (SEQ ID NO: 58) | b14 (SEQ ID NO: 26) | 947 pM | 1.2 h |
| a45 (SEQ ID NO: 59) | b14 (SEQ ID NO: 26) | 74 pM | 11.8 h |
| a34 (SEQ ID NO: 60) | b14 (SEQ ID NO: 26) | 167 pM | 8.7 h |
| a19ka (SEQ ID NO: 22) | b32 (SEQ ID NO: 71) | 37.0 pM | 30.9 h |
| a19ka (SEQ ID NO: 22) | b33 (SEQ ID NO: 72) | 33 pM | 35.9 h |
| a19ka (SEQ ID NO: 22) | b34 (SEQ ID NO: 73) | 54 pM | 21.2 h |
| a19ka (SEQ ID NO: 22) | b35 (SEQ ID NO: 74) | 28 pM | 37.4 h |
| a19ka (SEQ ID NO: 22) | b36 (SEQ ID NO: 75) | 11 pM | 58 h |
| a19ka (SEQ ID NO: 22) | b37 (SEQ ID NO: 76) | 47 pM | 24.9 h |
| a19ka (SEQ ID NO: 22) | b38 (SEQ ID NO: 77) | 597 pM | 2.3 h |
| a19ka (SEQ ID NO: 22) | b39 (SEQ ID NO: 78) | 923 pM | 1.1 h |
| a19ka (SEQ ID NO: 22) | b40 (SEQ ID NO: 79) | 143 pM | 7.9 h |
| aM50L (SEQ ID NO: 62) | bWT (SEQ ID NO: 5) | 31.3 µM | nd |
| aS95A (SEQ ID NO: 63) | bWT (SEQ ID NO: 5) | 3.5 µM | nd |
| aS98L (SEQ ID NO: 64) | bWT (SEQ ID NO: 5) | 39.1 µM | nd |
| aWTka (SEQ ID NO: 61) | bL96D (SEQ ID NO: 80) | 71.4 µM | nd |
| aWTka (SEQ ID NO: 61) | bM97Q (SEQ ID NO: 81) | 27.5 µM | nd | nd—not determined

The data presented in tables 9 and 10 indicate that certain TCR variable sequences of the invention have a high binding affinity and long half-life for the GVYDGREHTV (SEQ ID NO: 1) HLA-A*02 complex, and are therefore particularly suitable for use as soluble therapeutic reagents.

In addition to binding the cognate GVYDGREHTV (SEQ ID NO: 1) HLA-A*02 complex, TCRs of the invention were also assessed for binding to similar peptides derived from MAGE A8 and MAGE B2 and presented by HLA-A*02. The numbers in the table below provide Biacore binding data for three ImmTAC molecules comprising the indicated alpha and beta variable domain sequences. All three ImmTAC molecules recognise the MAGE-A8 peptide at a similar level to the cognate peptide and MAGE-B2 peptide at a weaker level.

TABLE 11

| Alpha chain (SEQ ID NO) | Beta chain (SEQ ID NO) | MAGE-A8 | | MAGE-B2 | |
|---|---|---|---|---|---|
| | | KD | T$_{1/2}$ | KD | T$_{1/2}$ |
| a19ka (22) | b14 (26)$^a$ | 62.8 pM | 17.5 h | 468 pM | 7.7 h |
| a13ka (20) | b21 (28)$^b$ | 99.2 pM | 8.7 h | 847 pM | 4.2 h |
| a13kaLQ (24) | b21L (29)$^c$ | 155 pM | 9.6 h | 1532 pM | 3.27 h |

$^a$Corresponds to ImmTAC1 from example 6, full alpha and beta chain sequences are provided by SEQ ID NO: 38 and SEQ ID NO: 42 respectively.
$^b$Corresponds to ImmTAC3 from example 6, full alpha and beta chain sequences are provided by SEQ ID NO: 39 and SEQ ID NO: 44 respectively.
$^c$Corresponds to ImmTAC4 from example 6, full alpha and beta chain sequences are provided by SEQ ID NO: 40 and SEQ ID NO: 45 respectively.

Example 6— Potent and Specific T Cell Redirection by ImmTAC Molecules

ImmTAC molecules containing mutated alpha and beta variable chain sequences with particularly high affinity for the target antigen were tested for their ability to mediate potent and specific redirection of CD3+ T cells by ELISPOT assay, using interferon-γ (IFN-γ) secretion as a read out for T cell activation.

In this example, the sequence of the alpha chain variable region was selected from SEQ ID NOs: 20-24, and the sequence of the beta chain variable region was selected from SEQ ID NOs: 26-29. The variable domain sequences were fused to the respective alpha or beta extracellular constant domain sequences and contained a non-native disulphide bond. In each case the beta chain was fused via a linker to an anti-CD3 scFv; the linker was selected from SEQ ID NOs: 30-37. The full sequences of the ImmTAC molecules tested are provided by the SEQ ID NOs set out in the following table:

TABLE 12

|  | Alpha chain SEQ ID NO | Beta Chain SEQ ID NO |
|---|---|---|
| ImmTAC1 | 38 | 42 |
| ImmTAC2 | 38 | 43 |
| ImmTAC3 | 39 | 44 |
| ImmTAC4 | 40 | 45 |
| ImmTAC5 | 41 | 45 |

Method

Assays were performed using a human IFN-γ ELISPOT kit (BD Biosciences). Target cells were prepared at a density of $1 \times 10^6$/ml in assay medium (RPMI 1640 containing 10% heat inactivated FBS and 1% penicillin-streptomycin-L-glutamine) and plated at 50,000 cells per well in a volume of 50 μl. Peripheral blood mononuclear cells (PBMC), isolated from fresh donor blood, were used as effector cells and plated at 10,000-50,000 cells per well in a volume of 50 μl (the exact number of cells used for each experiment is donor dependent and may be adjusted to produce a response within a suitable range for the assay). Varying concentrations of ImmTAC were used, spanning the anticipated clinically relevant range, and added to the well in a volume of 50 μl.

Plates were prepared according to the manufacturer's instructions. Target cells, effector cells and ImmTAC molecules were added to the relevant wells and made up to a final volume of 200 μl with assay medium. All reactions were performed in triplicate. Control wells were also prepared with the omission of, ImmTAC, effector cells, or target cells. The plates were then incubated overnight (37° C./5% $CO_2$). The next day the plates were washed three times with wash buffer (1×PBS sachet, containing 0.05% P20, made up in deionised water). Primary detection antibody was then added to each well in a volume of 50 μl. Plates were incubated at room temperature for 2 hours prior to being washed again three times. Secondary detection was performed by adding 50 μl of diluted streptavidin-HRP to each well and incubating at room temperature for 1 hour and the washing step repeated. No more than 15 mins prior to use, one drop (20 μl) of AEC chromogen was added to each 1 ml of AEC substrate and mixed and 50 μl added to each well. Spot development was monitored regularly and plates were washed in tap water to terminate the development reaction. The plates were then allowed to dry at room temperature for at least 2 hours prior to counting the spots using a CTL analyser with Immunospot software (Cellular Technology Limited).

Results

The data presented in FIGS. 7 and 8, upper panels, show that ImmTAC molecules 1-2 and 3-5 respectively are able to mediate potent (i.e. EC50 less than 100 pM) T cell redirection against cancer cells expressing target antigen (NCI-H1703—human lung cancer cell line). No T cell activation was detected against antigen negative cancer cells (NCI-H441 human papillary adenocarcinoma cell line for ImmTAC molecules 1-2, and CAMA-1 human breast cancer cell line for ImmTAC molecules 3-5), within the clinical relevant concentration range 1 nM), demonstrating that the response is specific.

The ImmTAC molecules were tested for specificity using cells derived from normal healthy human tissues as target cells. The lower panel in FIG. 7 demonstrates that ImmTAC molecules 1-2 have minimal reactivity at a clinical relevant concentration against a human skin vasculature cells. Similarly, the lower panels in FIG. 8 demonstrate than ImmTAC molecules 3-5 have minimal reactivity at a clinical relevant concentration against human skin vasculature cells and human renal cells.

Figure 9:
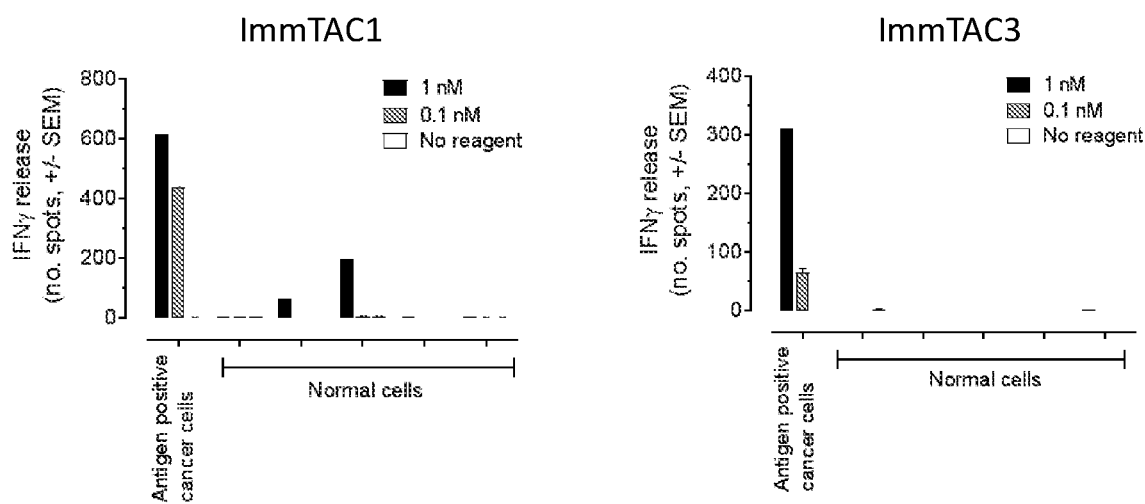
FIG. 9—provides further evidence of specificity of MAGE A4 TCR-anti-CD3 fusion molecules FIG. 10—provides further specificity data for MAGE A4 TCR-anti-CD3 fusion molecules FIG. 11—provides evidence that MAGE A4 TCR-anti-CD3 fusion molecules lead to killing of cancer cells The invention is further described in the following non-limiting examples.

ImmTAC molecules 1 and 3 were further tested for specificity against a panel of human cells derived from normal healthy tissues using the same ELISPOT methodology described above. The data presented in FIG. 9 show limited T cell activation, within a clinical relevant concentration range (≤1 nM), for healthy tissues including skin vasculature, cardiac, skeletal, hepatic and pulmonary.

Figure 10:
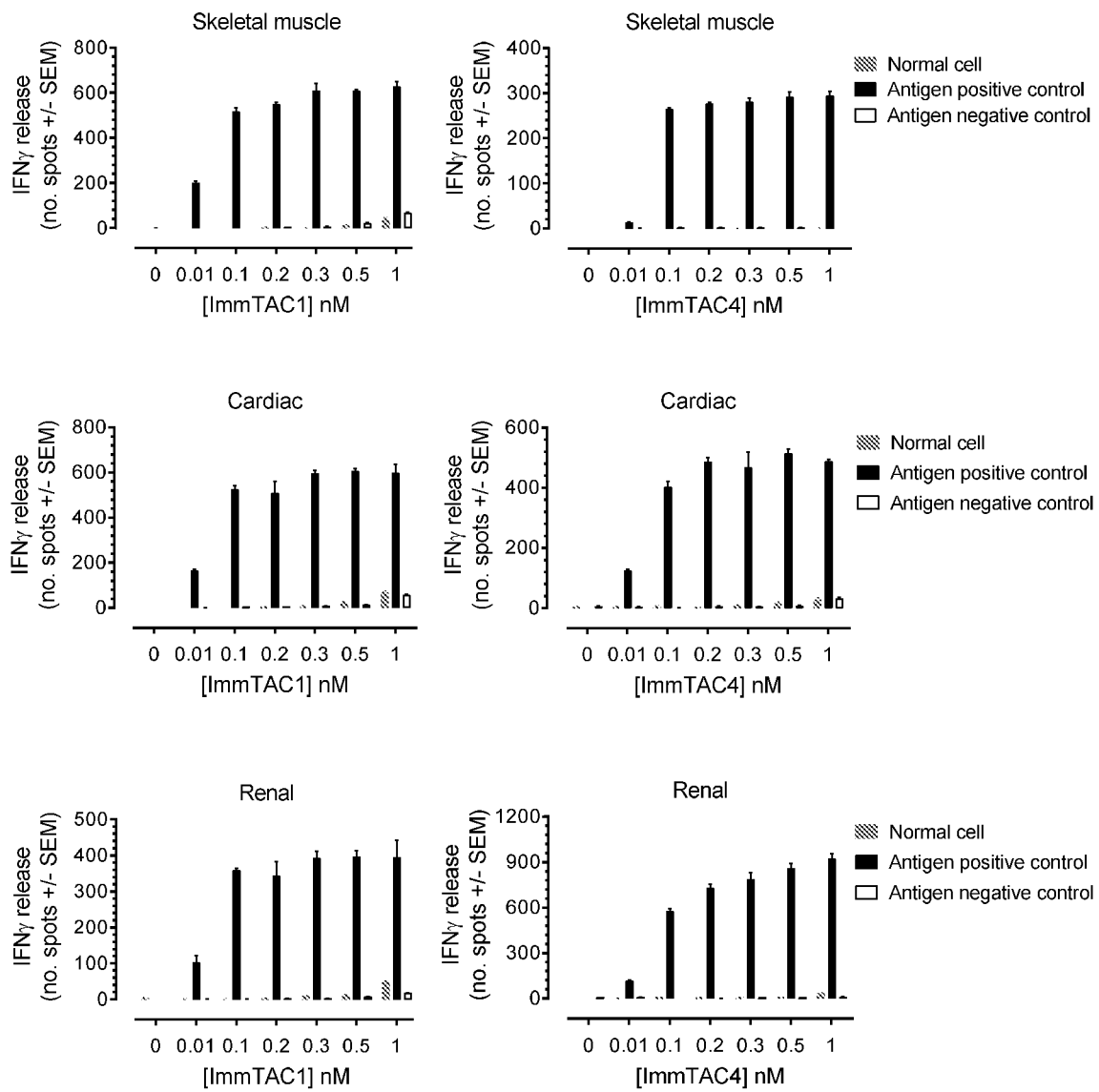

ImmTAC molecules 1 and 4 were additionally tested for reactivity against an extended panel of >10 normal cell types, using the same ELISPOT methodology described above and with a finer range of ImmTAC concentrations (0.01 nM, 0.1 nM, 0.2 nM, 0.3 nM, 0.5 nM and 1 nM). FIG. 10 shows representative data obtained from skeletal, cardiac, and renal cells. In each case, antigen positive cells (NCI-H1703) and antigen negative cells (NCI-H441) were included as controls. The data demonstrate negligible reactivity against normal cells, relative to antigen positive cells, within a clinically relevant concentration range 1 nM).

These data indicate that these ImmTAC molecules demonstrate a high level of potency and specificity and are therefore particularly suitable for therapeutic use.

Example 7—Potent Killing of Tumour Cells by ImmTAC Redirected T Cells

The ability of ImmTAC molecules of the invention to mediate potent redirected T cell killing of antigen positive tumour cells was investigated using the IncuCyte platform (Essen BioScience). This assay allows real time detection by microscopy of the release of Caspase-3/7, a marker for apoptosis.

Method

Assays were performed using the CellPlayer 96-well Caspase-3/7 apoptosis assay kit (Essen BioScience, Cat. No. 4440) and carried out according the manufacturers protocol. Briefly, target cells (NCI-H1703—antigen$^{+ve}$HLA A*02$^{+ve}$ and NCI-H441—antigen$^{+ve}$ HLA A*02$^{+ve}$) were plated at 5000 cells per well and incubated overnight to allow them to adhere. ImmTAC solutions were prepared at concentrations between 0.5 nM to 0.01 nM, and 25 μl of each concentration was added to the relevant well. Effector cells were used at an effector target cell ratio of 10:1 (50000 cells per well). A control sample without ImmTAC was also prepared. NucView assay reagent was made up at 30 μM and 25 μl added to every well and the final volume brought to 150 μl (giving 5 μM final conc). The plate was placed in the IncuCyte instrument and images taken every 2 hours (1 image per well) over 3 days. The number of apoptotic cells in each image was determined and recorded as apoptotic cells per $mm^2$. Assays were performed in triplicate.

Results

The data presented in FIG. 11 show real-time killing of tumour cells by ImmTAC redirected T cells. Results are presented for ImmTAC1 and ImmTAC4. Both ImmTAC molecules show T cell redirected killing of antigen positive tumour cells at a concentration of 0.01 nM. No killing of antigen negative cells is observed even at the highest concentration (0.5 nM).

These data confirm that ImmTAC1 and immTAC4 mediate potent redirected T cell killing of antigen positive tumour cell.

The invention claimed is:

1. A T cell receptor (TCR), wherein the TCR is a soluble TCR comprising a TCR alpha chain comprising a TCR alpha chain variable domain and a TCR beta chain comprising a TCR beta chain variable domain, wherein the alpha chain variable domain comprises Complementarity Determining Regions (CDRs) of a CDR1 comprising the sequence VSPFSN (SEQ ID NO:6), a CDR2 comprising the sequence LTFSENT (SEQ ID NO:83), and a CDR3 comprising the sequence VVNSAQGLYIPTF (SEQ ID NO:87), and wherein the beta chain variable domain comprises CDRs of a CDR1 comprising the sequence LDHEN (SEQ ID NO:90), a CDR2 comprising the sequence SRFATG (SEQ ID NO:88), and a CDR3 comprising the sequence ASSSDQNSGDPYEQYF (SEQ ID NO:89).

2. A TCR as claimed in claim 1, wherein the alpha chain variable domain comprises at least one of the following mutations with reference to the numbering of SEQ ID NO: 2: C19V and 1KA.

3. A TCR as claimed in claim 1, comprising:
an alpha chain variable domain sequence corresponding to SEQ ID NO:24, and a beta chain variable domain sequence corresponding to SEQ ID NO:29.

4. A TCR as claimed in claim 1, which is an alpha-beta heterodimer, having an alpha chain T cell receptor alpha constant (TRAC) domain sequence and a beta chain T cell receptor beta constant 1 or 2 (TRBC1 or TRBC2) domain sequence.

5. A TCR as claimed in claim 4, wherein the alpha and beta chain constant domain sequences are modified by truncation or substitution to delete a native disulphide bond between Cys4 of exon 2 of TRAC and Cys2 of exon 2 of TRBC1 or TRBC2.

6. A TCR as claimed in claim 4, wherein the alpha and beta chain constant domain sequences are modified by substitution of cysteine residues for Thr 48 of TRAC and Ser 57 of TRBC1 or TRBC2, said cysteines forming a non-native disulphide bond between the alpha and beta constant domains of the TCR.

7. A TCR as claimed in claim 1, which is in single chain format of the type Vα-L-Vβ, Vβ-L-Vα, Vα-Cα-L-Vβ, Vα-L-Vβ-Cβ, wherein Vα and Vβ are TCR α and β variable regions respectively, Cα and Cβ are TCR α and β constant regions respectively, and L is a linker sequence.

8. A TCR as claimed in claim 1, wherein the TCR is associated with a detectable label, a therapeutic agent, or a PK modifying moiety.

9. A TCR as claimed in claim 8, wherein the therapeutic agent is an anti-CD3 antibody covalently linked to the C- or N-terminus of the alpha or beta chain of the TCR.

10. A TCR as claimed in claim 9, wherein the anti-CD3 antibody is covalently linked to the C- or N-terminus of the beta chain of the TCR via a linker sequence.

11. A TCR as claimed in claim 10, wherein the linker sequence is selected from the group consisting of GGGGS (SEQ ID NO: 30), GGGSG (SEQ ID NO: 31), GGSGG (SEQ ID NO: 32), GSGGG (SEQ ID NO: 33), GSGGGP (SEQ ID NO: 34), GGEPS (SEQ ID NO: 35), GGEGGGP (SEQ ID NO: 36), and GGEGGGSEGGGS (SEQ ID NO: 37).

12. A TCR-anti-CD3 fusion molecule, wherein the alpha chain variable domain comprises the amino acid sequence of SEQ ID NO: 24 and the beta chain variable domain comprises the amino acid sequence of SEQ ID NO: 29, and wherein an anti-CD3 antibody is covalently linked to the N-terminus or C-terminus of the TCR beta chain via a linker sequence selected from SEQ ID NOs: 30-37.

13. A TCR-anti CD3 fusion molecule as claimed in claim 12, comprising an alpha chain amino acid sequence corresponding to SEQ ID NO: 40 and beta chain amino acid sequence corresponding to SEQ ID NO: 45.

14. A nucleic acid encoding a TCR alpha chain or a TCR beta chain as claimed in claim 1.

15. An expression vector comprising the nucleic acid of claim 14.

16. A cell harbouring
   (a) an expression vector encoding TCR alpha and beta chains as claimed in claim 1, in a single open reading frame, or two distinct open reading frames; or
   (b) a first expression vector which comprises nucleic acid encoding the alpha chain of a TCR as claimed in claim 1, and a second expression vector which comprises nucleic acid encoding the beta chain of a TCR as claimed in claim 1.

17. A T cell presenting a TCR as claimed in claim 1.

18. A pharmaceutical composition comprising a TCR as claimed in claim 1 together with one or more pharmaceutically acceptable carriers or excipients.

19. An injectable formulation for administering to a human subject comprising a TCR according to claim 1.

20. A method of producing a TCR, comprising a) maintaining a cell according to claim 16 under optimal conditions for expression of the TCR alpha and beta chains and b) isolating the TCR alpha and beta chains.

21. A TCR as claimed in claim 1, wherein the TCR binds to a GVYDGREHTV (SEQ ID NO: 1) HLA-A*02 complex with an affinity greater than 200 μM.

22. A TCR as claimed in claim 3, wherein the TCR is associated with a detectable label, a therapeutic agent, or a PK modifying moiety.

23. A TCR as claimed in claim 22, wherein the therapeutic agent is an anti-CD3 antibody covalently linked to the C- or N-terminus of the alpha or beta chain of the TCR.

24. A TCR as claimed in claim 23, wherein the anti-CD3 antibody is covalently linked to the C- or N-terminus of the beta chain of the TCR via a linker sequence.

25. A TCR as claimed in claim 24, wherein the linker sequence is selected from the group consisting of GGGGS (SEQ ID NO: 30), GGGSG (SEQ ID NO: 31), GGSGG (SEQ ID NO: 32), GSGGG (SEQ ID NO: 33), GSGGGP (SEQ ID NO: 34), GGEPS (SEQ ID NO: 35), GGEGGGP (SEQ ID NO: 36), and GGEGGGSEGGGS (SEQ ID NO: 37).

26. A TCR as claimed in claim 4, wherein the TCR is associated with a detectable label, a therapeutic agent, or a PK modifying moiety.

27. A TCR as claimed in claim 26, wherein the therapeutic agent is an anti-CD3 antibody covalently linked to the C- or N-terminus of the alpha or beta chain of the TCR.

28. A TCR as claimed in claim 27, wherein the anti-CD3 antibody is covalently linked to the C- or N-terminus of the beta chain of the TCR via a linker sequence.

29. A TCR as claimed in claim 28, wherein the linker sequence is selected from the group consisting of GGGGS (SEQ ID NO: 30), GGGSG (SEQ ID NO: 31), GGSGG (SEQ ID NO: 32), GSGGG (SEQ ID NO: 33), GSGGGP (SEQ ID NO: 34), GGEPS (SEQ ID NO: 35), GGEGGGP (SEQ ID NO: 36), and GGEGGGSEGGGS (SEQ ID NO: 37).

30. A TCR as claimed in claim 5, wherein the TCR is associated with a detectable label, a therapeutic agent, or a PK modifying moiety.

31. A TCR as claimed in claim 30, wherein the therapeutic agent is an anti-CD3 antibody covalently linked to the C- or N-terminus of the alpha or beta chain of the TCR.

32. A TCR as claimed in claim 31, wherein the anti-CD3 antibody is covalently linked to the C- or N-terminus of the beta chain of the TCR via a linker sequence.

33. A TCR as claimed in claim 32, wherein the linker sequence is selected from the group consisting of GGGGS (SEQ ID NO: 30), GGGSG (SEQ ID NO: 31), GGSGG (SEQ ID NO: 32), GSGGG (SEQ ID NO: 33), GSGGGP (SEQ ID NO: 34), GGEPS (SEQ ID NO: 35), GGEGGGP (SEQ ID NO: 36), and GGEGGGSEGGGS (SEQ ID NO: 37).

34. A TCR as claimed in claim 6, wherein the TCR is associated with a detectable label, a therapeutic agent, or a PK modifying moiety.

35. A TCR as claimed in claim 34, wherein the therapeutic agent is an anti-CD3 antibody covalently linked to the C- or N-terminus of the alpha or beta chain of the TCR.

36. A TCR as claimed in claim 35, wherein the anti-CD3 antibody is covalently linked to the C- or N-terminus of the beta chain of the TCR via a linker sequence.

37. A TCR as claimed in claim 36, wherein the linker sequence is selected from the group consisting of GGGGS (SEQ ID NO: 30), GGGSG (SEQ ID NO: 31), GGSGG (SEQ ID NO: 32), GSGGG (SEQ ID NO: 33), GSGGGP (SEQ ID NO: 34), GGEPS (SEQ ID NO: 35), GGEGGGP (SEQ ID NO: 36), and GGEGGGSEGGGS (SEQ ID NO: 37).

38. A TCR as claimed in claim 10, wherein the alpha chain comprises the amino acid sequence of SEQ ID NO: 40, and the beta chain comprises the amino acid sequence of SEQ ID NO: 45.

39. A TCR as claimed in claim 11, wherein the alpha chain comprises the amino acid sequence of SEQ ID NO: 40, and the beta chain comprises the amino acid sequence of SEQ ID NO: 45.

40. A nucleic acid encoding a TCR-anti CD3 fusion molecule alpha chain or a TCR-anti CD3 fusion molecule beta chain as claimed in claim 13.

41. An expression vector comprising the nucleic acid of claim 40.

42. A cell harbouring
   (a) an expression vector encoding TCR-anti CD3 fusion molecule alpha and beta chains as claimed in claim 13, in a single open reading frame, or two distinct open reading frames; or
   (b) a first expression vector which comprises nucleic acid encoding the alpha chain of a TCR-anti CD3 fusion molecule as claimed in claim 13, and a second expression vector which comprises nucleic acid encoding the beta chain of a TCR-anti CD3 fusion molecule as claimed in claim 13.

43. A pharmaceutical composition comprising a TCR-anti CD3 fusion molecule as claimed in claim 13 together with one or more pharmaceutically acceptable carriers or excipients.

44. An injectable formulation for administering to a human subject comprising a TCR-anti CD3 fusion molecule according to claim 13.

45. A method of producing a TCR-anti CD3 fusion molecule, comprising a) maintaining a cell according to claim 42 under optimal conditions for expression of the TCR-anti CD3 fusion molecule alpha and beta chains and b) isolating the TCR alpha and beta chains.

* * * * *

SEQUENCE LISTING

<160> NUMBER OF SEQ ID NOS: 92

<210> SEQ ID NO 1
<211> LENGTH: 10
<212> TYPE: PRT
<213> ORGANISM: Homo sapiens

<400> SEQUENCE: 1

Gly Val Tyr Asp Gly Arg Glu His Thr Val
1               5                   10

<210> SEQ ID NO 2
<211> LENGTH: 207
<212> TYPE: PRT
<213> ORGANISM: Homo sapiens

<400> SEQUENCE: 2

Lys Asn Gln Val Glu Gln Ser Pro Gln Ser Leu Ile Ile Leu Glu Gly
1               5                   10                  15

Lys Asn Cys Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn His Ser Gly
                85                  90                  95

Gly Ser Tyr Ile Pro Thr Phe Gly Arg Gly Thr Ser Leu Ile Val His
            100                 105                 110

Pro Tyr Ile Gln Lys Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
    130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser
        195                 200                 205

<210> SEQ ID NO 3
<211> LENGTH: 246
<212> TYPE: PRT
<213> ORGANISM: Homo sapiens

<400> SEQUENCE: 3

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

```
Ser Val Ser Arg Glu Lys Glu Arg Phe Ser Leu Ile Leu Glu Ser
 65                  70                  75                  80

Ala Ser Thr Asn Gln Thr Ser Met Tyr Leu Cys Ala Ser Ser Phe Leu
                 85                  90                  95

Met Thr Ser Gly Asp Pro Tyr Glu Gln Tyr Phe Gly Pro Gly Thr Arg
            100                 105                 110

Leu Thr Val Thr Glu Asp Leu Lys Asn Val Phe Pro Pro Glu Val Ala
            115                 120                 125

Val Phe Glu Pro Ser Glu Ala Glu Ile Ser His Thr Gln Lys Ala Thr
130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
            195                 200                 205

His Phe Arg Cys Gln Val Gln Phe Tyr Gly Leu Ser Glu Asn Asp Glu
            210                 215                 220

Trp Thr Gln Asp Arg Ala Lys Pro Val Thr Gln Ile Val Ser Ala Glu
225                 230                 235                 240

Ala Trp Gly Arg Ala Asp
                245

<210> SEQ ID NO 4
<211> LENGTH: 207
<212> TYPE: PRT
<213> ORGANISM: Homo sapiens

<400> SEQUENCE: 4

Lys Asn Gln Val Glu Gln Ser Pro Gln Ser Leu Ile Ile Leu Glu Gly
1               5                   10                  15

Lys Asn Cys Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
 50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Asn His Ser Gly
                 85                  90                  95

Gly Ser Tyr Ile Pro Thr Phe Gly Arg Gly Thr Ser Leu Ile Val His
            100                 105                 110

Pro Tyr Ile Gln Lys Pro Asp Pro Ala Val Tyr Gln Leu Arg Asp Ser
            115                 120                 125

Lys Ser Ser Asp Lys Ser Val Cys Leu Phe Thr Asp Phe Asp Ser Gln
            130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
```

```
                180                 185                 190
Ser Ile Ile Pro Glu Asp Thr Phe Phe Pro Ser Pro Glu Ser Ser
            195                 200                 205

<210> SEQ ID NO 5
<211> LENGTH: 246
<212> TYPE: PRT
<213> ORGANISM: Homo sapiens

<400> SEQUENCE: 5

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Phe Leu
                85                  90                  95

Met Thr Ser Gly Asp Pro Tyr Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Cys Thr Asp Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp
                245

<210> SEQ ID NO 6
<211> LENGTH: 6
<212> TYPE: PRT
<213> ORGANISM: Homo sapiens

<400> SEQUENCE: 6

Val Ser Pro Phe Ser Asn
1               5

<210> SEQ ID NO 7
<211> LENGTH: 7
<212> TYPE: PRT
<213> ORGANISM: Homo sapiens

<400> SEQUENCE: 7
```

Met Thr Phe Ser Glu Asn Thr
1               5

<210> SEQ ID NO 8
<211> LENGTH: 13
<212> TYPE: PRT
<213> ORGANISM: Homo sapiens

<400> SEQUENCE: 8

Val Val Asn His Ser Gly Gly Ser Tyr Ile Pro Thr Phe
1               5                   10

<210> SEQ ID NO 9
<211> LENGTH: 17
<212> TYPE: PRT
<213> ORGANISM: Homo sapiens

<400> SEQUENCE: 9

Leu Arg Trp Tyr Lys Gln Asp Thr Gly Arg Gly Pro Val Ser Leu Thr
1               5                   10                  15

Ile

<210> SEQ ID NO 10
<211> LENGTH: 34
<212> TYPE: PRT
<213> ORGANISM: Homo sapiens

<400> SEQUENCE: 10

Lys Ser Asn Gly Arg Tyr Thr Ala Thr Leu Asp Ala Asp Thr Lys Gln
1               5                   10                  15

Ser Ser Leu His Ile Thr Ala Ser Gln Leu Ser Asp Ser Ala Ser Tyr
                20                  25                  30

Ile Cys

<210> SEQ ID NO 11
<211> LENGTH: 5
<212> TYPE: PRT
<213> ORGANISM: Homo sapiens

<400> SEQUENCE: 11

Met Asp His Glu Asn
1               5

<210> SEQ ID NO 12
<211> LENGTH: 6
<212> TYPE: PRT
<213> ORGANISM: Homo sapiens

<400> SEQUENCE: 12

Ser Tyr Asp Val Lys Met
1               5

<210> SEQ ID NO 13
<211> LENGTH: 16
<212> TYPE: PRT
<213> ORGANISM: Homo sapiens

<400> SEQUENCE: 13

Ala Ser Ser Phe Leu Met Thr Ser Gly Asp Pro Tyr Glu Gln Tyr Phe
1               5                   10                  15

<210> SEQ ID NO 14

<211> LENGTH: 17
<212> TYPE: PRT
<213> ORGANISM: Homo sapiens

<400> SEQUENCE: 14

Met Phe Trp Tyr Arg Gln Asp Pro Gly Leu Gly Leu Arg Leu Ile Tyr
1               5                   10                  15

Phe

<210> SEQ ID NO 15
<211> LENGTH: 37
<212> TYPE: PRT
<213> ORGANISM: Homo sapiens

<400> SEQUENCE: 15

Lys Glu Lys Gly Asp Ile Pro Glu Gly Tyr Ser Val Ser Arg Glu Lys
1               5                   10                  15

Lys Glu Arg Phe Ser Leu Ile Leu Glu Ser Ala Ser Thr Asn Gln Thr
            20                  25                  30

Ser Met Tyr Leu Cys
        35

<210> SEQ ID NO 16
<211> LENGTH: 113
<212> TYPE: PRT
<213> ORGANISM: Artificial Sequence
<220> FEATURE:
<223> OTHER INFORMATION: mutant alpha chain (c19v)

<400> SEQUENCE: 16

Lys Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn His Ser Gly
                85                  90                  95

Gly Ser Tyr Ile Pro Thr Phe Gly Arg Gly Thr Ser Leu Ile Val His
            100                 105                 110

Pro

<210> SEQ ID NO 17
<211> LENGTH: 113
<212> TYPE: PRT
<213> ORGANISM: Artificial Sequence
<220> FEATURE:
<223> OTHER INFORMATION: mutant alpha chain (a7)

<400> SEQUENCE: 17

Lys Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Leu Asp Tyr Ala Ile Asn Thr Lys Ser Asn Gly Arg Tyr Thr Ala
          50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Asn His Ser Gly
                 85                  90                  95

Gly Ser Tyr Ile Pro Thr Phe Gly Arg Gly Thr Ser Leu Ile Val His
                100                 105                 110

Pro

<210> SEQ ID NO 18
<211> LENGTH: 113
<212> TYPE: PRT
<213> ORGANISM: Artificial Sequence
<220> FEATURE:
<223> OTHER INFORMATION: mutant alpha chain (a12)

<400> SEQUENCE: 18

Lys Asn Gln Val Glu Gln Ser Pro Gln Ser Leu Ile Ile Leu Glu Gly
 1               5                  10                  15

Lys Asn Val Thr Leu Gln Cys Asn Tyr Thr Val Ser Pro Phe Ser Asn
                 20                  25                  30

Leu Arg Trp Tyr Lys Gln Asp Thr Gly Arg Gly Pro Val Ser Leu Thr
             35                  40                  45

Ile Met Thr Phe Ser Glu Asn Thr Lys Ser Asn Gly Arg Tyr Thr Ala
          50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Asn Arg Ala Asp
                 85                  90                  95

Gly Leu Tyr Ile Pro Thr Phe Gly Arg Gly Thr Ser Leu Ile Val His
                100                 105                 110

Pro

<210> SEQ ID NO 19
<211> LENGTH: 113
<212> TYPE: PRT
<213> ORGANISM: Artificial Sequence
<220> FEATURE:
<223> OTHER INFORMATION: mutant alpha chain (a13)

<400> SEQUENCE: 19

Lys Asn Gln Val Glu Gln Ser Pro Gln Ser Leu Ile Ile Leu Glu Gly
 1               5                  10                  15

Lys Asn Val Thr Leu Gln Cys Asn Tyr Thr Val Ser Pro Phe Ser Asn
                 20                  25                  30

Leu Arg Trp Tyr Lys Gln Asp Thr Gly Arg Gly Pro Val Ser Leu Thr
             35                  40                  45

Ile Met Thr Phe Ser Glu Asn Thr Lys Ser Asn Gly Arg Tyr Thr Ala
          50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Asn Ser Ala Asn
                 85                  90                  95

Gly Leu Tyr Ile Pro Thr Phe Gly Arg Gly Thr Ser Leu Ile Val His
                100                 105                 110

-continued

Pro

<210> SEQ ID NO 20
<211> LENGTH: 113
<212> TYPE: PRT
<213> ORGANISM: Artificial Sequence
<220> FEATURE:
<223> OTHER INFORMATION: mutant alpha chain (a13ka)

<400> SEQUENCE: 20

Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn Ser Ala Asn
                85                  90                  95

Gly Leu Tyr Ile Pro Thr Phe Gly Arg Gly Thr Ser Leu Ile Val His
            100                 105                 110

Pro

<210> SEQ ID NO 21
<211> LENGTH: 113
<212> TYPE: PRT
<213> ORGANISM: Artificial Sequence
<220> FEATURE:
<223> OTHER INFORMATION: mutant alpha chain (a19)

<400> SEQUENCE: 21

Lys Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Leu Asp Tyr Ala Ile Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn Arg Ala Asp
                85                  90                  95

Gly Leu Tyr Ile Pro Thr Phe Gly Arg Gly Thr Ser Leu Ile Val His
            100                 105                 110

Pro

<210> SEQ ID NO 22
<211> LENGTH: 113
<212> TYPE: PRT
<213> ORGANISM: Artificial Sequence
<220> FEATURE:
<223> OTHER INFORMATION: mutant alpha chain (a19ka)

<400> SEQUENCE: 22

Ala Asn Gln Val Glu Gln Ser Pro Gln Ser Leu Ile Ile Leu Glu Gly

```
                1               5                   10                  15
        Lys Asn Val Thr Leu Gln Cys Asn Tyr Thr Val Ser Pro Phe Ser Asn
                        20                  25                  30

Leu Arg Trp Tyr Lys Gln Asp Thr Gly Arg Gly Pro Val Ser Leu Thr
                        35                  40                  45

Ile Leu Asp Tyr Ala Ile Asn Thr Lys Ser Asn Gly Arg Tyr Thr Ala
                        50                  55                  60

Thr Leu Asp Ala Asp Thr Lys Gln Ser Ser Leu His Ile Thr Ala Ser
         65                 70                  75                  80

Gln Leu Ser Asp Ser Ala Ser Tyr Ile Cys Val Val Asn Arg Ala Asp
                            85                  90                  95

Gly Leu Tyr Ile Pro Thr Phe Gly Arg Gly Thr Ser Leu Ile Val His
                            100                 105                 110

Pro
```

<210> SEQ ID NO 23
<211> LENGTH: 113
<212> TYPE: PRT
<213> ORGANISM: Artificial Sequence
<220> FEATURE:
<223> OTHER INFORMATION: mutant alpha chain (a13kaLS)

<400> SEQUENCE: 23

```
        Ala Asn Gln Val Glu Gln Ser Pro Gln Ser Leu Ile Ile Leu Glu Gly
         1               5                   10                  15

Lys Asn Val Thr Leu Gln Cys Asn Tyr Thr Val Ser Pro Phe Ser Asn
                        20                  25                  30

Leu Arg Trp Tyr Lys Gln Asp Thr Gly Arg Gly Pro Val Ser Leu Thr
                        35                  40                  45

Ile Leu Thr Phe Ser Glu Asn Thr Lys Ser Asn Gly Arg Tyr Thr Ala
                    50                  55                  60

Thr Leu Asp Ala Asp Thr Lys Gln Ser Ser Leu His Ile Thr Ala Ser
         65                 70                  75                  80

Gln Leu Ser Asp Ser Ala Ser Tyr Ile Cys Val Val Asn Ser Ala Ser
                            85                  90                  95

Gly Leu Tyr Ile Pro Thr Phe Gly Arg Gly Thr Ser Leu Ile Val His
                            100                 105                 110

Pro
```

<210> SEQ ID NO 24
<211> LENGTH: 113
<212> TYPE: PRT
<213> ORGANISM: Artificial Sequence
<220> FEATURE:
<223> OTHER INFORMATION: mutant alpha chain (a13kaLQ)

<400> SEQUENCE: 24

```
        Ala Asn Gln Val Glu Gln Ser Pro Gln Ser Leu Ile Ile Leu Glu Gly
         1               5                   10                  15

Lys Asn Val Thr Leu Gln Cys Asn Tyr Thr Val Ser Pro Phe Ser Asn
                        20                  25                  30

Leu Arg Trp Tyr Lys Gln Asp Thr Gly Arg Gly Pro Val Ser Leu Thr
                        35                  40                  45

Ile Leu Thr Phe Ser Glu Asn Thr Lys Ser Asn Gly Arg Tyr Thr Ala
                    50                  55                  60

Thr Leu Asp Ala Asp Thr Lys Gln Ser Ser Leu His Ile Thr Ala Ser
         65                 70                  75                  80
```

Gln Leu Ser Asp Ser Ala Ser Tyr Ile Cys Val Val Asn Ser Ala Gln
                85                  90                  95

Gly Leu Tyr Ile Pro Thr Phe Gly Arg Gly Thr Ser Leu Ile Val His
            100                 105                 110

Pro

<210> SEQ ID NO 25
<211> LENGTH: 116
<212> TYPE: PRT
<213> ORGANISM: Artificial Sequence
<220> FEATURE:
<223> OTHER INFORMATION: mutant beta chain (b1)

<400> SEQUENCE: 25

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 26
<211> LENGTH: 116
<212> TYPE: PRT
<213> ORGANISM: Artificial Sequence
<220> FEATURE:
<223> OTHER INFORMATION: mutant beta chain (b14)

<400> SEQUENCE: 26

Asp Val Lys Val Thr Gln Ser Ser Arg Tyr Leu Val Lys Arg Thr Gly
1               5                   10                  15

Glu Lys Val Phe Leu Glu Cys Val Gln Asp Ala Pro Leu Ser Lys Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 27

<211> LENGTH: 116
<212> TYPE: PRT
<213> ORGANISM: Artificial Sequence
<220> FEATURE:
<223> OTHER INFORMATION: mutant beta chain (b14L)

<400> SEQUENCE: 27

Asp Val Lys Val Thr Gln Ser Ser Arg Tyr Leu Val Lys Arg Thr Gly
1               5                   10                  15

Glu Lys Val Phe Leu Glu Cys Val Gln Asp Ala Pro Leu Ser Lys Met
            20                  25                  30

Phe Trp Tyr Arg Gln Asp Pro Gly Leu Gly Leu Arg Leu Ile Tyr Phe
        35                  40                  45

Ser Tyr Asp Val Lys Leu Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 28
<211> LENGTH: 116
<212> TYPE: PRT
<213> ORGANISM: Artificial Sequence
<220> FEATURE:
<223> OTHER INFORMATION: mutant beta chain (b21)

<400> SEQUENCE: 28

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Arg Phe Ala Thr Gly Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 29
<211> LENGTH: 116
<212> TYPE: PRT
<213> ORGANISM: Artificial Sequence
<220> FEATURE:
<223> OTHER INFORMATION: mutant beta chain (b21L)

<400> SEQUENCE: 29

Asp Val Lys Val Thr Gln Ser Ser Arg Tyr Leu Val Lys Arg Thr Gly
1               5                   10                  15

-continued

```
Glu Lys Val Phe Leu Glu Cys Val Gln Asp Leu Asp His Glu Asn Met
            20                  25                  30

Phe Trp Tyr Arg Gln Asp Pro Gly Leu Gly Leu Arg Leu Ile Tyr Phe
        35                  40                  45

Ser Arg Phe Ala Thr Gly Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 30
<211> LENGTH: 5
<212> TYPE: PRT
<213> ORGANISM: Artificial Sequence
<220> FEATURE:
<223> OTHER INFORMATION: Linker Sequence

<400> SEQUENCE: 30

Gly Gly Gly Gly Ser
1               5

<210> SEQ ID NO 31
<211> LENGTH: 5
<212> TYPE: PRT
<213> ORGANISM: Artificial Sequence
<220> FEATURE:
<223> OTHER INFORMATION: Linker Sequence

<400> SEQUENCE: 31

Gly Gly Gly Ser Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Linker Sequence

<400> SEQUENCE: 32

Gly Gly Ser Gly Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Linker Sequence

<400> SEQUENCE: 33

Gly Ser Gly Gly Gly
1               5

<210> SEQ ID NO 34
<211> LENGTH: 6
<212> TYPE: PRT
<213> ORGANISM: Artificial Sequence
<220> FEATURE:
```

```
<223> OTHER INFORMATION: Linker Sequence

<400> SEQUENCE: 34

Gly Ser Gly Gly Gly Pro
1               5

<210> SEQ ID NO 35
<211> LENGTH: 5
<212> TYPE: PRT
<213> ORGANISM: Artificial Sequence
<220> FEATURE:
<223> OTHER INFORMATION: Linker Sequence

<400> SEQUENCE: 35

Gly Gly Glu Pro Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Linker Sequence

<400> SEQUENCE: 36

Gly Gly Glu Gly Gly Gly Pro
1               5

<210> SEQ ID NO 37
<211> LENGTH: 12
<212> TYPE: PRT
<213> ORGANISM: Artificial Sequence
<220> FEATURE:
<223> OTHER INFORMATION: Linker Sequence

<400> SEQUENCE: 37

Gly Gly Glu Gly Gly Gly Ser Glu Gly Gly Ser
1               5                   10

<210> SEQ ID NO 38
<211> LENGTH: 199
<212> TYPE: PRT
<213> ORGANISM: Artificial Sequence
<220> FEATURE:
<223> OTHER INFORMATION: alpha chain (a19ka)

<400> SEQUENCE: 38

Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Leu Asp Tyr Ala Ile Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn Arg Ala Asp
                85                  90                  95

Gly Leu Tyr Ile Pro Thr Phe Gly Arg Gly Thr Ser Leu Ile Val His
            100                 105                 110

Pro Tyr Ile Gln Lys Pro Asp Pro Ala Val Tyr Gln Leu Arg Asp Ser
        115                 120                 125
```

Lys Ser Ser Asp Lys Ser Val Cys Leu Phe Thr Asp Phe Asp Ser Gln
    130             135                 140

Thr Asn Val Ser Gln Ser Lys Asp Ser Asp Val Tyr Ile Thr Asp Lys
145             150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
                180                 185                 190

Ser Ile Ile Pro Glu Asp Thr
        195

<210> SEQ ID NO 39
<211> LENGTH: 199
<212> TYPE: PRT
<213> ORGANISM: Artificial Sequence
<220> FEATURE:
<223> OTHER INFORMATION: alpha chain (a13ka)

<400> SEQUENCE: 39

Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
                20                  25                  30

Leu Arg Trp Tyr Lys Gln Asp Thr Gly Arg Gly Pro Val Ser Leu Thr
            35                  40                  45

Ile Met Thr Phe Ser Glu Asn Thr Lys Ser Asn Gly Arg Tyr Thr Ala
        50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn Ser Ala Asn
                85                  90                  95

Gly Leu Tyr Ile Pro Thr Phe Gly Arg Gly Thr Ser Leu Ile Val His
                100                 105                 110

Pro Tyr Ile Gln Lys Pro Asp Pro Ala Val Tyr Gln Leu Arg Asp Ser
            115                 120                 125

Lys Ser Ser Asp Lys Ser Val Cys Leu Phe Thr Asp Phe Asp Ser Gln
    130             135                 140

Thr Asn Val Ser Gln Ser Lys Asp Ser Asp Val Tyr Ile Thr Asp Lys
145             150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
                180                 185                 190

Ser Ile Ile Pro Glu Asp Thr
        195

<210> SEQ ID NO 40
<211> LENGTH: 199
<212> TYPE: PRT
<213> ORGANISM: Artificial Sequence
<220> FEATURE:
<223> OTHER INFORMATION: alpha chain (a13kaLQ)

<400> SEQUENCE: 40

Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn

```
            20                  25                  30
Leu Arg Trp Tyr Lys Gln Asp Thr Gly Arg Gly Pro Val Ser Leu Thr
        35                  40                  45

Ile Leu Thr Phe Ser Glu Asn Thr Lys Ser Asn Gly Arg Tyr Thr Ala
 50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Asn Ser Ala Gln
                85                  90                  95

Gly Leu Tyr Ile Pro Thr Phe Gly Arg Gly Thr Ser Leu Ile Val His
            100                 105                 110

Pro Tyr Ile Gln Lys Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr
        195

<210> SEQ ID NO 41
<211> LENGTH: 199
<212> TYPE: PRT
<213> ORGANISM: Artificial Sequence
<220> FEATURE:
<223> OTHER INFORMATION: alpha chain (a13kaLS)

<400> SEQUENCE: 41

Ala Asn Gln Val Glu Gln Ser Pro Gln Ser Leu Ile Ile Leu Glu Gly
 1               5                  10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Leu Thr Phe Ser Glu Asn Thr Lys Ser Asn Gly Arg Tyr Thr Ala
 50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Asn Ser Ala Ser
                85                  90                  95

Gly Leu Tyr Ile Pro Thr Phe Gly Arg Gly Thr Ser Leu Ile Val His
            100                 105                 110

Pro Tyr Ile Gln Lys Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
```

```
                    180                 185                 190

Ser Ile Ile Pro Glu Asp Thr
        195

<210> SEQ ID NO 42
<211> LENGTH: 504
<212> TYPE: PRT
<213> ORGANISM: Artificial Sequence
<220> FEATURE:
<223> OTHER INFORMATION: beta chain (b14)

<400> SEQUENCE: 42

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255

Gly Ser Asp Val Lys Val Thr Gln Ser Ser Arg Tyr Leu Val Lys Arg
            260                 265                 270

Thr Gly Glu Lys Val Phe Leu Glu Cys Val Gln Asp Ala Pro Leu Ser
        275                 280                 285

Lys Met Phe Trp Tyr Arg Gln Asp Pro Gly Leu Gly Leu Arg Leu Ile
    290                 295                 300

Tyr Phe Ser Tyr Asp Val Lys Met Lys Glu Lys Gly Asp Ile Pro Glu
305                 310                 315                 320

Gly Tyr Ser Val Ser Arg Glu Lys Lys Glu Arg Phe Ser Leu Ile Leu
                325                 330                 335

Glu Ser Ala Ser Thr Asn Gln Thr Ser Met Tyr Leu Cys Ala Ser Ser
```

```
            340                 345                 350
Ser Asp Gln Asn Ser Gly Asp Pro Tyr Glu Gln Tyr Phe Gly Pro Gly
                355                 360                 365

Thr Arg Leu Thr Val Thr Glu Asp Leu Lys Asn Val Phe Pro Pro Glu
            370                 375                 380

Val Ala Val Phe Glu Pro Ser Glu Ala Glu Ile Ser His Thr Gln Lys
385                 390                 395                 400

Ala Thr Leu Val Cys Leu Ala Thr Gly Phe Tyr Pro Asp His Val Glu
                405                 410                 415

Leu Ser Trp Trp Val Asn Gly Lys Glu Val His Ser Gly Val Cys Thr
            420                 425                 430

Asp Pro Gln Pro Leu Lys Glu Gln Pro Ala Leu Asn Asp Ser Arg Tyr
                435                 440                 445

Ala Leu Ser Ser Arg Leu Arg Val Ser Ala Thr Phe Trp Gln Asp Pro
            450                 455                 460

Arg Asn His Phe Arg Cys Gln Val Gln Phe Tyr Gly Leu Ser Glu Asn
465                 470                 475                 480

Asp Glu Trp Thr Gln Asp Arg Ala Lys Pro Val Thr Gln Ile Val Ser
                485                 490                 495

Ala Glu Ala Trp Gly Arg Ala Asp
            500

<210> SEQ ID NO 43
<211> LENGTH: 504
<212> TYPE: PRT
<213> ORGANISM: Artificial Sequence
<220> FEATURE:
<223> OTHER INFORMATION: beta chain (b14L)

<400> SEQUENCE: 43

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
```

```
                195                 200                 205
Thr Ala Tyr Leu Gln Met Asn Ser Leu Arg Ala Glu Asp Thr Ala Val
210                 215                 220
Tyr Tyr Cys Ala Arg Ser Gly Tyr Tyr Gly Asp Ser Asp Trp Tyr Phe
225                 230                 235                 240
Asp Val Trp Gly Gln Gly Thr Leu Val Thr Val Ser Ser Gly Gly Gly
                245                 250                 255
Gly Ser Asp Val Lys Val Thr Gln Ser Ser Arg Tyr Leu Val Lys Arg
            260                 265                 270
Thr Gly Glu Lys Val Phe Leu Glu Cys Val Gln Asp Ala Pro Leu Ser
        275                 280                 285
Lys Met Phe Trp Tyr Arg Gln Asp Pro Gly Leu Gly Leu Arg Leu Ile
    290                 295                 300
Tyr Phe Ser Tyr Asp Val Lys Leu Lys Glu Lys Gly Asp Ile Pro Glu
305                 310                 315                 320
Gly Tyr Ser Val Ser Arg Glu Lys Lys Glu Arg Phe Ser Leu Ile Leu
                325                 330                 335
Glu Ser Ala Ser Thr Asn Gln Thr Ser Met Tyr Leu Cys Ala Ser Ser
            340                 345                 350
Ser Asp Gln Asn Ser Gly Asp Pro Tyr Glu Gln Tyr Phe Gly Pro Gly
        355                 360                 365
Thr Arg Leu Thr Val Thr Glu Asp Leu Lys Asn Val Phe Pro Pro Glu
    370                 375                 380
Val Ala Val Phe Glu Pro Ser Glu Ala Glu Ile Ser His Thr Gln Lys
385                 390                 395                 400
Ala Thr Leu Val Cys Leu Ala Thr Gly Phe Tyr Pro Asp His Val Glu
                405                 410                 415
Leu Ser Trp Trp Val Asn Gly Lys Glu Val His Ser Gly Val Cys Thr
            420                 425                 430
Asp Pro Gln Pro Leu Lys Glu Gln Pro Ala Leu Asn Asp Ser Arg Tyr
        435                 440                 445
Ala Leu Ser Ser Arg Leu Arg Val Ser Ala Thr Phe Trp Gln Asp Pro
    450                 455                 460
Arg Asn His Phe Arg Cys Gln Val Gln Phe Tyr Gly Leu Ser Glu Asn
465                 470                 475                 480
Asp Glu Trp Thr Gln Asp Arg Ala Lys Pro Val Thr Gln Ile Val Ser
                485                 490                 495
Ala Glu Ala Trp Gly Arg Ala Asp
            500

<210> SEQ ID NO 44
<211> LENGTH: 504
<212> TYPE: PRT
<213> ORGANISM: Artificial Sequence
<220> FEATURE:
<223> OTHER INFORMATION: beta chain (b21)

<400> SEQUENCE: 44

Ala Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Arg Asn Tyr
            20                  25                  30
Leu Asn Trp Tyr Gln Gln Lys Pro Gly Lys Ala Pro Lys Leu Leu Ile
        35                  40                  45
Tyr Tyr Thr Ser Arg Leu Glu Ser Gly Val Pro Ser Arg Phe Ser Gly
```

```
            50                  55                  60
Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                     85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Gly Gly Gly Gly Ser Gly
                115                 120                 125

Gly Gly Ser Glu Val Gln Leu Val Glu Ser Gly Gly Leu Val Gln
130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
                180                 185                 190

Gln Lys Phe Lys Asp Arg Phe Thr Ile Ser Val Asp Lys Ser Lys Asn
                195                 200                 205

Thr Ala Tyr Leu Gln Met Asn Ser Leu Arg Ala Glu Asp Thr Ala Val
210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255

Gly Ser Asp Val Lys Val Thr Gln Ser Ser Arg Tyr Leu Val Lys Arg
                260                 265                 270

Thr Gly Glu Lys Val Phe Leu Glu Cys Val Gln Asp Met Asp His Glu
                275                 280                 285

Asn Met Phe Trp Tyr Arg Gln Asp Pro Gly Leu Gly Leu Arg Leu Ile
290                 295                 300

Tyr Phe Ser Arg Phe Ala Thr Gly Lys Glu Lys Gly Asp Ile Pro Glu
305                 310                 315                 320

Gly Tyr Ser Val Ser Arg Glu Lys Lys Glu Arg Phe Ser Leu Ile Leu
                325                 330                 335

Glu Ser Ala Ser Thr Asn Gln Thr Ser Met Tyr Leu Cys Ala Ser Ser
                340                 345                 350

Ser Asp Gln Asn Ser Gly Asp Pro Tyr Glu Gln Tyr Phe Gly Pro Gly
                355                 360                 365

Thr Arg Leu Thr Val Thr Glu Asp Leu Lys Asn Val Phe Pro Pro Glu
370                 375                 380

Val Ala Val Phe Glu Pro Ser Glu Ala Glu Ile Ser His Thr Gln Lys
385                 390                 395                 400

Ala Thr Leu Val Cys Leu Ala Thr Gly Phe Tyr Pro Asp His Val Glu
                405                 410                 415

Leu Ser Trp Trp Val Asn Gly Lys Glu Val His Ser Gly Val Cys Thr
                420                 425                 430

Asp Pro Gln Pro Leu Lys Glu Gln Pro Ala Leu Asn Asp Ser Arg Tyr
                435                 440                 445

Ala Leu Ser Ser Arg Leu Arg Val Ser Ala Thr Phe Trp Gln Asp Pro
450                 455                 460

Arg Asn His Phe Arg Cys Gln Val Gln Phe Tyr Gly Leu Ser Glu Asn
465                 470                 475                 480
```

-continued

```
Asp Glu Trp Thr Gln Asp Arg Ala Lys Pro Val Thr Gln Ile Val Ser
            485                 490                 495

Ala Glu Ala Trp Gly Arg Ala Asp
            500

<210> SEQ ID NO 45
<211> LENGTH: 504
<212> TYPE: PRT
<213> ORGANISM: Artificial Sequence
<220> FEATURE:
<223> OTHER INFORMATION: beta chain (b21L)

<400> SEQUENCE: 45

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255

Gly Ser Asp Val Lys Val Thr Gln Ser Ser Arg Tyr Leu Val Lys Arg
            260                 265                 270

Thr Gly Glu Lys Val Phe Leu Glu Cys Val Gln Asp Leu Asp His Glu
        275                 280                 285

Asn Met Phe Trp Tyr Arg Gln Asp Pro Gly Leu Gly Leu Arg Leu Ile
    290                 295                 300

Tyr Phe Ser Arg Phe Ala Thr Gly Lys Glu Lys Gly Asp Ile Pro Glu
305                 310                 315                 320

Gly Tyr Ser Val Ser Arg Glu Lys Lys Glu Arg Phe Ser Leu Ile Leu
                325                 330                 335
```

-continued

```
Glu Ser Ala Ser Thr Asn Gln Thr Ser Met Tyr Leu Cys Ala Ser Ser
                340                 345                 350

Ser Asp Gln Asn Ser Gly Asp Pro Tyr Glu Gln Tyr Phe Gly Pro Gly
            355                 360                 365

Thr Arg Leu Thr Val Thr Glu Asp Leu Lys Asn Val Phe Pro Pro Glu
        370                 375                 380

Val Ala Val Phe Glu Pro Ser Glu Ala Glu Ile Ser His Thr Gln Lys
385                 390                 395                 400

Ala Thr Leu Val Cys Leu Ala Thr Gly Phe Tyr Pro Asp His Val Glu
                405                 410                 415

Leu Ser Trp Trp Val Asn Gly Lys Glu Val His Ser Gly Val Cys Thr
            420                 425                 430

Asp Pro Gln Pro Leu Lys Glu Gln Pro Ala Leu Asn Asp Ser Arg Tyr
        435                 440                 445

Ala Leu Ser Ser Arg Leu Arg Val Ser Ala Thr Phe Trp Gln Asp Pro
    450                 455                 460

Arg Asn His Phe Arg Cys Gln Val Gln Phe Tyr Gly Leu Ser Glu Asn
465                 470                 475                 480

Asp Glu Trp Thr Gln Asp Arg Ala Lys Pro Val Thr Gln Ile Val Ser
                485                 490                 495

Ala Glu Ala Trp Gly Arg Ala Asp
            500
```

<210> SEQ ID NO 46
<211> LENGTH: 113
<212> TYPE: PRT
<213> ORGANISM: Artificial Sequence
<220> FEATURE:
<223> OTHER INFORMATION: mutant alpha chain (a36)

<400> SEQUENCE: 46

```
Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn Ser Ala Gln
                85                  90                  95

Gly Leu Tyr Ile Pro Thr Phe Gly Arg Gly Thr Ser Leu Ile Val His
            100                 105                 110

Pro
```

<210> SEQ ID NO 47
<211> LENGTH: 113
<212> TYPE: PRT
<213> ORGANISM: Artificial Sequence
<220> FEATURE:
<223> OTHER INFORMATION: mutant alpha chain (a37)

<400> SEQUENCE: 47

```
Ala Asn Gln Val Glu Gln Ser Pro Gln Ser Leu Ile Ile Leu Glu Gly
1               5                   10                  15
```

```
Lys Asn Val Thr Leu Gln Cys Asn Tyr Thr Val Ser Pro Phe Ser Asn
                20                  25                  30

Leu Arg Trp Tyr Lys Gln Asp Thr Gly Arg Gly Pro Val Ser Leu Thr
            35                  40                  45

Ile Leu Thr Tyr Ser Glu Asn Thr Lys Ser Asn Gly Arg Tyr Thr Ala
        50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn Ser Ala Gln
                85                  90                  95

Gly Leu Tyr Ile Pro Thr Phe Gly Arg Gly Thr Ser Leu Ile Val His
                100                 105                 110

Pro

<210> SEQ ID NO 48
<211> LENGTH: 113
<212> TYPE: PRT
<213> ORGANISM: Artificial Sequence
<220> FEATURE:
<223> OTHER INFORMATION: mutant alpha chain (a38)

<400> SEQUENCE: 48

Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
                20                  25                  30

Leu Arg Trp Tyr Lys Gln Asp Thr Gly Arg Gly Pro Val Ser Leu Thr
            35                  40                  45

Ile Leu Thr Phe Ser Glu Asn Thr Lys Ser Asn Gly Arg Tyr Thr Ala
        50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn His Ala Gln
                85                  90                  95

Gly Leu Tyr Ile Pro Thr Phe Gly Arg Gly Thr Ser Leu Ile Val His
                100                 105                 110

Pro

<210> SEQ ID NO 49
<211> LENGTH: 113
<212> TYPE: PRT
<213> ORGANISM: Artificial Sequence
<220> FEATURE:
<223> OTHER INFORMATION: mutant alpha chain (a39)

<400> SEQUENCE: 49

Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
                20                  25                  30

Leu Arg Trp Tyr Lys Gln Asp Thr Gly Arg Gly Pro Val Ser Leu Thr
            35                  40                  45

Ile Leu Thr Phe Ser Glu Asn Thr Lys Ser Asn Gly Arg Tyr Thr Ala
        50                  55                  60

Thr Leu Asp Ala Asp Thr Lys Gln Ser Ser Leu His Ile Thr Ala Ser
65                  70                  75                  80
```

-continued

```
Gln Leu Ser Asp Ser Ala Ser Tyr Ile Cys Val Val Asn Ser Ser Gln
                85                  90                  95

Gly Leu Tyr Ile Pro Thr Phe Gly Arg Gly Thr Ser Leu Ile Val His
            100                 105                 110
Pro

<210> SEQ ID NO 50
<211> LENGTH: 113
<212> TYPE: PRT
<213> ORGANISM: Artificial Sequence
<220> FEATURE:
<223> OTHER INFORMATION: mutant alpha chain (a40)

<400> SEQUENCE: 50

Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Leu Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn Ser Ala Gly
                85                  90                  95

Gly Leu Tyr Ile Pro Thr Phe Gly Arg Gly Thr Ser Leu Ile Val His
            100                 105                 110
Pro

<210> SEQ ID NO 51
<211> LENGTH: 113
<212> TYPE: PRT
<213> ORGANISM: Artificial Sequence
<220> FEATURE:
<223> OTHER INFORMATION: mutant alpha chain (a41)

<400> SEQUENCE: 51

Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Leu Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn Ser Ala Gln
                85                  90                  95

Gly Ser Tyr Ile Pro Thr Phe Gly Arg Gly Thr Ser Leu Ile Val His
            100                 105                 110
Pro

<210> SEQ ID NO 52
<211> LENGTH: 113
<212> TYPE: PRT
<213> ORGANISM: Artificial Sequence
```

<220> FEATURE:
<223> OTHER INFORMATION: mutant alpha chain (a30)

<400> SEQUENCE: 52

```
Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Asp Tyr Ala Ile Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn Arg Ala Asp
                85                  90                  95

Gly Leu Tyr Ile Pro Thr Phe Gly Arg Gly Thr Ser Leu Ile Val His
            100                 105                 110

Pro
```

<210> SEQ ID NO 53
<211> LENGTH: 113
<212> TYPE: PRT
<213> ORGANISM: Artificial Sequence
<220> FEATURE:
<223> OTHER INFORMATION: mutant alpha chain (a42)

<400> SEQUENCE: 53

```
Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Leu Thr Tyr Ala Ile Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn Arg Ala Asp
                85                  90                  95

Gly Leu Tyr Ile Pro Thr Phe Gly Arg Gly Thr Ser Leu Ile Val His
            100                 105                 110

Pro
```

<210> SEQ ID NO 54
<211> LENGTH: 113
<212> TYPE: PRT
<213> ORGANISM: Artificial Sequence
<220> FEATURE:
<223> OTHER INFORMATION: mutant alpha chain (a31)

<400> SEQUENCE: 54

```
Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45
```

```
Ile Leu Asp Phe Ala Ile Asn Thr Lys Ser Asn Gly Arg Tyr Thr Ala
     50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Asn Arg Ala Asp
                 85                  90                  95

Gly Leu Tyr Ile Pro Thr Phe Gly Arg Gly Thr Ser Leu Ile Val His
                100                 105                 110

Pro
```

<210> SEQ ID NO 55
<211> LENGTH: 113
<212> TYPE: PRT
<213> ORGANISM: Artificial Sequence
<220> FEATURE:
<223> OTHER INFORMATION: mutant alpha chain (a43)

<400> SEQUENCE: 55

```
Ala Asn Gln Val Glu Gln Ser Pro Gln Ser Leu Ile Ile Leu Glu Gly
  1               5                  10                  15

Lys Asn Val Thr Leu Gln Cys Asn Tyr Thr Val Ser Pro Phe Ser Asn
                 20                  25                  30

Leu Arg Trp Tyr Lys Gln Asp Thr Gly Arg Gly Pro Val Ser Leu Thr
             35                  40                  45

Ile Leu Asp Tyr Ser Ile Asn Thr Lys Ser Asn Gly Arg Tyr Thr Ala
     50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Asn Arg Ala Asp
                 85                  90                  95

Gly Leu Tyr Ile Pro Thr Phe Gly Arg Gly Thr Ser Leu Ile Val His
                100                 105                 110

Pro
```

<210> SEQ ID NO 56
<211> LENGTH: 113
<212> TYPE: PRT
<213> ORGANISM: Artificial Sequence
<220> FEATURE:
<223> OTHER INFORMATION: mutant alpha chain (a32)

<400> SEQUENCE: 56

```
Ala Asn Gln Val Glu Gln Ser Pro Gln Ser Leu Ile Ile Leu Glu Gly
  1               5                  10                  15

Lys Asn Val Thr Leu Gln Cys Asn Tyr Thr Val Ser Pro Phe Ser Asn
                 20                  25                  30

Leu Arg Trp Tyr Lys Gln Asp Thr Gly Arg Gly Pro Val Ser Leu Thr
             35                  40                  45

Ile Leu Asp Tyr Ala Glu Asn Thr Lys Ser Asn Gly Arg Tyr Thr Ala
     50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Asn Arg Ala Asp
                 85                  90                  95

Gly Leu Tyr Ile Pro Thr Phe Gly Arg Gly Thr Ser Leu Ile Val His
                100                 105                 110
```

Pro

<210> SEQ ID NO 57
<211> LENGTH: 113
<212> TYPE: PRT
<213> ORGANISM: Artificial Sequence
<220> FEATURE:
<223> OTHER INFORMATION: mutant alpha chain (a44)

<400> SEQUENCE: 57

```
Ala Asn Gln Val Glu Gln Ser Pro Gln Ser Leu Ile Ile Leu Glu Gly
1               5                   10                  15
Lys Asn Val Thr Leu Gln Cys Asn Tyr Thr Val Ser Pro Phe Ser Asn
            20                  25                  30
Leu Arg Trp Tyr Lys Gln Asp Thr Gly Arg Gly Pro Val Ser Leu Thr
        35                  40                  45
Ile Leu Asp Tyr Ala Ile Asn Thr Lys Ser Asn Gly Arg Tyr Thr Ala
    50                  55                  60
Thr Leu Asp Ala Asp Thr Lys Gln Ser Ser Leu His Ile Thr Ala Ser
65                  70                  75                  80
Gln Leu Ser Asp Ser Ala Ser Tyr Ile Cys Val Val Asn His Ala Asp
                85                  90                  95
Gly Leu Tyr Ile Pro Thr Phe Gly Arg Gly Thr Ser Leu Ile Val His
                100                 105                 110
Pro
```

<210> SEQ ID NO 58
<211> LENGTH: 113
<212> TYPE: PRT
<213> ORGANISM: Artificial Sequence
<220> FEATURE:
<223> OTHER INFORMATION: mutant alpha chain (a33)

<400> SEQUENCE: 58

```
Ala Asn Gln Val Glu Gln Ser Pro Gln Ser Leu Ile Ile Leu Glu Gly
1               5                   10                  15
Lys Asn Val Thr Leu Gln Cys Asn Tyr Thr Val Ser Pro Phe Ser Asn
            20                  25                  30
Leu Arg Trp Tyr Lys Gln Asp Thr Gly Arg Gly Pro Val Ser Leu Thr
        35                  40                  45
Ile Leu Asp Tyr Ala Ile Asn Thr Lys Ser Asn Gly Arg Tyr Thr Ala
    50                  55                  60
Thr Leu Asp Ala Asp Thr Lys Gln Ser Ser Leu His Ile Thr Ala Ser
65                  70                  75                  80
Gln Leu Ser Asp Ser Ala Ser Tyr Ile Cys Val Val Asn Arg Ser Asp
                85                  90                  95
Gly Leu Tyr Ile Pro Thr Phe Gly Arg Gly Thr Ser Leu Ile Val His
                100                 105                 110
Pro
```

<210> SEQ ID NO 59
<211> LENGTH: 113
<212> TYPE: PRT
<213> ORGANISM: Artificial Sequence
<220> FEATURE:
<223> OTHER INFORMATION: mutant alpha chain (a45)

<400> SEQUENCE: 59

```
Ala Asn Gln Val Glu Gln Ser Pro Gln Ser Leu Ile Ile Leu Glu Gly
```

```
                1               5                  10                  15
            Lys Asn Val Thr Leu Gln Cys Asn Tyr Thr Val Ser Pro Phe Ser Asn
                           20                  25                  30

Leu Arg Trp Tyr Lys Gln Asp Thr Gly Arg Gly Pro Val Ser Leu Thr
                           35                  40                  45

Ile Leu Asp Tyr Ala Ile Asn Thr Lys Ser Asn Gly Arg Tyr Thr Ala
                       50                  55                  60

Thr Leu Asp Ala Asp Thr Lys Gln Ser Ser Leu His Ile Thr Ala Ser
            65                  70                  75                  80

Gln Leu Ser Asp Ser Ala Ser Tyr Ile Cys Val Val Asn Arg Ala Gly
                               85                  90                  95

Gly Leu Tyr Ile Pro Thr Phe Gly Arg Gly Thr Ser Leu Ile Val His
                               100                 105                 110

Pro

<210> SEQ ID NO 60
<211> LENGTH: 113
<212> TYPE: PRT
<213> ORGANISM: Artificial Sequence
<220> FEATURE:
<223> OTHER INFORMATION: mutant alpha chain (a34)

<400> SEQUENCE: 60

Ala Asn Gln Val Glu Gln Ser Pro Gln Ser Leu Ile Ile Leu Glu Gly
            1               5                  10                  15

Lys Asn Val Thr Leu Gln Cys Asn Tyr Thr Val Ser Pro Phe Ser Asn
                           20                  25                  30

Leu Arg Trp Tyr Lys Gln Asp Thr Gly Arg Gly Pro Val Ser Leu Thr
                           35                  40                  45

Ile Leu Asp Tyr Ala Ile Asn Thr Lys Ser Asn Gly Arg Tyr Thr Ala
                       50                  55                  60

Thr Leu Asp Ala Asp Thr Lys Gln Ser Ser Leu His Ile Thr Ala Ser
            65                  70                  75                  80

Gln Leu Ser Asp Ser Ala Ser Tyr Ile Cys Val Val Asn Arg Ala Asp
                               85                  90                  95

Gly Ser Tyr Ile Pro Thr Phe Gly Arg Gly Thr Ser Leu Ile Val His
                               100                 105                 110

Pro

<210> SEQ ID NO 61
<211> LENGTH: 113
<212> TYPE: PRT
<213> ORGANISM: Artificial Sequence
<220> FEATURE:
<223> OTHER INFORMATION: mutant alpha chain (aWTka)

<400> SEQUENCE: 61

Ala Asn Gln Val Glu Gln Ser Pro Gln Ser Leu Ile Ile Leu Glu Gly
            1               5                  10                  15

Lys Asn Val Thr Leu Gln Cys Asn Tyr Thr Val Ser Pro Phe Ser Asn
                           20                  25                  30

Leu Arg Trp Tyr Lys Gln Asp Thr Gly Arg Gly Pro Val Ser Leu Thr
                           35                  40                  45

Ile Met Thr Phe Ser Glu Asn Thr Lys Ser Asn Gly Arg Tyr Thr Ala
                       50                  55                  60

Thr Leu Asp Ala Asp Thr Lys Gln Ser Ser Leu His Ile Thr Ala Ser
            65                  70                  75                  80
```

Gln Leu Ser Asp Ser Ala Ser Tyr Ile Cys Val Val Asn His Ser Gly
                85                  90                  95

Gly Ser Tyr Ile Pro Thr Phe Gly Arg Gly Thr Ser Leu Ile Val His
                100                 105                 110

Pro

<210> SEQ ID NO 62
<211> LENGTH: 113
<212> TYPE: PRT
<213> ORGANISM: Artificial Sequence
<220> FEATURE:
<223> OTHER INFORMATION: mutant alpha chain (aM50L)

<400> SEQUENCE: 62

Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
                20                  25                  30

Leu Arg Trp Tyr Lys Gln Asp Thr Gly Arg Gly Pro Val Ser Leu Thr
                35                  40                  45

Ile Leu Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn His Ser Gly
                85                  90                  95

Gly Ser Tyr Ile Pro Thr Phe Gly Arg Gly Thr Ser Leu Ile Val His
                100                 105                 110

Pro

<210> SEQ ID NO 63
<211> LENGTH: 113
<212> TYPE: PRT
<213> ORGANISM: Artificial Sequence
<220> FEATURE:
<223> OTHER INFORMATION: mutant alpha chain (aS95A)

<400> SEQUENCE: 63

Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
                20                  25                  30

Leu Arg Trp Tyr Lys Gln Asp Thr Gly Arg Gly Pro Val Ser Leu Thr
                35                  40                  45

Ile Met Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn His Ala Gly
                85                  90                  95

Gly Ser Tyr Ile Pro Thr Phe Gly Arg Gly Thr Ser Leu Ile Val His
                100                 105                 110

Pro

<210> SEQ ID NO 64
<211> LENGTH: 113
<212> TYPE: PRT

-continued

<213> ORGANISM: Artificial Sequence
<220> FEATURE:
<223> OTHER INFORMATION: mutant alpha chain (aS98L)

<400> SEQUENCE: 64

```
Ala Asn Gln Val Glu Gln Ser Pro Gln Ser Leu Ile Ile Leu Glu Gly
1               5                   10                  15

Lys Asn Val Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Asn His Ser Gly
                85                  90                  95

Gly Leu Tyr Ile Pro Thr Phe Gly Arg Gly Thr Ser Leu Ile Val His
            100                 105                 110

Pro
```

<210> SEQ ID NO 65
<211> LENGTH: 116
<212> TYPE: PRT
<213> ORGANISM: Artificial Sequence
<220> FEATURE:
<223> OTHER INFORMATION: mutant beta chain (b41)

<400> SEQUENCE: 65

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Arg Phe Ala Thr Gly Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Gln Tyr Phe Gly Pro Gly Thr Arg
            100                 105                 110

Leu Thr Val Thr
        115
```

<210> SEQ ID NO 66
<211> LENGTH: 116
<212> TYPE: PRT
<213> ORGANISM: Artificial Sequence
<220> FEATURE:
<223> OTHER INFORMATION: mutant beta chain (b42)

<400> SEQUENCE: 66

```
Asp Val Lys Val Thr Gln Ser Ser Arg Tyr Leu Val Lys Arg Thr Gly
1               5                   10                  15

Glu Lys Val Phe Leu Glu Cys Val Gln Asp Leu Asp His Glu Asn Met
            20                  25                  30
```

```
Phe Trp Tyr Arg Gln Asp Pro Gly Leu Gly Leu Arg Leu Ile Tyr Phe
             35                  40                  45

Ser Tyr Phe Ala Thr Gly Lys Glu Lys Gly Asp Ile Pro Glu Gly Tyr
 50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                 85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 67
<211> LENGTH: 116
<212> TYPE: PRT
<213> ORGANISM: Artificial Sequence
<220> FEATURE:
<223> OTHER INFORMATION: mutant beta chain (b43)

<400> SEQUENCE: 67

Asp Val Lys Val Thr Gln Ser Ser Arg Tyr Leu Val Lys Arg Thr Gly
1               5                  10                  15

Glu Lys Val Phe Leu Glu Cys Val Gln Asp Leu Asp His Glu Asn Met
             20                  25                  30

Phe Trp Tyr Arg Gln Asp Pro Gly Leu Gly Leu Arg Leu Ile Tyr Phe
             35                  40                  45

Ser Arg Asp Ala Thr Gly Lys Glu Lys Gly Asp Ile Pro Glu Gly Tyr
 50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                 85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 68
<211> LENGTH: 116
<212> TYPE: PRT
<213> ORGANISM: Artificial Sequence
<220> FEATURE:
<223> OTHER INFORMATION: mutant beta chain (b44)

<400> SEQUENCE: 68

Asp Val Lys Val Thr Gln Ser Ser Arg Tyr Leu Val Lys Arg Thr Gly
1               5                  10                  15

Glu Lys Val Phe Leu Glu Cys Val Gln Asp Leu Asp His Glu Asn Met
             20                  25                  30

Phe Trp Tyr Arg Gln Asp Pro Gly Leu Gly Leu Arg Leu Ile Tyr Phe
             35                  40                  45

Ser Arg Phe Val Thr Gly Lys Glu Lys Gly Asp Ile Pro Glu Gly Tyr
 50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                 85                  90                  95
```

-continued

Gln Asn Ser Gly Asp Pro Tyr Glu Gln Tyr Phe Gly Pro Gly Thr Arg
            100                 105                 110

Leu Thr Val Thr
        115

<210> SEQ ID NO 69
<211> LENGTH: 116
<212> TYPE: PRT
<213> ORGANISM: Artificial Sequence
<220> FEATURE:
<223> OTHER INFORMATION: mutant beta chain (b45)

<400> SEQUENCE: 69

Asp Val Lys Val Thr Gln Ser Ser Arg Tyr Leu Val Lys Arg Thr Gly
1               5                   10                  15

Glu Lys Val Phe Leu Glu Cys Val Gln Asp Leu Asp His Glu Asn Met
            20                  25                  30

Phe Trp Tyr Arg Gln Asp Pro Gly Leu Gly Leu Arg Leu Ile Tyr Phe
        35                  40                  45

Ser Arg Phe Ala Lys Gly Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 70
<211> LENGTH: 116
<212> TYPE: PRT
<213> ORGANISM: Artificial Sequence
<220> FEATURE:
<223> OTHER INFORMATION: mutant beta chain (b46)

<400> SEQUENCE: 70

Asp Val Lys Val Thr Gln Ser Ser Arg Tyr Leu Val Lys Arg Thr Gly
1               5                   10                  15

Glu Lys Val Phe Leu Glu Cys Val Gln Asp Leu Asp His Glu Asn Met
            20                  25                  30

Phe Trp Tyr Arg Gln Asp Pro Gly Leu Gly Leu Arg Leu Ile Tyr Phe
        35                  40                  45

Ser Arg Phe Ala Thr Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 71
<211> LENGTH: 116
<212> TYPE: PRT

<213> ORGANISM: Artificial Sequence
<220> FEATURE:
<223> OTHER INFORMATION: mutant beta chain (b32)

<400> SEQUENCE: 71

Asp Val Lys Val Thr Gln Ser Ser Arg Tyr Leu Val Lys Arg Thr Gly
1               5                   10                  15

Glu Lys Val Phe Leu Glu Cys Val Gln Asp Met Pro Leu Ser Lys Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 72
<211> LENGTH: 116
<212> TYPE: PRT
<213> ORGANISM: Artificial Sequence
<220> FEATURE:
<223> OTHER INFORMATION: mutant beta chain (b33)

<400> SEQUENCE: 72

Asp Val Lys Val Thr Gln Ser Ser Arg Tyr Leu Val Lys Arg Thr Gly
1               5                   10                  15

Glu Lys Val Phe Leu Glu Cys Val Gln Asp Ala Asp Leu Ser Lys Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
        115

<210> SEQ ID NO 73
<211> LENGTH: 116
<212> TYPE: PRT
<213> ORGANISM: Artificial Sequence
<220> FEATURE:
<223> OTHER INFORMATION: mutant beta chain (b34)

<400> SEQUENCE: 73

Asp Val Lys Val Thr Gln Ser Ser Arg Tyr Leu Val Lys Arg Thr Gly
1               5                   10                  15

Glu Lys Val Phe Leu Glu Cys Val Gln Asp Ala Pro His Ser Lys Met
            20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
     50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
            115

<210> SEQ ID NO 74
<211> LENGTH: 116
<212> TYPE: PRT
<213> ORGANISM: Artificial Sequence
<220> FEATURE:
<223> OTHER INFORMATION: mutant beta chain (b35)

<400> SEQUENCE: 74

Asp Val Lys Val Thr Gln Ser Ser Arg Tyr Leu Val Lys Arg Thr Gly
1               5                   10                  15

Glu Lys Val Phe Leu Glu Cys Val Gln Asp Ala Pro Leu Glu Lys Met
            20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
     50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Asn Ser Gly Asp Pro Tyr Glu Gln Tyr Phe Gly Pro Gly Thr Arg
            100                 105                 110

Leu Thr Val Thr
            115

<210> SEQ ID NO 75
<211> LENGTH: 116
<212> TYPE: PRT
<213> ORGANISM: Artificial Sequence
<220> FEATURE:
<223> OTHER INFORMATION: mutant beta chain (b36)

<400> SEQUENCE: 75

Asp Val Lys Val Thr Gln Ser Ser Arg Tyr Leu Val Lys Arg Thr Gly
1               5                   10                  15

Glu Lys Val Phe Leu Glu Cys Val Gln Asp Ala Pro Leu Ser Asn Met
            20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
     50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp 85                  90                  95

Gln Asn Ser Gly Asp Pro Tyr Glu Gln Tyr Phe Gly Pro Gly Thr Arg
                100                 105                 110

Leu Thr Val Thr
        115

<210> SEQ ID NO 76
<211> LENGTH: 116
<212> TYPE: PRT
<213> ORGANISM: Artificial Sequence
<220> FEATURE:
<223> OTHER INFORMATION: mutant beta chain (b37)

<400> SEQUENCE: 76

Asp Val Lys Val Thr Gln Ser Ser Arg Tyr Leu Val Lys Arg Thr Gly
1               5                   10                  15

Glu Lys Val Phe Leu Glu Cys Val Gln Asp Ala Pro Leu Ser Lys Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Phe Asp
                85                  90                  95

Gln Asn Ser Gly Asp Pro Tyr Glu Gln Tyr Phe Gly Pro Gly Thr Arg
                100                 105                 110

Leu Thr Val Thr
        115

<210> SEQ ID NO 77
<211> LENGTH: 116
<212> TYPE: PRT
<213> ORGANISM: Artificial Sequence
<220> FEATURE:
<223> OTHER INFORMATION: mutant beta chain (b38)

<400> SEQUENCE: 77

Asp Val Lys Val Thr Gln Ser Ser Arg Tyr Leu Val Lys Arg Thr Gly
1               5                   10                  15

Glu Lys Val Phe Leu Glu Cys Val Gln Asp Ala Pro Leu Ser Lys Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Leu
                85                  90                  95

Gln Asn Ser Gly Asp Pro Tyr Glu Gln Tyr Phe Gly Pro Gly Thr Arg
                100                 105                 110

Leu Thr Val Thr
        115

<210> SEQ ID NO 78
<211> LENGTH: 116

```
<212> TYPE: PRT
<213> ORGANISM: Artificial Sequence
<220> FEATURE:
<223> OTHER INFORMATION: mutant beta chain (b39)

<400> SEQUENCE: 78

Asp Val Lys Val Thr Gln Ser Ser Arg Tyr Leu Val Lys Arg Thr Gly
1               5                   10                  15

Glu Lys Val Phe Leu Glu Cys Val Gln Asp Ala Pro Leu Ser Lys Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Met Asn Ser Gly Asp Pro Tyr Glu Gln Tyr Phe Gly Pro Gly Thr Arg
            100                 105                 110

Leu Thr Val Thr
        115

<210> SEQ ID NO 79
<211> LENGTH: 116
<212> TYPE: PRT
<213> ORGANISM: Artificial Sequence
<220> FEATURE:
<223> OTHER INFORMATION: mutant beta chain (b40)

<400> SEQUENCE: 79

Asp Val Lys Val Thr Gln Ser Ser Arg Tyr Leu Val Lys Arg Thr Gly
1               5                   10                  15

Glu Lys Val Phe Leu Glu Cys Val Gln Asp Ala Pro Leu Ser Lys Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Asp
                85                  90                  95

Gln Thr Ser Gly Asp Pro Tyr Glu Gln Tyr Phe Gly Pro Gly Thr Arg
            100                 105                 110

Leu Thr Val Thr
        115

<210> SEQ ID NO 80
<211> LENGTH: 116
<212> TYPE: PRT
<213> ORGANISM: Artificial Sequence
<220> FEATURE:
<223> OTHER INFORMATION: mutant beta chain (bL96D)

<400> SEQUENCE: 80

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
```

```
                    20                  25                  30
Phe Trp Tyr Arg Gln Asp Pro Gly Leu Gly Leu Arg Leu Ile Tyr Phe
                35                  40                  45
Ser Tyr Asp Val Lys Met Lys Glu Lys Gly Asp Ile Pro Glu Gly Tyr
         50                  55                  60
Ser Val Ser Arg Glu Lys Lys Glu Arg Phe Ser Leu Ile Leu Glu Ser
 65                  70                  75                  80
Ala Ser Thr Asn Gln Thr Ser Met Tyr Leu Cys Ala Ser Ser Phe Asp
                 85                  90                  95
Met Thr Ser Gly Asp Pro Tyr Glu Gln Tyr Phe Gly Pro Gly Thr Arg
                100                 105                 110
Leu Thr Val Thr
            115

<210> SEQ ID NO 81
<211> LENGTH: 116
<212> TYPE: PRT
<213> ORGANISM: Artificial Sequence
<220> FEATURE:
<223> OTHER INFORMATION: mutant beta chain (bM97Q)

<400> SEQUENCE: 81

Asp Val Lys Val Thr Gln Ser Ser Arg Tyr Leu Val Lys Arg Thr Gly
 1               5                  10                  15
Glu Lys Val Phe Leu Glu Cys Val Gln Asp Met Asp His Glu Asn Met
                20                  25                  30
Phe Trp Tyr Arg Gln Asp Pro Gly Leu Gly Leu Arg Leu Ile Tyr Phe
                35                  40                  45
Ser Tyr Asp Val Lys Met Lys Glu Lys Gly Asp Ile Pro Glu Gly Tyr
         50                  55                  60
Ser Val Ser Arg Glu Lys Lys Glu Arg Phe Ser Leu Ile Leu Glu Ser
 65                  70                  75                  80
Ala Ser Thr Asn Gln Thr Ser Met Tyr Leu Cys Ala Ser Ser Phe Leu
                 85                  90                  95
Gln Thr Ser Gly Asp Pro Tyr Glu Gln Tyr Phe Gly Pro Gly Thr Arg
                100                 105                 110
Leu Thr Val Thr
            115

<210> SEQ ID NO 82
<211> LENGTH: 7
<212> TYPE: PRT
<213> ORGANISM: Artificial Sequence
<220> FEATURE:
<223> OTHER INFORMATION: Synthetic Construct

<400> SEQUENCE: 82

Leu Asp Tyr Ala Ile Asn Thr
 1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic Construct

<400> SEQUENCE: 83

Leu Thr Phe Ser Glu Asn Thr
 1               5
```

<210> SEQ ID NO 84
<211> LENGTH: 13
<212> TYPE: PRT
<213> ORGANISM: Artificial Sequence
<220> FEATURE:
<223> OTHER INFORMATION: Synthetic Construct

<400> SEQUENCE: 84

Val Val Asn Ser Ala Asn Gly Leu Tyr Ile Pro Thr Phe
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Synthetic Construct

<400> SEQUENCE: 85

Val Val Asn Arg Ala Asp Gly Leu Tyr Ile Pro Thr Phe
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Synthetic Construct

<400> SEQUENCE: 86

Val Val Asn Ser Ala Ser Gly Leu Tyr Ile Pro Thr Phe
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Synthetic Construct

<400> SEQUENCE: 87

Val Val Asn Ser Ala Gln Gly Leu Tyr Ile Pro Thr Phe
1               5                   10

<210> SEQ ID NO 88
<211> LENGTH: 6
<212> TYPE: PRT
<213> ORGANISM: Artificial Sequence
<220> FEATURE:
<223> OTHER INFORMATION: Synthetic Construct

<400> SEQUENCE: 88

Ser Arg Phe Ala Thr Gly
1               5

<210> SEQ ID NO 89
<211> LENGTH: 16
<212> TYPE: PRT
<213> ORGANISM: Artificial Sequence
<220> FEATURE:
<223> OTHER INFORMATION: Synthetic Construct

<400> SEQUENCE: 89

Ala Ser Ser Ser Asp Gln Asn Ser Gly Asp Pro Tyr Glu Gln Tyr Phe
1               5                   10                  15

```
<210> SEQ ID NO 90
<211> LENGTH: 5
<212> TYPE: PRT
<213> ORGANISM: Artificial Sequence
<220> FEATURE:
<223> OTHER INFORMATION: Synthetic Construct

<400> SEQUENCE: 90

Leu Asp His Glu Asn
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic Construct

<400> SEQUENCE: 91

Ala Pro Leu Ser Lys
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic Construct

<400> SEQUENCE: 92

Ser Tyr Asp Val Lys Leu
1               5
```